US011827892B2

(12) United States Patent
Flaishman et al.

(10) Patent No.: US 11,827,892 B2
(45) Date of Patent: Nov. 28, 2023

(54) NUCLEIC ACID CONSTRUCTS AND METHODS OF USING SAME

(71) Applicant: The State of Israel, Ministry of Agriculture & Rural Development, Agricultural Research Organization (ARO) (VOLCANI CENTER), Rishon-LeZion (IL)

(72) Inventors: Moshe Arie Flaishman, Herzliya (IL); Reut Cohen Peer, Kiryat-Ono (IL); Oded Cohen, Nir Zvi (IL); Samuel Bocobza, Tel Aviv (IL)

(73) Assignee: The State of Israel, Ministry of Agriculture & Rural Development, Agricultural Research Organization (ARO) (Volcani Center), Rishon-LeZion (IL)

( * ) Notice: Subject to any disclaimer, the term of this patent is extended or adjusted under 35 U.S.C. 154(b) by 0 days.

(21) Appl. No.: 16/972,779

(22) PCT Filed: Jun. 6, 2019

(86) PCT No.: PCT/IL2019/050657

§ 371 (c)(1),
(2) Date: Dec. 7, 2020

(87) PCT Pub. No.: WO2019/234754

PCT Pub. Date: Dec. 12, 2019

(65) Prior Publication Data

US 2021/0171965 A1 Jun. 10, 2021

Related U.S. Application Data

(60) Provisional application No. 62/681,698, filed on Jun. 7, 2018.

(51) Int. Cl.
*C12N 15/82* (2006.01)

(52) U.S. Cl.
CPC ..... *C12N 15/8213* (2013.01); *C12N 15/8216* (2013.01)

(58) Field of Classification Search
None
See application file for complete search history.

(56) References Cited

FOREIGN PATENT DOCUMENTS

| | | |
|---|---|---|
| WO | WO 01/44457 A2 * | 6/2001 |
| WO | WO 2013/181271 | 12/2013 |
| WO | WO 2016/189384 | 12/2016 |
| WO | WO 2017/015637 | 1/2017 |
| WO | WO 2017/042113 | 3/2017 |
| WO | WO 2019/234754 | 12/2019 |
| WO | WO 2019/234754 A8 | 12/2019 |

OTHER PUBLICATIONS

Sundin et al. (2001) J Am Soc Nephrol, 12:114-23, 114.*
Gottelli et al. (1994) Mol Ecol 3:301-12.*
Zwenger, "The Biotechnology of Cannabis Sativa," XP055219136, 2nd Ed., p. 1-95 (2009).*
Donald & Cashmore (1990) EMBO J 9:1717-26.*
Kim et al. (1994) Plant Mol Biol 24:105-17.*
Dolferus et al. (1994) Plant Physiol 105:1075-87.*
Wang & Oard (2003) Plant Cell Rep 22:129-34.*
Joung & Kama (2006) Plant Cell Rep 25:1081-88.*
Potenza et al. (2004) In Vitro Cell Dev Biol Plant 40:1-22.*
Saha et al. (2007) In Silico Biol 7(1):7-19.*
Guo et al. (2004) Proc Natl Acad Sci USA 101:9205-10, 9209.*
International Preliminary Report on Patentability dated Dec. 17, 2020 From the International Bureau ofg WIPO Re. Application No. PCT/IL2019/050657. (12 Pages).
International Search Report and the Written Opinion dated Oct. 1, 2019 From the International Searching Authority Re. Application No. PCT/IL2019/050657. (22 Pages).
Invitation to Pay Additional Fees, Communication Relating to the Results of the Partial International Search and the Provisional Opinion dated Aug. 6, 2019 From the International Searching Authority Re. Application No. PCT/IL2019/050657. (13 Pages).
Dyachok et al. "Fluorescent Protein-Based Reporters of the Actin Cytoskeleton in Living Plant Cells: Fluorophore Variant, Actin Binding Domain, and Promoter Considerations", Cytoskeleton, XP002793171, 71(5): 311-327, Published Online Apr. 18, 2014.
Grefen et al. "A Ubiquitin-10 Promoter-Based Vector Set for Fluorescent Protein Tagging Facilitates Temporal Stability and native Protein Distribution in Transient and Stable Expression Studies", Plant Journal, XP002793172, 64(2): 355-365, Published Online Sep. 8, 2010.
Guerriero et al. "Identification of Fasciclin-Like Arabinogalactan Proteins in *Textile hemp* (L.): Analyses and Gene Expression Patterns in different Tissues", BMC Genomics, XP021249365, 18(1): 1-13, Published Online Sep. 20, 2017.
Zwenger "The Biotechnology of Cannabis Sativa", The Biotechnology of Cannabis Sativa, XP055219136, Retrieved From the Internet, 2nd Ed., p. 1-95, Apr. 2009.
Additional Search Fees Due under Rule 164(2)(a)EPC dated Dec. 19, 2022 From the European Patent Office Re. Application No. 19734170.4 (4 pages).

* cited by examiner

*Primary Examiner* — Russell T Boggs

(57) ABSTRACT

A polynucleotide comprising a nucleic acid sequence encoding an expression product of interest under a transcriptional control of a heterologous cis-acting regulatory element comprising a nucleic acid sequence at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C) is provided. Also provided are nucleic acid constructs and cells comprising same.

15 Claims, 25 Drawing Sheets

Figure 1A:
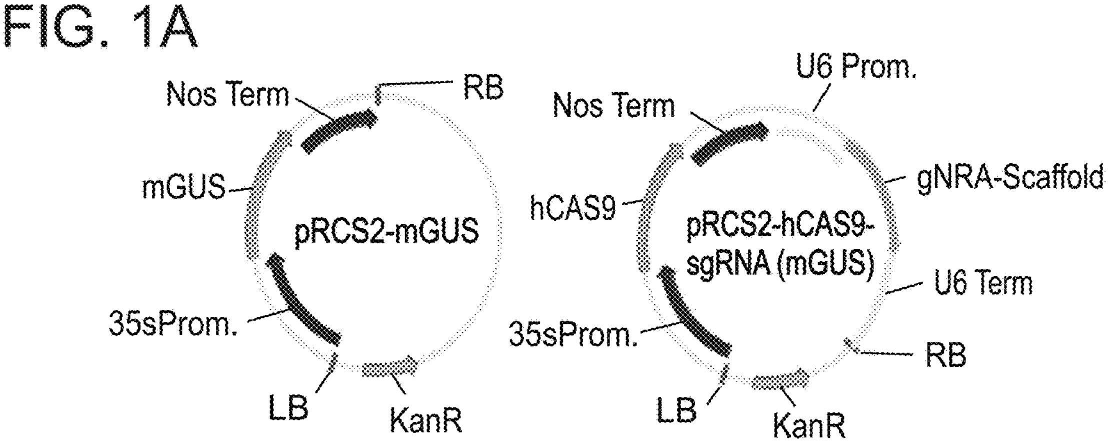

Specification includes a Sequence Listing.

GUS staining 10 days after Agrobacterium infiltration

Control- vacuum Agrobacterium infiltration with pRCS2-mGUS

FIG. 2

Ubiquitin10

>AGQNO1185210.1 Cannabis sativa strain Purple Kush scaffold50824_6, whole genome shotgun sequence (SEQ ID NO: 1)

CsUBIQUITIN10 promoter (SEQ ID NO: 2)

CCGTGAAAACTTAACACAGTACACAATATTTTTGAGCCCCATAGTAAAAAAATAAAAAAGTTAAAAATTTGAGTATGTGCCGTAAAAT
TCCATATATATGGAATATGGAAGATATATAGAAGGATAATTACACCACATCGTGAAATTTCTTAGTTTTTTACTTTCATACTGTGGG
CGGAATTTTTTTCAAAAATACTGTGTGAGTTTTATACTGGTTAAGTTTTCACTGTTGTTCTACGGTTGTTTTTAGTTGTTCCACTGTTA
TTTTAGTTGTTCGTTTTGTATTGTATTTTGTATTCTATTGTTGTTTTATAAAAATATAGTATTTTTTAAAAAATTTCCGGTGACAG
TATTTTTATAAATTTTCTTATATAAAACTAAACCTAATAACGAGGCCCAGCCCAGTAACACTTCTAAATCTCAAAATGGTCAAAAATG
TTTTAACTAGAAGCCCAAGCCCATTAAACAGGCAATGAATGACGTCATTACCGTAGGAATTGGTGGTCTTGGAAAGGCCAACTGGACAA
AACTAATATTCCAAACTTTGCGTGTAAGCGGAGCGTAAGACACGTCATCCTTTATACGTGGCCTAATATAATTGGTAACCCTAGTCAAG
TGGGTTTGGTTTGGCCTGACCAAGTCGGTTAGGATTTATCCATTTCCTTCTTTTTTAAAAAAAGAAATATCAGAGAAAGTCGGTCAAG
TTGATTTATAAATTGCCTCTTACCCTTCATCTTTCATCATTACTACTTTCTATCTAAGCAATTCTCCAATAATCATCAAATTCTCCACA
AGAACCCTAATCCCTTCTCTTCGTACATTCAAGgtaatcaaattcttgcttctgttatcatcatcatagaattttgtttatataatt
gtatcaatgatcttcgctttcgtataactttagggtttttttaatttcgttaaggttgcatttatctttaattctatcgaaaattt
tttatttttctttttcatctggaaagcgtgtatcgtatttgaatttatttgtgtgtatatataaaattgaacgaactgtatcaatga
tcttgggtttcatttaatttaggtttttaatttaccgaataatgtttggataatgatacttctttttcatttgtcaaattggtcgta
tctttgaattttcttttgtgtttatactgtttatatttgaaggaactgtatcaattatatttggtttcatacaatttagggtttttta
ttacgccaagattgtttttatttctttaaattctacgggttaattttgtaaaagagaactttctttgtctgacattattttat
tgtcttttttttttttttttggaaaaattctgatagatttgttttaattctgtatttttagATGCAAATCTTCGTGAAAACCCTAA
CCGGTAAAACCATCACTCTCGAGGTCGAGAGTTCTGATACCATAGACAATGTCAAGGCTAAGATCCAAGACAAGGAGGGGATTCCCCCA
GATCAGCAGAGGCTGATTTTCGCTGGAAAGCAGCTCGAGGACGGTCGCACCCTCGCTGACTACAACATCCAAAAGGAGTCGACCCTTCA
TCTGGTGCTCCGTCTACGAGGCGGTATGCAAATCTTCGTTAAAACCCTCACAGGAAAGACTATTACTTTAGAGGTCGAGAGCTCGGACA
CCATTGACAATGTTAAAGCTAAAATTCAAGATAAGGAGGGCATTCCCCCAGACCAGCAGAGGTTGATTTTCGCTGGAAAGCAACTTGAG
GATGGCCGGACTCTAGCTGACTACAACATACAAAAGGAGTCCACCCTTCATTTGGTTCTCCGTCTTCGTGGAGGTATGCAAATCTTTGT
CAAGACCCTCACTGGAAAGACCATAACTTTGGAGGTTGAGAGCTCCGACACCATTGACAACGTAAAAGCTAAAATACAAGACAAGGAGG
GAATCCCCCCAGACCAGCAGAGGCTCATCTTTGCCGGGAAGCAGCTAGAAGATGGTAGGACTCTTGCTGATTACAACATTCAAAAGGAG
TCTACCCTCCACTTGGTTCTCCGTCTTCGTGGTGGTATGCAGATTTTTGTTAAGACCCTTACTGGGAAGACAATAACCTTGGAGGTTGA
GAGCTCCGACACAATTGACAATGTCAAAGCAAAAATCCAAGACAAGGAGGGTATCCCACCAGACCAGCAGAGACTTATCTTTGCCGGTA
AGCAACTCGAGGATGGAAGGACACTTGCTGACTACAACATTCAGAAAGAGTCCACCCTTCATCTTGTGCTTCGTCTCCGTGGTGGAATG
CAAATTTTTGTGAAGACCCTTACCGGAAAGACCATCACCCTCGAGGTTGAAAGCTCGGATACAATCGACAATGTAAAGGCAAAAATTCA
AGATAAGGAAGGAATCCCCCCTGACCAACAGAGGTTGATTTTTGCTGGGAAGCAATTGGAGGATGGCAGGACTCTTGCGGATTACAACA
TCCAGAAAGAGTCGACCCTTCACCTTGTGCTGCGTCTGAGGGGTGGCATGCAGATCTTTGTGAAGACATTGACTGGGAAGACCATCACT
TTGGAGGTGGAGAGCTCGGATACCATTGATAATGTCAAGGCGAAAATTCAAGACAAAGAGGGCATCCCACCAGACCAGCAGAGGTTGAT
TTTGCTGGGAAACAATTGGAAGATGGAAGGACTTTGGCTGATTACAACATTCAGAAGGAGTCTACTCTTCACCTTGTTCTCCGTCTTC
GTGGTGGCATTTAA > Photosystem II reaction center W protein contains Interpro domain(s) IPR009806 Photosystem II protein PsbW, class 2 (SEQ ID NO: 3)

CsPS2 promoter (SEQ ID NO: 4)

GGTGACTGATTCCCTCAATTTCCCAGCCATCTCAATGTGGTTCATATTGAACCCTCCAGCCAAGCTACATCCAGATCCAGAACATAGACAGTTTTGACTG
GTTGTTCACCAGTATAACATCCACTATTGAAGCAAGAGTCCAGTGATTCTAGATTTACATTTCAACTCAACCACCTTCGTTTCTATCTGCCTGAGATCTT
CCCTGCACTGATAGGTAGTACTCTTTGACCATCATGTGGTGGTACAAAAGACCTAACTGGTCTATGCCATCTTCACATGAAGGAAAGTAGTTGGAC
GGTACAAACTTGTCTGAAAGGAAATCTTCATATCGCCGGATGGACTCCTTCTCAACTTTCCGACCCTTTGTAGCCAAGAGTTTGATATCAATGCCTG
CACTTGGCATTTGGGTTGAATCTATTTGATCTACAGCAGTGAGAAACAAAATCTGACTGCCCTTTACCACAGATACTTACAAATGTACATCAAATCT
CTTCACACATCTACTTAGTTCAATTAAGCCTTAAAGTTAATTATAATCTAATGCTTATCTTTTTCGGTGTGTTTTGTTGCAGGTTCTGAACGACCTTT
GTGGATGGCTGGGAGTTTGCCCTTAGGGTGGGTTACCTTTTATAAGAAAACAGTGCCTTTGGATAGAAGATGGCATATCACTGGATTGGTTATGAGTCTGA
ATTGGTTCGTGTGCAGGTTGAGAGCAGCAGTGTTACACTTCGATGGAATTATGAAGCCTTGGTTAGATATAGCAATTGGGAGTACAAGCAATATTGGTG
TAGATTCAGATAATCATACATCCACCAATAATTGAAGATTTGCAAGACTGTCAATCAATAATGGACGGACAGTACAATACCATGACAATTCTTAGCACAAA
ATTTTTACACCTTTTTTTTTTTTCCTTTCTTGCATTAGGAATTGCACTTGTTCACTTAATTCTTTTTCCCATAATGATTCTTCATGTAAAGTTCAACTAAT

ATTTTTCCCACACAGATATTTTTCTGGGGATATTACTTTAGGGAAGTTTCAAATTATAGAAATAATTCGAAACCAAAAACAAAAAAGAAAGTGGTGTATTT
TAGGGGATTCTGTAACACTTCACTAGGTTACTTTCCTGTACATATTTTTCCATTCAAGGCGCTTAACATGTATTCCGGATTATTATTTTCTTGGAATAGCCT
AATCCATATATTTTGGGATAAAAATGGAATAAAGAGAATTTTACCTGGCATATGAGAGCAACGGAAATGGAATTATTAGAAAATGGATTGTGTGGCACGTG
GAAAATTTTGATTGGGTGTAAGCAGATAGGGATAGGGCTAAGCTTTGTTTGTGTGGTGCAGTCTGGACAGATTTCCAACCAATCAGAATGCTCCGTTCCTTC
TCTTCAATCCACTGCAAAAAAACAAGGCTTTTTATAACACCATAATAACAAAATCTTCCACTGCAAAACCAGTTTTTTTTTCCCTTCCCGGAATATTTTTC
TCGGAAAATCAAGCTTCATCAAGCGATAATGGCAAGCTTCACCGCTAGTGCTCCAACCTCTTCAGTCCTCCGGGCATCCCTTCTCCACAAACCATCCTTGGG
GATCCAATCCTCACCTGTTCTTGgtaataagacctataagttttgtagttagctactctttttttctttcaatttttcaatatttgtttttttttcgaact
tgaatttgaatttgaattgtacatttagCACTTCCCACAATGGCGAAGGGAGGAAAAGTGAGGTGTTCAATGGAGAAATCTGAAAGCAAGCAAAAGATGGGT
ATGGGAGCTTCTTTAATGGCTGCAGCTATGGCAGCAACGGTGTCTAGTCCAGCTATGGCTTTGGTGGATGAGAGATTGAGCACAGAAGGTACTGGGCTTCCG
TTTGGGCTGAGCAACAACCTTCTTGGTTGGATCCTTCTTGGTGTGTTTGGTCTCATCTGGGCTAACTACTTTATCTACACTTCCACTCTTGATGAAGATGAG
GAATCTGGATTGTCTCTCTGA

*CsACTIN* promoter (SEQ ID NO: 5)

*CsACTIN* promoter (SEQ ID NO: 6)

GCAGATACTTACCACATCATCATGAAGGTTTGCCCAATACTTTTGATGAAAGAGGGCAGGGAGGCCATCCGCTCCTAGA
GTTTTTGTTGGTGGCATCTCTTTCACTGCCAATTAATAGTTTCTTCTTCTTTAAATGACTCTAGCAAATCTCGATTCAT
TTCTAGAGTAACCCATTGTGGCACTGAGTTTAGGACATCATCAAGGACATCATGTTGGATCATGGAAATGGTGAAAAGG
GTATGAAAGTACGTACTAATAATTCTTTGAACCACAACCTTGTCTTCTTGCCAAATTATCATTGTGTCCACCAACCCAT
GTATCTCATTTTTTTTCTTTGAGCAGAAGCTTCATGATGAAAGTATTTAGTATTATGATCCCCACTTTTTAACCATAGA
GTCCTACTTCTTTGTCGCCGGTACTTCTCATCCTTATCAAGAAAAAAATTTGACTTTTTTTCTTATTTTTTAATTTCCA
TCCCAATGGATGGTTGCTGAACCTTAGATAAGTCACCCAAGGTCTTCTTAACTCTATCAAGTTCTTCATTGTTTTTTGT
TTTTTTTTCTTATTCCACTTCTTCGAAGCTTTCCCACATAGAGAGGCCCTCCGTTTGAACCCCTTTGTCATACCTAAAT
TAGCTTTGTCCCTCTAATGCTGCTCAGCAATCGCTTTACACTCCCCATCCTCGCACCAAGCCTCTTCGAAATGAAATCG
AGTTCTCCTCCTGACCATTCCAAACTTCTATGTTGAATGACCTAGTGGTATGTCAATCACAAAGGCTCTATGGTCGGAC
TCCAGCCAGCCCAACACCTTAACATCCGCTCTCGCAAAGCTTTCCATCTAAATTACACAATGCCTTGTCTAGCCTCTCC
ATGACCCTATTTTCCCCATGCCCATTACACCAAGTAAGTTCAGTTTTACAAGTGCAAAAATTAGCCAATCCACATTCAT
CGATAACCTCCCTAAATTCCTCCATATCCTTCGAAGCTTTAACCCGACCCCTATTTTTTCAGATAGACTAACAATTTCA
TTAAAATCCCCAACACAAAGCCATGGGCTAGTAATTTCATTATGTAAATAGCATAGTAATTCCGAAGAAAACTTCCGTT
GAGATGTATTAGGATTCCCGTAAAAACCCGTCAAATTCAACGGTAAAAGTCCTCCAACCACCACAGTCGTAATGTAACT
AGGAGAACTCGAATCCACTCGTAATATTTCTTTTTTTTAAAAAAAAAAAAAGCTAATATTTTAATTTTTTTAATTAAAT
TTTAGCATTTGAAAATAAATAAAGTGGGGAGTAAAATACATTTATAATAAGGGATGGAGCCCAGCCCAACCAGCCAAGA
GTGCAACCCACGTACTGTGTTAGCTGACAAATGAATGAAAAGAATATAGAAATGGATTTGTTTGAAGACATAATGACGA
GTCCAGACTGTACTCTTAATCTGATCTGACGGACCACATTGCATCATCATCACCATCGCTCATCTTTATATACTATTAT
TACACACCTTCCCTTTCCCTCTCATTCTCCTTCTTCTCTCTCAAACCTCTAAACTCTAAACCATTCATTCTTTCATTCA
TTTACCACAAACCCTCTAAACTTCCATCTTGCTTTTCGCATTTCAACAGGTTCATAATCTCTTTCGATCTCTTTATTTC
ACCCGATCTGTGCTTATGTTTTAGTATTATCATTTTTTAATTTCATATTTATGTATGTTTTACAATTTGTATTTCATTG
TTGGATTTATGATTTTGTGTTTATTTCTTTGTCCAAGTTGTTAAAATTAATGCTCGATGAATTGGGTTTTCGTTAAAAA
GATTTTTTTTTTTTTTTGTTTCTTTTTATGTTTTTTAAGATTAAATATGCAAATATAAATGTGGTAAATAACCTAAAGA
AGAAGAAGAAAGAGAAAAGATCAAAAATTGAGTTCATCTCTACAAATTGATTGTATCTGTTTTATTTTGTGTGTACATT
CTTATTTTAACACAAGAATTTGGTGTACAAATAGATACATGCATTCGATTTATGTTGCATTGTTAGTATCATTGTATCG
CTATATGACGATCTACCGCTTTTATTTATTATTTTATGAAAGATGTTCTTATAACATAGTTTGGTGAACAAATAGGTAA
GTGAAGATGGCAGATGCAGAGGATATTCAGCCACTTGTCTGCGATAATGGAACTGGAATGGTCAAGGTATTAATGTTAT
TTGTCATTGTTGAAAAGTTTCCCATTGAATCATTAATCTTCTGTGCAAAAGCTAGCTTAATGTTACTTGTGGGTGTGTA
GAATTTGCCTCTTGACCATTAATTATTGTGATCTTACCTATTAGGCTGGGTTTGCTGGAGATGATGCTCCACGAGCTGT

FIG. 2 (continued 1)

GTTCCCCAGTATCGTGGGTCGTCCTCGTCACACTGGTGTAATGGTTGGAATGGGCCAGAAAGACGCATATGTGGGTGAT
GAGGCACAATCCAAGCGAGGTATCTTAACTCTGAAGTACCCAATTGAGCATGGTATTGTCAGCAACTGGGATGACATGG
AAAAGATCTGGCATCACACTTTTTACAATGAGCTTCGTGTTGCCCCTGAGGAACACCCCGTTCTTCTAACCGAAGCTCC
ACTTAACCCCAAGGCCAATCGTGAAAAAATGACCCAGATCATGTTTGAGACCTTTAACACCCCTGCTATGTATGTTGCC
ATTCAAGCCGTTCTTTCTCTGTATGCCAGTGGTCGTACTACCGGTGAGTACCAAGTACTTTCTTCTTTTCATTGTCATA
GCATGATTTCTTGTTAGAGTATCCTATAGACACTGAAATGAGACATTAAATATGGTAAGAACTGAGATTTTACTAATAC
CAATCTCATTCTGTTTACCAACTACTTGCATCATGATATCTTACCTTGTCAAATATTGTAGTGTGGCTTTGGTTTTGGA
AATTATATTTTTCTTGAAGTTTAAACCTTGACCCTCATTTTCTAATACTATTATGTAGCTTTTATATTGCCCTGTCTTA
AAATAATTTAGCTAGAAGTTTTGCCTTAGTTTTGCAGGTATTGTGCTGGATTCTGGTGATGGTGTAAGCCATACTGTCC
CCATATACGAGGGATATGCTCTTCCTCATGCCATTCTACGTCTTGATCTTGCTGGTCGTGATCTTACTGATCACCTAAT
GAAGATTCTCACCGAGCGTGGATACTCCTTCACCACCACTGCTGAACGGGAAATTGTGAGGGACATGAAGGAGAAGCTT
GCCTACATAGCTCTTGACTTTGAGCAGGAGATGGAGACAGCCAAAACTAGTTCTGCTGTTGAGAAGAGTTATGAGTTGC
CAGACGGGCAAGTCATCACCATTGGCGCCGAGCGATTCCGATGTCCTGAAGTTCTTTTCCAACCTTCATTGGTTGGAAT
GGAAGCAGCAGGCATTCACGAAACTACTTACAACTCCATCATGAAGTGCGATGTTGATATCAGAAAGGATCTTTACGGT
AACATTGTCCTGTCTGGTGGTTCAACCATGTTCCCAGGCATTGCTGATAGGATGAGCAAGGAAATCTCTGCTCTTGCAC
CAAGCTCTATGAAGATTAAGGTGGTCGCACCACCAGAGAGGAAATACAGTGTCTGGATTGGAGGCTCCATCTTGGCCTC
TCTCAGCACCTTCCAGCAGGTTTATATTTTTTCATATCTAAGTTTGGCATGATGATCTTAATATGATGATTCAATAATT
ACTGATATCATATTTTATCTTTTCCTTATGCAGATGTGGATTGCAAAAGCAGAGTACGATGAGTCTGGGCCATCAATTG
TTCATAGGAAATGCTTCTAAGCATGTGAGAATTAGAACTACTGCAGAGAGAAAAGCAAGTACTGTTGTTTTGATTATGT
TGGAGAAAAGTGTTGTTTGCAGAAGGTTCATTCTAGCTCGTTACCTTTTTTTATTCTCAACTTGAAGTGACTTCGGAA
GGCCAGGAGTTAATTTATCCAATTTGTTTCTTTTAAATTTTATTTTATTTTTGTTATTACAACTTCTTTGATTATCATT
ATTATTATTTTTTGGTCATTCCATCCCAAAATTCCGTACTTACAAAAGCTCATATTGAATGCTTAAATTTCTTATGAAC
CCAATTCATGAGATAAAACCTTTATTTTATGAATCAAATAATCTGTATGATCCACGTGAAAACTAAATTTTATTTACAC
GGCAAAAGCAGTTCTTCTAAAAGAAGACTTGCAAGTGAGGCTTCTTCTCAGCATTTTTACACTCAAAATATCATCTTCA
AATAAACAAAAGTTTATCAAACAATGTCAAAGGTTGACTTAAACTATTGTAATCAATTCTCTTTGACTCTTAGTTCTGC
CAAGGAAGAAAG

*CsTUBULIN* promoter (SEQ ID NO: 7)

*CsTUBULIN* promoter. (SEQ ID NO: 8)

CCTCAACGAACATCTGTTTTAAGTGGAGAGGATTTTGTGAAACAATTATTAGGTGGTCATGAGAGAACATGTTACGAATTGT
TGCGAATGGATAAGAATGTATTTGTTGAGCTTTGTACTTGTTTAAAACAAAAGAATACATTAAGGACACCCGAGAGGTTAAAGTTGAA
GAGTCAGTTGCTATTTTTCTTATGATTGTTGGTCAAAATATGAGAATGAGACTTATAGCAGATCGATTTCAACATTCGCTTGAAACCAT
TGATAGGCATTTTCGTCTAACATTGAAGGCAATATGTAAATTAGGACAAGATATCATTCGTCCAACTCAGTCTCCATTACCTTCTCGTA
TTGTCAATTCCTCGAAATACTATCCATGGTTTCAGGTATTTAACTACATTTAGTGTAAGATAAATAATACTTTCACATATTATTAGAGT
GTATTTTTTTTTATTAACTTTTCTTTATTTTTTTAATCAGAATTGTATAGGTGCAATTGATGGAACACATGTGAGTGCATGTGTCCCT
GCAGATAAGCAAGTCAGTTACAGAGGTCGAAAAAATGTAGTAACACAAAATGTTTTATGTGCTTGTAACTTCGACATGTTCTTTACTTT
TGTATCTGCTGGTTGGGAGGCACTGCAAATGATTCCAGGGTGTTTATAGATGCAATTACAACACCTGAATATAAGTTTCCACTGCCTAA
AGAAGGTATTTGTAACCAAAATTTAGTTATTATTTTATTATTTAGTCATGGTGCTTATAGAAAATGAATCCTTTTGTAGGTGAATATTA
TGTTTTGGATTCTGGATTTCCATGTACAAAAGGTTTTCTCCCACCATATCGTGGTGAAAGATACCATTTGCAAGAATACAATAGTGGAC
GTAATGGACCGCGTGGCATGAAAGAACTATTCAATTATAGACATTCTTCACTTAGAAATGTCATTGAACGGTGCTTTGGTGTGCTGAAA
GCTCGTTTCCTATATTAAAGATGATGCCACCTTACAAATTGAGTCGACAAACTTTAATAGTAATTGCTTGTTGTACACTTCATAATTTT
ATTCGACAACGCACCCAATATGATCATATGTTTAGAGAATGGGAAGAAAAAGAACTTGAGAGTGAAGACAACATAGAAGGATGGGAAAC
CAGTGTGTCAAGATATGAAGTTAATTTGTCTGATGAATCTGCTGCGGCAATGGCACGTGTTCGAGATCGTATTGCTCAAACTATGTGGA
CGGCTTATAATAATAGAAATTAGTCAATTATATTTTAATGTTTGATGATACATTCAGGATTAAATTTATTTTTATAAGGATATATTGTA

FIG. 2 (continued 2)

GACTAATGGTTATTTTACATCGATTTTAGATTAAAAAATTCTTTAAGAATTTCATAATTATATTTTTAAGTATTATAATATTATATTTA
CTTATTATTTAAAATTATTTTTTTAAATAAATTAGATATTAATATGTTATTGAATTAAATTAAAATTTGTAATATTTATTTTTTTAAAA
AAAAAAACAACACAACACCAAAAAAATAATAATAACAGTAATTTTTTTATTTATATATATTTTTTTAAAAAAAAGCAATTTTTAAAAAC
TTGTTGTTTTTACTATCCAAACATGTTTTCAGTTTTTGTTGTTTAAAAACTGTTTTTAAAAAAATATTAGCCAAACACCATTTAATTTTT
AAAATGACAAAAAACTGTTTTCTGTTTTCACTTTTAAAAACTGTTTTTGAAAACTAAAAACTGAAAACACAGCCAAACAGCCTCTAAGA
GATTCCCCTTTTTTGTAAATTAGCTTTGGAAGATTGCACAATGAACAACTTGATATTTGTTTGGGATCTTAACCCAAGAGATATTTTCT
TTAACAAGTCTAGTGATATTTTCCACTACTAAATTATTACAATTATAGGCAAGTCCAATAGAGTCAATTCCCTCCAATTGGAATTCAAA
ACCACAACGGTCATGACAGCTGGACCCCACACCCACATCCCCACAACGGTCAGTTTCAAATTTTGAAACGTCCCCAAATTTTTTAAAAA
CCGACTTAAAAATTTGTCCTTTTTATACCCTAAAAAAACCCTAGCTGCTCAATCATATTTTCTCTTGTAAAAAAAAGTAACCGAAAAGC
CTAAAACAGAAGAAAAAGCAAAACCTAAAACCAGAGAAGAGAAATGAGAGAGTGCATCTCGATCCACATTGGTCAGGCCGGAATCCAAG
TCGGTAACTCCTGTTGGGAGCTCTATTGCCTTGAACATGGCATTCAGgttggtttttcttcttcttcatttgtgatttattctcattt
ggatcttacttacaatgattctcttctcttacccagCCCGATGGTCAAATGCCCAGTGACAAGACCGTTGGAGGTGGAGACGATGCCTT
CAACACGTTTTTCAGTGAAACCGGCGCCGGAAAGCATGTTCCCCGTGCTGTGTTTTTGGATCTAGAACCAACGGTCATCGATGAAGTGA
GGACCGGTACTTACCGCCAGCTTTTCCATCCCGAACAGCTTATTAGCGGGAAGGAAGACGCAGCTAATAACTTCGCTAGAGGCCATTAC
ACAAgtaagaagctttttaaatttttggttaggtttttgttttgtgagtgtttgttgaaatgtccttgaatttttttgttcaaatttttg
atttttgtttttgttttgtgggcagTTGGGAAAGAGATTGTAGATCTATGCCTTGATAGAATCCGAAAGCTTGCTGATAACTGTACTG
GGCTTCAAGGGTTTCTGGTTTTTCACGCTGTTGGCGGTGGAACTGGATCTGGTCTTGGATCTCTACTTCTTGAGAGACTCTCTGTTGAT
TATGGAAAAAAATCTAAACTTGGTTTACAGTTTACCCATCTCCACAGGTTTCCACCTCTGTGGTTGAACCTTACAACAGTGTTTTGTCT
ACTCACTCCCTTTTGGAACACACAGATGTGTCTGTTCTTCTTGATAATGAGGCTATCTACGACATTTGCAGAAAATCACTTGATATTGA
AAGACCCACTTACACTAACCTTAACAGGCTTGTATCTCAGgtataaaatcacttgatgtaatctagtcttatgttattcttgttttagg
ttacttaatgagctttttctatgtttgggcaacagGTTATTTCTTCACTCACTGCTTCTCTTCGATTCGATGGAGCTCTTAATGTGGA
TGTGACTGAGTTTCAAACTAATCTTGTCCCTTACCTAGAATCCATTTCATGCTTTCGTCATATGCGCCTGTGATTTCTGCAGAGAAAGC
TTACCACGAGCAACTTTCGGTGTCTGAAATCACAAACAGCGCTTTTGAACCATCTTCAATGATGGCCAAATGTGATCCTCGACATGGAA
AGTACATGGCTTGTTGTTTGATGTACAGGGGAGATGTTGTACCAAAGGATGTGAACGCAGCAGTCGCCACCATCAAGACCAAGAGAACT
ATTCAGTTCGTTGATTGGTGCCCAACTGGGTTCAAGTGCGGTATCAACTACCAACCACCCACAGTCGTTCCAGGAGGTGACTTGGCTAA
GGTTCAAAGGGCTGTTTGTATGATTTCAAACTCCACAAGTGTTGCAGAGGTGTTCTCTAGGATTGACCATAAGTTTGACTTGATGTACG
CAAAGAGAGCTTTTGTGCATTGGTATGTCGGTGAAGGTATGGAGGAGGGTGAGTTTTCTGAAGCGAGAGAAGACTTGGCTGCCCTTGAG
AAGGACTACGAGGAAGTTGGGGCAGAATCTGCCGAAGGTGACGATGATGATGAGGGAGAGGAGTACTAAGAAAAAGCTTTCATTAATAT
AAGTATGTGTTCTGCCAATGGACTCATTGGTCTGTAACTGAGATTACAAACATCTACTATCCTTGTTTTTAATTTGATGTTAGTTACAT
TTTGTTCTTTGGTTGTTGAAGTATAACAATTGTTCATTTTGCTTAAAAAAATTCCAAATTTTTCATATGTTGAAACTGAACATATGGAT
CAACATGATTTTGCTCGCTTCTTGGTTATTTTAGATAATGATTCACTTTGAGAGTGAGGACTTTCACAAAAATCATCATCAATTATGGC
ACCATCATCAATTTTATTTAATTAAACATGAAAAAGTTGGATTGAAAAAGGCTTATTTCTCCTCCTAGAACCATTATTTCAGACTGTAC
AGAATAAAGGTAAAAAAGAAAAACTGCTTCACTATCTATCTCTCACTACTTCTTGGTTACTGACTCCTCCCTATTCTCTAATCAAAGAA
ACATAAACAATAAGCTAAAGAAAGAAAAGAGAGAAAAAAGTAACTAAGTGACCGAACATCACAAACATGTCTTCTCAAGTTCCCAACTT
CATCATCATCTGCTC Eukaryotic translation initiation factor 5A-4 (SEQ ID NO: 9)

*CsEIF* promoter (SEQ ID NO: 10)

AGTGAACTGACAAATCAGGGAATAAACTTTCGAACATATAATTAAGATTATATTCCACTGTGTTGACAACACTATAATCATTAACAAATTGATATGTTCTGG
ACTTAAATAGAATTCATACATTATGTACATATAATCATGAAATAAATCATGTGAACCATGCAACATTAAATGTTATTTATGATCTATATTAATAAGTAAATC
TAATTATATTGAAATGAGTTTTATTTAGGGCATAAAACCCAACATTTTCCAATTGTAATTGGGGGCAAAGATAAAAAGAAGTGCACAAATCTGGCACATATT
CTCACTGAAAGAAGAGAGTTCACACAAACAAAGCAGACTACCAAAAGTCGCTAGAGGGAGAAACCATGCAAGCCAACAAGCAACACTAACCAAAAGAAAGAT
CTAATCGGGCACTGAGCTACACACAATCCCCTCCACAACCACACAAACAAGCCTATGAGCACGACAAAACAAGACCACAGCTGAACCAGAAACAAGCTCCGA
GAAACCGAAAACAAAAGACCGAGGGAACACCAAGAATGACAAGCTACAACATCAGCCAGGAACAATCCCAAATCTCATGAAAGAACACAAAAACTCTCAATCC

FIG. 2 (continued 3)

CGTTACTAGAACACCATACGGGGGGAACTAGAACATGGAGAAAGAAGGCTAGAAATCCATTCCCAACGTCCTGAGAAGCCACCGGAGCAACACCAACTAAGA
CAGGATCCTGACGAAAGGACGAGATTCAAAATCGCCTAGAACAAAGAGAACTAAAGGAAAAAGGCAACTAAAGTGAAAGAGCTATTAAGAACACTGCTGAAC
AAAACCACAATCTCACGACCACTAAAGCAGTCACAAGGAGCCAGAAACAGTGACGGAGGAACGACTCAAAGTCTCACGGCAAGACTCAAAGGACGGAATG
CAAAGCAAAATCGCAAATTGTATGGAAAGAACAAGGGCAATTTCGGTTTTAGCGAGACTAGTATCATTGTATAGCTTTTGCCTATTTGAGGAATTTGGATGA
TGGCAAGTTTTCTAAAAAGAAATGAACATAAAAATAAAAAAGAAAATGAAAAAGTTACTGCCCTTTTGAGGAGGCGAATCGTGACAGAATCCCACATGCGCA
AGCGTCACATAAACGCTGATTAATAAACATTTGATTCTCTTCAACTCATTCCATCCAACGGTGGAAAATCTCCAATTTCTCATCAGATATATACATTTTTAT
TATTTTATTTAAATATTTTGTTTTGAAACCCTAGGTTTTGTTTGAGATCAAGTCCGCAGCACTCCTCCTCATTTTCTTTCACAAATATTATTTCAAAACTTG
TACCCATATATAAATTGTCTCATTTCTCATCTTCCTCAACCCTTCTTTTCTCTGCCTTCTTCCATTTTTTGGGGTTTTCTTCTTCTTCTTCTTCATCTTTTC
CGCTCAATCAGCTATGTCGGACGAGGAGCACCAGTTTGAGTCCAAGGCCGACGCCGGAGCTTCCAAGACCTATCCTCAGCAAGCTGGTACTATCCGCAAGAA
TGGTTACATCGTCATTAAGGGCAGGCCCTGCAAGgttctctttatcattttccttttatcagattggattcactacggatctggaacttggatttttattct
ttattatttgttatttgttccaaataagcgataagataaggttaaagtttgatttttttttctcataatctttattgggtttttgttgttcgatgttgttt
tggtatattggggtttgactgggcttgtggtagtgataagcgtctgtgctttatgtgatagctttcggtcgaaaatgagaaatttgttgtctggtattagaa
aatgttggattcgaaaccctttattaagtttcttattgcatgttttgggtcaataatttagggattattgaagatagcttgttattttcctttgtttctgt
ttcgtcgtggcggttatatataactcacatgtttggattgatttaattaaacgaattattaaagaaaacttttgatgcaagaaggatcttatcatggaaatg
attgtttattgattctattgatgagtttattattattgttctaaagaaaatctttgactttgcaatatttacagGTTGTTGAAGTTTCCACTTCCAAAACTG
GAAAGCACGGTCACGCTAAGTGTCACTTTGTTGCCATTGATATCTTCACTGCAAAGAAGCTGGAAGATATTGTTCCATCTTCCCACAATTGTGATgtatgat
cattctttgctcttctatttgtcttgtttgtgttatcgttttgacacctttttcttatctcactttatccattctcgtgtctttttattgcagGTCCCTCAT
GTCAATCGTACTGACTACCAGCTGATTGATATTTCTGAGGATGGATTTGTAAGATTTATTTCCTTTTTTTACTACTTTTGGGTCATATTTGTTCACCCCTTT
CTTGTATTGTTTCACTAGTCATTTCAACTTGGGCTAACTTGAGTTATGATATTTTAGGTGAGTCTGCTTACTGATAATGGAAATACCAAGGATGACCTGAAG
CTTCCAACTGATGACAGTCTGCTCACGCAGgtttgttgatatgaatgacttctgctaaatctgtgtcaatatctctgtagacattgatgtgtcattaattat
gctcttttgggaattgatgtgtcagtttatctattctggccttgcaacgctgatagaaatttttaggtggtgattattatagctaataattaatggtcatgg
ctttggaattgtacagATCAAGGATGGATTTGCTGATGGGAAGGATCTTGTCGTGTCTGTCATGTCTGCAATGGGAGAGGAGCAGATCTGTGCCCTTAAGGA
CATTGGCCCCAAGTAGTTCATTGCGTGTTGCTCTATCAAAACTCAAAATGTTTTTTTATCTTAAGACCATAAATTTATTGTGATACAGCTTTGTTGTTGATG
GTGGTTTTATTTGCTTTGAGAATATGTGGTCACGTTTTATTTTATTTTTCCTGCAAATTATTCTGAATGAGATGTTACCAAAATTATCATATTCAACTTCAA
TATTTTTTTTAATGTTGTATGAACCGGCAAAACGTGCAATCCAATCTTTGTATTTGTATCTAATTTGCCAGTATTGGCAAATTAAGTCAGCTATTTTGCCAG
TATTGGCAGTTAA FIG. 2 (continued 4)

a.

1kb ladder + 1 2 4 wt - b.

1kb ladder + 1 2 4 wt -

FIG. 6 seq1 SEQ ID NO: 11 TCATGACCTGCAcCTGC-tAGTATTTCGCAGTAGATAAACCAGCCAAACCTACAAGAATT
seq3 SEQ ID NO: 12 TCATGACCTGCAcCTGCCtAGTATTTCGCAGTAGATAAACCAGCCAAACCTACAAGAATT
seq4 SEQ ID NO: 13 TCATGACCTGCAcCTGCCAAGTATTTCGCAGTAGATAAACCAGCCAAACCTACAAGAATT
PDS wt SEQ ID NO: 14 TTATGACCTGCATCTGCCAAGTATTTCGCAGTAGATAAACCAGCCAAACCTACAAGAATT
seq2 SEQ ID NO: 15 TCATGACCTGCATCTGCCAAGTATTTCGCAGTAGATAAACCAGCCAAACCTACAAGAATT
********  **************************************

FIG. 7

AAAAAAATCATTAGGACTGAAGAAAAATGAATTGCTCAGCATTTTCCTTTTGGTTTGTTTGCAAAATAAT
ATTTTTCTTTCTCTCATTCCATATCCAAATTTCAATAGCTAATCCTCGAGAAAACTTCCTTAAATGCTTC
TCAAAACATATTCCCAACAATGTAGCAAATCCAAAACTCGTATACACTCAACACGACCAATTGTATATGT
CTATCCTGAATTCGACAATACAAAATCTTAGATTCATCTCTGATACAACCCCAAAACCACTCGTTATTGT
CACTCCTTCAAATAACTCCCATATCCAAGCAACTATTTTATGCTCTAAGAAAGTTGGCTTGCAGATTCGA
ACTCGAAGCGGTGGCCATGATGCTGAGGGTATGTCCTACATATCTCAAGTCCCATTTGTTGTAGTAGACT
TGAGAAACATGCATTCGATCAAAATAGATGTTCATAGCCAAACTGCGTGGGTTGAAGCCGGAGCTACCCT
TGGAGAAGTTTATTATTGGATCAATGAGAAGAATGAGAATCTTAGTTTTCCTGGTGGGTATTGCCCTACT
GTTGGCGTAGGTGGACACTTTAGTGGAGGAGGCTATGGAGCATTGATGCGAAATTATGGCCTTGCGGCTG
ATAATATTATTGATGCACACTTAGTCAATGTTGATGGAAAAGTTCTAGATCGAAAATCCATGGGAGAAGA
TCTGTTTTGGGCTATACGTGGTGGTGGAGGAGAAAACTTTGGAATCATTGCAGCATGGAAAATCAAACTG
GTTGCTGTCCCATCAAAGTCTACTATATTCAGTGTTAAAAAGAACATGGAGATACATGGGCTTGTCAAGT
TATTTAACAAATGGCAAAATATTGCTTACAAGTATGACAAAGATTTAGTACTCATGACTCACTTCATAAC
AAAGAATATTACAGATAATCATGGGAAGAATAAGACTACAGTACATGGTTACTTCTCTTCAATTTTTCAT
GGTGGAGTGGATAGTCTAGTCGACTTGATGAACAAGAGCTTTCCTGAGTTGGGTATTAAAAAAACTGATT
GCAAAGAATTTAGCTGGATTGATACAACCATCTTCTACAGTGGTGTTGTAAATTTTAACACTGCTAATTT
TAAAAAGGAAATTTTGCTTGATAGATCAGCTGGGAAGAAGACGGCTTTCTCAATTAAGTTAGACTATGTT
AAGAAACCAATTCCAGAAACTGCAATGGTCAAAATTTTGGAAAAATTATATGAAGAAGATGTAGGAGCTG
GGATGTATGTGTTGTACCCTTACGGTGGTATAATGGAGGAGATTTCAGAATCAGCAATTCCATTCCCTCA
TCGAGCTGGAATAATGTATGAACTTTGGTACACTGCTTCCTGGGAGAAGCAAGAAGATAATGAAAAGCAT
ATAAACTGGGTTCGAAGTGTTTATAATTTTACGACTCCTTATGTGTCCCAAAATCCAAGATTGGCGTATC
TCAATTATAGGGACCTTGATTTAGGAAAAACTAATCATGCGAGTCCTAATAATTACACACAAGCACGTAT
TTGGGGTGAAAAGTATTTTGGTAAAAATTTTAACAGGTTAGTTAAGGTGAAAACTAAAGTTGATCCCAAT
AATTTTTTTAGAAACGAACAAAGTATCCCACCTCTTCCACCGCATCATCATTAATTATCTTTAAATAGAT
ATATTTCCCTTATCAATTAGTTAATCATTATACCATACATACATTTATTGTATATAGTTTATCTACTCAT
ATTATGTATGCTCCCAAGTATGAAAATCTACATTAGAACTGTGTAGACAATCATAAGATATATTTAATAA
AATAAATTGTCTTTCTTATTTCAATAGCAAATAAAATAATATTATTTAAAAAAAAAAAAAAAAA

Vacuum Agrobacterium Co-infiltration of 10 day old culture 7 days Recovery

GUS staining 10 days after Agrobacterium Co- infiltration

FIG. 9

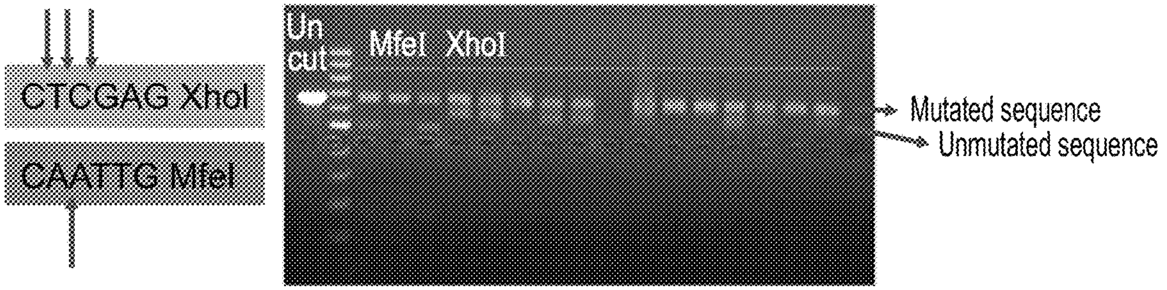

THCA synthase genomic sequence (SEQ ID NO: 421) from public database. (in underline are the chosen sequences for CRISPR targets; the XhoI target site and the MfeI target sites are indicated in bold):

1 atgaattgct cagcattttc cttttggttt gtttgcaaaa taatattttt ctttctctca
61 ttccatatcc aaatttcaat agctaat CCTCGAGAAAACT TCCTTAAATG cttctcaaaa
121 catattccca acaatgtagc aaatccaaaa ctcgtataca ctcaacacga CCAATTGTAT
181 ATGTCTATCC TGA attcgac aatacaaaat cttagattca tctctgatac aaccccaaaa
241 ccactcgtta ttgtcactcc ttcaaataac tcccatatcc aagcaactat tttatgctct
301 aagaaagttg gcttgcagat tcgaactcga agcggtggcc atgatgctga gggtatgtcc
361 tacatatctc aagtcccatt tggttgtagta gacttgagaa acatgcattc gatcaaaata

FIG. 10 metallothionein 2A

ACTGTAGTCGTTTTTTGGAGTAGCAAATCTAGCTGCTGCCCTCTTTTTCTTCAATTCCCCCTCTGCCTAAATATGGAAAGCATATGTA
TATATGCTATAGCTTGCACACGTGTCACATATTTGCATATATAATGCTAGCCCTTCCAATCATGGGCTGCCCCCTTTTTTTTTCTTTT
TTTTTTTTTTGTTTCTTTATTATTATTTTTTTTTTTTGCAAGCCCATTAGAATAGTAATTATACTTTATGAATATTGTGTACAAGATT
TTTGGCTTTGATAGTTCATGGACTTTTTTACTCTATGACTTTTGAGACATTATGCACATAATAAAGTCCAAACTATATATTTAAGCTC
TTACAAAAATACACAATATTAAGAATAATACTTTAACATGGAAACTAAATAAAATTGATAAAATATTACAAAAATTAACTAAAATTAA
TCTAAAAATACTAAAACTAATATTTATGCAAAACTAAATAAAATAATTAAACAGTCACTAAAATAAACTAAAAATGCTTGAGAACAAAA
CTAATTTAATGGACAAAAAGAGCTAAATAGCTCTATTTCATAGAGTTATCAATAGGCCTATTTGGCATTTCTCTGACAGTGGTTCTTT
CTCGGTAAAGAGTGGATATTGGAGTACTGTGTCCAGGTTGGGTGGGGCCAAGCTTCAGGCTCCTCTGGTTCTTCCCGGTGGTGGAAACT
TCTTTGGCAGCTGAATCTTCCGCCTAAGATAAAAAATTTTGTGTGGAAGGCATGTCTGAATTTCATTCCGGCTTATGCCAATTTATCTC
GTCATGGTATGAAGGTTTCTACAATATGTCCAATTTGCTCTCAAAATAACGAGACTACTCTTCATGCTCTTTGGCTCTGCCCTTCTCTT
AAGTCTATTCGTTCGGTTTGGTTTTTGAGTGACCTCGACTCCTTGAAGGACGCCTCTTGCTATTATGAGTTATTATTGGGGTGTATGGA
TATCTTGAAACGACAGGAACTTGAGCAGTTTATAACCCTTGGCTAGCATATTTGGAACAGGCGAAATACCTTTGTGCATGATCATAAGC
TCCTCTCTGATAACATGGTTAGTGCTTGGGCCATGGATTATTTATGGAAATATCAAGATGCTAATAATGCCGAGGCAGCTTCTTTGGGT
TCGACTTCTAGCAATGCAAGTAATCGACTGGTCTCATCTGAGACGGATCTGGTTCTTGGTGAGTTCAATCTTTTTGTGGATGCTGGGGT
TTGTGTTGAGAATCGAAAATAGGATGGGGGCTTTGGTTTCCAATCGTTTGGGCATGTCATATTCTCGAGTGCAGCTCCTTGCTCCTT
GCGCGGGTTTGTGTGAACCTCACGTTGCTGAAGCCAAAGCTTTGGTCCATGAGCTTTCTTGCTGCGTGCAGATGGGGTATACGGTGATT
ACTGCTTTCTCTGATTGTCAACGGGTAGAGTTCTTGCTGTCAATAGCAGGGGCCCTTGTTTCAATAAGTTTGGTATTGTTCTTAATGAT
ATTAATGATATTAAGAATTCTTTCAATACCATATCTCTGTCGCATTGTAATCGGTCAAAGAACTATGATCCTCATTCTTTAGCAAAACG
AGCGTTAGATTTAAATAAGGCTCGGGTGTGGTGGCCGAGCTTGCCTACTGATTTAGCTGTTTAAATTTATCTATCTCTTGTATTCTAAT
CTTTTGGCTTGATGGCTTTTAATAGAATCTCTCTGTTTTCAAGAAAAAAAAAATAAATAGATTTTATATATCCATTAAAAGATAAACTT
TTTATATACTAAAAGTATAATAATCATGATTGATGACCAAGTGCGCGAGATAGACATTAGGACTTATCTCAACCGGAACCGTTGATTAT
ATCTTTGATCAATTAAAGTCAATCGGACGGTTGATACCTTAACGTCAACGTATAGAGAAAACTCTAGACACATGTGCCAACATCTGAGA
TAAAAAGGGGGGCCACGTGGGAGTTAGAGCACCGTGGATCCCTTGATTAGCACATGTACGGTAGAGATTGACTCGCTCTTGCTCTATAA
AAAGAGGTGCGGTTTAGTTCATTTCTGATTTCGCACTCAAAACTCGCTCTATCTTCAATCATCAAAACCGAATCTTCCTCATCTCTGAA
GAAAATTTGTTATTTCAATTCAAACTATACTCAAACATGTCTTGCTGTGGAGGAAGCTGTGGCTGTGGATCTGGTTGCAAGTGCGGAAG
CGGCTGTGGAGGgtgagtttttcttcatttttttaagttctaaatcattgcattgcatatttgcatggcctttgttttactcctgaaa
cttttccgattcttcgtatctttttttttttttctttttcccagatgcaagATGTACCCCGACTTTGGCTACATGGAGAAAACCACCA
CGTCCGAGACTCTCATCACCGGTGTTGCACCGGCGAAGCTACAATTGGAGGGTTCTGAGATGAGCGAGGTAGCAGAGAACGGATGCAAG
TGTGGAGACAACTGCAAGTGCGACCCATGCACTTGTAAATGA Catalase ATAATGATATAATAATATTTAAATGATATAAAAAACATATAGAAAACTTGATGTATATATAAAAGTGTGAGGTGAAATAGAGAAGGTAG
AGTTTTAGTAAAATATTTTAAATGATAGAATAGAGAAGTTGTTAAGAGTCCTCTAATAATTGTAAGTGTAATTGTAATTATAAATAATT
CGGTTGTTTCTCTTTAAACCAATTTTCCAAAGAGGCCCTACAAAGAAGTCTTTGATACTATATCCAACGGTTACACTATTTTAGTGTTT
TACACTACATACTAAAAATTTTAACTTTTGTATTGTGGAATGGAATTTTTTTTTCGAAAATACTGTGTAAGTTTTATATTGTGTATAGT
GTTAAATTTTCACAATTGTTTTACGATTGTTTTTTACTTGTTCCATTGTTATTTTAATTGTTTTGTTTTGTTGTTTTACGTTGTTTTAT
AAAAAGACAATATTTTTATAAAAAATTCCATGTGACAATAAAATTGTAAATTTTTATCAAAAATCTATATTTTTATAAAAATCGCTATA
TTTTTTTTTTGAATGATTTAATACAAAAAAAAAAAAAAAATTCATTACACTCTTTCGATTGTCTTTCTGCCTCTCCTCTGTTTTCTCC
TTAATATTTTCTGTCGATCCTTCTTTTTAGCTTGGTATCAGAGCAGGTATGGCATCCCCAGGCGACTCCTCAGTCAACAACGCAAGATC
TCAAGCTGTTGAAGCTCCTCCTCCAGCTCCAGCCCCTGCACCAGCTGCTCAACCTCTACCTGCACCTCTGCTGCAGCCCCTCACGCCTA TCACAATCCGCCTGGACAGAGACAACTACCCATATTGGCGCTAAAAAAAAAAAAAAAAAATACCACACTAGATATGATACGAAACAAAAA
TATCTTTTTTTTAAAAAAAAAATCTCACATTACAAATAAAATTATATTAATAATTTATTATTACTTTTTAAAACAAACTAAAAAAGGTT
AGAAATTACAATAAAAAACGACAATAATAAAAAGTTATATGCAACAATTTAGTCCATAATTTATTTTAGGCTAATAAGGATTTTTGCCC
CCTAAATTTTAACATGTACTAAATTATACCCTTGAACTTTTAAGGTCGTTAAAAATGATCCCTGAACTATTGAGATTGTTGGGTTTAAG
GACTTTTTCCAATTTTAGTAAAAAAGTCTAACATGGATAAAAATTCAAGAGGCATAATTTAATACATGTTAAAATTCGAGGGGCATGAT
TTAGTAGATATCAAAGTATATGAATTATGGTTTAGTACATAAACAATCAGTGAAATAGTACAATTGAATGAAATTAAATAAAATTCTTT
AAATTCAACAATCTAAAATAGTTTAAACGATATTTTTAACTACCTTAAAAGTTAAAGAAGCATGATTTAATACATGTCAAAGTTTAAGG
ACAAAAATCCTAATTAATCTTTATTTTATCTTGTGAAAATTCCACACTAATTTACACACACCCGTTCAAATGTTCATGAGATTGCTATT
GTGGGTGGACCTCTAGTTGTGTAATGTCACTAAATTTTGTATTTTAGAATTTTGGATAACATTATTGATAATAGACATTATTGTGTTT
TCCCCTAAATAATGGAGTAGGGAGTGATTTTTCTTTTTCTTTTTCCTTTTTTTTTACTGTACTCATTATAATGTCAACTTTTACTATTA
ATAGGATAAATGTGAAAATATAATTATTATGTTATTTTTGAAAAGTCTATGGAGGCTTCTTTATAAATACTGGTATTTGAAGTAAGGTT
TCCACACGCTTCAAAACCAAACCTCACTCACTCACTCTTTTTCTCTCTCTAAATCTTGATCCAACCTTTGCTCCATCTTCAAACATGGA
TCCTTACAAGgtattaatattaattatatttctttagttttgttgtaataataataatctaaacccctaatactttagtttgtttattt
aattaaaccaacatcatgatcagcttttcatcttcttctgtatttatttttttaatccaaataaaataaaagaaagagtgagagagaat
atctgatctgagtttattagtcagtttacaaatcttatttaatttgatccatagttaaaatatattattaaagctaaagttggcatac
ataatatatataaactataattacactatatgacactaatttatatacgtaagctgatctgtactaatactagcttgatctagagacta
aaaataaaattattgttattattataataataataaaagtaataattaaaaagaaaaagaaatactagtttatttttgtagtttagattg
aatttattattaatattaattataatttgaagatgatgattatattataagctattaatgaagatttggtgtttggatataaaacagTA
TCGACCATCGAGTGCTTACAACGCACCGTTTATGACTACAAATGCCGGAGCTCCGGTTTACAACAATGAGTCGGCTTTAACTGTCGGAC
CCAGAGgtatttttcggcgaaannnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnttgcaactcgcacctatgcatata
cacatggttatcaaattatagtttttaaaggatttcctacgaaaaaaataaaaaactatacatataaaaattaaaatctaaaaagaga
ttttaccgctaataatttttatacatataaatatttggattttatcaatatatatttatatatatgtctggataactctatctatgt
ccataattaagaagtttggactcattatatgtacacaatctactaaaattacatatagtgacgtttggtttgttttatttactaaat
taaatatataaatatgttttaaaaattatcttatttgaaagccaagatccatcacgttttttttctttacattaaatactcggactat
ctcaatcagatcatgtttttattgtttgataaagaaaatcagattgtatctgctatataaaataaagtttgtacataattattaaat
atatttattaaaatatataaaacccactaatgaaatcatatgccttcttttaaggtgcgtttataactatttatttagacacatattta
aataaattgtacaaaatatttacctacaataattgcatcagtttaatttgtatcaatttatatcaaaaataggtttataactagttct
ggaataccatatatttaattttttttttatttgtatttcaaacaaaaaggaagaaatttaaagcatttagcaaacctaatcagtaaaa
aaagctaaaaacaaacaaaatatcattaaaaaaaatggacaaattaaatctgcaaaaatttttaaactcttatatataatttcctct
tttttaaatttaaatattaatttggcgtggcactcgtggacatgcaatgcaattgagcttgtgatttgtttttttcgatccttcacgcaa
ttaaacgttataaataaaatggaggtgatttaatttggatagttgcagttgataaacatctgtgaataatttactgtagttgatgatta
atcttcgtaattcagatacaagatatgttgatgattttaccgaagaaaaattattgagtctctttaacgtgtttgacaaattaaaggt
gtgaatgaaaatgttgatgttgttgtttgacagGTCCAATCCTGTTGGAGGATTATCATCTGGTGGAGAAGATTGCTAACTTCACCAGG
GAAAGGATGCCAGAGCGTATTGTCCATGCCAGGGGAGCCAGTGCTAAGGGTTTCTTTGAGGTGACTCATGATGTTTCAAACCTCACCTG
TGCTGACTTCCTCCGAGCTCCTGGGGTTCAGACACCTGTCATTGTTCGTTTCTCCACTGTCATCCACGAACGTGGTAGTCCTGAAACTA
TCAGAGACCCTCGTGGTTTTGCAGTCAAGTTTTACACCAGAGAGgtagataataaaaagctttcgagttttacttgtgctctaaatcgt
attccatataacatgttacactgttattactttttcatggttgcagGGTAATTTCGATATTGTGGGAAATAACTTCCCTGTGTTTTTCA
TCCGTGATGGAATCCAATTCCCTGATGTGATCCATGCTTTTAAACCAAACCCCAAGTCTCACATCCAGGAGTATTGGAGGGTGCTTGAC
TTCTTGTCATTCCATCCTGAAAGTATGCTCACCTTTGCCTGGCTATTCGATGATGTGGGTGTTCCACAAGATTACAGGCACATGGAAGG
CTTTGGTGTTCACACCTTTACTTTAGTCAACAAGGCTGGAAAGGTAACTTTTGTCAAGTTCCACTGGAAGCCCACCTGTGGTGTTAAGT
CCATGTTGGAGGAAGAGGCCATTAGGGTTGGAGGAACCAACCACAGCCATGCCACCCAAGATCTTTATGAGTCAATTGCCTCTGGAAAC
TACCCTGAGTGGAAGCTCTACATCCAAACACTTGATCCTGCTGATGAGGACAAGTTTGACTTTGACATACTCGACACAACACAAATCTG

FIG. 10 (continued 1)

GCCAGAGGACCTCATTCCTCTTCACCCAGTTGGTCGTTTGGTTCTCAACAGGAACATTGACAATTTCTTTGCAGAGAATGAACAACTCG
CCATGAACCCTGCCCATACCGTCCCTGGTATCCACTATTCCGATGACAAGATGCTTCAGGCTCGTCTCTTTGCTTACAGTGATACTCAC
AGATACCGTATTGGAGTGAACTACCTTCAACTCCCTGTTAATGCTCCCAAGTGTGCCCACCACAACAATCACTATGATGGTTGCATGAA
TTTCACTCACAGAGATGAGGAGgtaacactcacattattcctccaacaaactcatatactttgcttctttgcttctttgcttattcata
tattatttagttggctctactaatcacatactgtttttctttttcacttctttgttatagATTGACTACTTCCCTTCAAGGTATGATA
CCGTTCGCCATGCTGAAAAGTTCCCCATTCCTGCTAAAATCATCCATGGAAAGCGTGAAAGGgtaattcttccatcaccaaactcaata
tatagtaaaagtaactccttactaatactttggtatatgtgttacttctcttttggtgaatacagTGTACTATTCCAAAGGAGGACAA
CTTTACACAAGCTGGTGTGAGATACCGATCTTGGGCACCAGACAGgtacatgcatatgtggtcatttaccatgtcaaaaacagtattg
aagtgtttggtttcatttgtatgcaattcaccaatgtagattttgactaactttcttcttacattacatctatgcagACAAGACAGGTT
TGTGAAGCGATGGGTGGATGTGTTGGCTGACCACCGTGTCACCCATGAGATCCGCAGCATCTGGATCTCCTACTTGTCTCAGgtcagtt
tccaaccaatctacttctgttaacactgttgaataatgttcatttgctgatgttatgtattggtgtcggtttgtacagGCGGACAAGTC
TCTCGGTCAGAAGGTAGCTTCCCGTCTCAATGTTAGGCCTAACATTTGAGAGTGGACAGCAGGCACGTATGCAAGATGTTTTTAAGATT
CGAAATATGCAAGAAGGAACTAAATGGCGAAAAGTGCAGATTATAAATATGGAATGATGAATAACTCCTGTGTACTATCTTGTGTACTT
TTCTTCTGTAATCTTATGTTTTGTGTTGTTATATTATGTTATGTAACTCTTTATGTACACTATTTATTAAA Asparagine synthetase AATAAAAATATTTAAATATTTGGATAATAAAAATAACATCAATATATTTATCAATTAAAGTTCACTGAAAATTTACCTTTTATTCAAA
AAAAAAAAAAAGAAAAAAGTATAGCTTGCTTTCAGTTTCTACTTTCTAAATAAAATACCTATTTACTTTTAATATTAATGAGTATTTAC
TTTAAATGTTTAATGTGGAAAAGAGGAAAAGTCAATTTCAATAAATGAATATTTATTACAAGTGTCAGATTGTAATAGATTACACAAAA
TTAGACAGTAGATTTAAATCCATTATTCCTTTCTGACCGGATTAGAAAGAAATGTTCAAAAGCTGAGTCAGCATTGTCAAGTAGGGGAA
GTTAATCTTACTTTCATGGAAATGGATAAACCTTACCTTGGTGCATGACCGGGAAACTTGGAGACCCAAGAGAAAATAGAAAGAGCATT
GATACGCCACCTTAAACTACTCCCTACCTTATCCCATAACACATAATATTTTTTTTCTTTTTTTTTTTTAAACGAACACATGATATT
ATTATGTACTCACATTAACTCACACATGATAATTAAATATAATTATCTTATAGAGTATTCTACACTATAAATGGCAATTATCAAATAG
AAAAATTTATTATTTGAGTATTACTATGACATACTCTAAACCACTGAACACCTTAATTAAAACATTAATAAAATTTACATAAACCAAAT
TTTTTTAAAAAAATATTATAAAAATTCATCAACGAAACATGATCATTGTTTTTTACTTTCTCTCTCTTTCTTTTCACCCGNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNTAATATAATAATTTTA
AGAAGTATTATTAACTAAGAGAAGTTTAAAGATGCTAGACACAAGTAGTTTCTTAGCTCTATAAAATAAGATGTTAGCATTTTCTATTA FIG. 10 (continued 2)

TTATTTAAATGTATATTATTAAATAAATAAAAAAGAGAGAGGTGAAGAGAACAAACCATGTGAGAACACGTGGCAAAAACGGAGAGGAG
AAGAGAGGGTGTGGGGCAGGATGGGGTTGTAAACATTGGTAGTGACGACGCCGTTTGATGGTCACACTACCACTATAAATACGTGGCT
TGAGATGGGGAGTTTATTACTATAATCTTCATATTCCAACTCCTTCCCTCCCCCACTCATAATATACGTGTTGCTCTTCTCCCTTATTT
CCACTCCTGCCACCTTTGTCTTCTTCTATATCCATAACCAAAAATTTTCAATTCAAAATGTGTGGAATACTTGCTGTTCTTGGTTGCTC
CGATGACACTCAGGCCAAACGGTTCCGTGTTCTTGAGCTTTCACGCAGgcaattaccattcctttatattaacttgatttgtttcattt
ctttctatagagaccgagaaaaaatccattactttgtggttgggcgtgtgtgtgcgtcagattcaaaatctagttaaacaaacggt
ttgaagccctttttcctatttatttcccaagatcggctttcctttttttctttcctttttttttttttttatctcattcgcttaatac
tttttccaattttatcttagaatttagataaagtgggattaaagtatatgaaattctatttcaaaattaattgttaataggaagaata
atttatttatcttatatatnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnacttgtacttccataaggcatatatcatggtcccgcactagagttacttctagctaagaccaaaatatatat
gtcattaccattcaaataaaacacacgattatatcaatcatggtagtattagtatacactaatttaaaatttcggatcgaagagctagt
ttatagggaatcccaaagtgaataattggaattaaaatagaattgtgtcattatccaattctttctctaattttgattaagataaagca
tgtggggagtggggtccattaatgaaagtgtggtttagaactacttgtacaatttgattttgtcgttaagatttaactgatagggcctt
ctactactacgtacctacctggaccaggatttggagtctaggcgtccgtacgtgcaaaacagtagtaatataaagaacagaattaatga
gtggtagtactgactataattacactgttgtaatgtgtaccatacagATTGAAGCACCGTGGTCCAGACTGGAGTGGTCTATACCAGCA
CGGTGACTGTTACTTAGCTCATCAAAGGCTAGCCATCATTGACCCTGCTTCTGGGGACCAACCCCTCTTCAATGAAGACAAATCTGTTG
TTGTTACAgtaagtccatcatatcttccaaccttgttatttaaaatgtttgatttatgaatattaatatggtgtctgaaaaaaccagG
TGAATGGAGAAATCTATAACCATGAGGAACTCAGGAGCCGTCTCCCCAACCACAAGTTCAGAACCGGAAGTGATTGTGATGTTATTGCT
CATTTGgtcagtaggcagtCTAAAAATTTTGTTACTAAATTTCCCACACAAATTATTAGATTGATTTTTTGAAAAAAATTCTTTTATCT
TATGTAGTATGAGGAGTTTGGGGAAGATTTCGTTGACATGCTTGATGGGATTTTCGCTTTCGTGTTGCTGGACACCCGAGACAACAGCT
TCATTGCTGCTCGTGATGCTATTGGAGTTACTCCTCTCTATATTGGATGGGGACTAGATGgtattagttttagtatatttactctgttt
tacatggtgaaacttatgtttctttttctatgtttggtaagtgaggatgaaatgaatgatcgttgtgttttgaattttgtattcagGAT
CCATTTGGATATCATCTGAGATGAAGGGCTTAAATGATGACTGTGAACATTTTGAGGTCTTTCCTCCGGGTCATTTGTACTCAAGCAAA
CAAGGTGGATTCAGGCGTTGGTACAACCCACCATGGTTCTCTGAGGCTGTTCCATCAACCCCATATGATCCACTTGTTCTTAGAAAGGC
TTTTGAGGATgtaagattctagtcaattctgatttatttagaattaagtcaacttcgtttttgttttgacaaaataacttatgtattg
aaacataacacatgcagGCTGTTATCAAAAGGTTGATGACAGATGTGCCTTTTGGTGTTCTACTCTCTGGTGGCTTGGATTCATCGTTA
GTCGCCTCCATCACTGCTAGACACTTAGCAGGCACCAAAGCTGCCAAGCAATGGGGAACACAGCTCCATTCTTTCTGCGTTGGTTTAGA
Ggtaaattacttattcaaaaggactcaacatcacatgcctactttttctttattttgtacttggtattaagatcttcaacctttacaat
tgtgagcagGGTTCCCCCGATTTAAAGGCTGGAAGAGAAGTTGCAGACTATTTGGGGACAGTTCACCATGAGTTCCACTTTACCGTTCA
Ggtaataacaataacaacctctattatgttgcttaatagataactaacatactatatttattttaatatgtaaacaattttgcgatttg
tgtgtaccgcagGATGGAATAGATGCAATTGAGGATGTGATTTTTCACATTGAAACTTATGATGTTACCACAATTCGTGCTGCTACACC
GATGTTTCTTATGTCCAGGAAGATCAAATCTTTAGGTGTTAAAATGGTGATATCTGGGGAAGGCTCTGATGAGATCTTTGGTGGCTACT
TGTACTTCCATAAGGCACCAAACAAGGAAGAGTTTCACCAAGAGACCTGCAGAAAGgtacttggtttttcttcatttggcctgctata
tgtggcttaactacgtgtgtgtgtttatgaaagatcaatgactttattactctttacctttcagattaaggcactgtgtttatgaaaga FIG. 10 (continued 3)

tcaatgactttattactctttacctttcagATTAAGGCACTGCATCAGTATGACTGCTTGAGGGCAAACAAAGCAACATCAGCCTGGGG
TTTGGAAGCCAGAGTCCCATTCCTAGACAAAGCATTTATCAACACTGCAATGGCTATTGATCCTGAGGCTAAAATGgtaacatagtttg
ctttgtttggttttaagatgcctttagtttgattatttttaacatggtcaaactacagaggccaatgttaatcaacctgtattgaatt
tcagATACACCCAGAAGAAGGAAGAATTGAAAAGTGGGTGCTTAGAAGGGCCTTTGATGATGAGAAGCAACCCTATCTGCCAAAGgtga
aactcttttcccaacttgtattatcagatgccttcttatataacttcttatttccccctttctaactattgtttctatgtgattcct
tgcagCATATCCTGTACAGGCAAAAAGAACAGTTTAGTGATGGAGTTGGATATAGCTGGATTGATGGCCTTAAAGATCATGCTGCTAAA
CATgtagaatagcctctttaacttgtttattcacttgtcattttgaaaatgaaaccactattatcttggaaactcacttgaaatctt
atcattcttgctcatttgtactcacagGTAACTGACAAGGTGATGCAAAATGCTGGAAATATCTTCCCACACAACACTCCCACCACAAA
AGAAGCATACTACTACCGAACCATTTTCGAAAGGTTCTTCCCACAGgtaaaaataacacaaagattaacttaacttgtgcttctgtcat
tatgctcttctgtattaacttgtgctattggattttgcagAACTCAGCTCGGCTGACTGTACCAGGGGGAGCAAGTGTTGCCTGCAGC
ACAGCGAAAGCCGTTGAGTGGGACGCTTCATGGTCTAAAAATCTCGATCCATCTGGCAGGGCCGCCCTTGGAGTCCATGTTTCTGCTTA
TGACAACTCTTCTGCTAATAGTGGGGTGGTTCAACCTGTGATCATTAACGATGTACCACATATTTCAGTGAGCACTCATGGTGTTGAGA
TCCTCAGCTAGTAAAATCTTACACATAATGATGCTAGATGGAATAATACTACTACTAATAATAATAATGATTTGTAAGTCTACTGAGGC
TAGAATTTAAGATGAGTTCTTTCCTTCCTCTGCCTTGACTTGGCATATATTATCGTATAGGCAGTATGTAAAAATTTGAGAGAGTAGTA
CTCTCTCTGTGCTATGGTGACTTGAAATATATATGTTATCCTTGTATTGGTGTTCATAATATAAGAAGTGACACTTTCTTTTGCTTTGG
GTACA 60S ribosomal protein L3

ATAATTTCTTTTCGTCATGAATGTAATATTTATTCTCTAGTAATGTAATATTTATGTTATTGTAATATGATATTTTAATTTATTGAGTT
TCGCCGATTTTACAGTATTATTATCTTTAATCTAATTAATAAGTTTATTTAAATTATTAGTTAAATATAACAATTGTGATAATTTTTT
AATTAATATAATATATTTTTTATTTTATTAAAAAATTAATATAATAATAAGGAATATTATTTAGTTTAATTTTTAGTACTATGGTTATA
GTAGAAATATTTTTTGACGCAAAATTTGGTGATAGTAATACCATATTTAGCTTATCCTTAGAGATGCTCTTAGTAAAATTTTAGTAATT
GAATAAAGGTTAATTAAGATTTTTGCCCCTTGAACTATGACATGTACTAAATCATGCCCTCTGAACTTTTCAAGTCGTTAAAAATTCCC
CATGAACTATTGAAATTGTTAGATTTAAGGACTTATGTCCATTTTTATTCAATTTTGCTAATGTGAAAATTGTCCATGTACTAAATTAT
ACCTCTCTAACTTTAATATCTACTAAATCATGCCCTCTGAACCTTAACATGTACCAAATTGTGCCCCTAAATTTTTATCCACGTCAGAC
GTTTTTTTAGTAAAATTAGACAAAAGTCCTTAAATCCAATAATTTCAATAGTTCATGGAGAATTTTTAACGACCTGAAAAGTTCAGGGG
TAAAAATCCAAATTAGCCTATACCAAATCATGCTCCTCGAACTTTGACATGTACTAAATCATGCCCTTGAACTTTCATCCATATGAGAC
TTTTTTACTAAAATCGGACAAAAGTCCTTAAATTCAACAATCTCAATAGTTCGGGGCAAAAATTCTAATTAGCCTTGAATAAATGTTAT
ATTTTCTATGATTTTATATAAAAAAAATAAGGGTAAATAGCGGCAAAAGTACCCAAAGTTTTATGTTTGTAAGCGGCATAAGCCCAATG
TTTATTTTTAGCGGCATAAGTACCCAATATTTGTAAAACTGCAATTTTTCTCTAAATTTATCAGTACAAACTCTGTCATTGTCTTAAAC
AAAGCACATATAAGGCCTAAATTCTTTTTTTTTTTTTTTTTTTTTTTTTGTAGGGTAACCGATACAGGTTAAAATAACAAAGGTAAC
AAAGTTACACAACCAGAGGAGAATTTTCTTCCATCTATAATAGTTTATTGTCTATCCTAAGAGCATGCAGAGATACCCTAGGAGAGCTA
GACAATAAAACCATAATATCAGAAAAGAAAACCTCAAAACTGAGAGTTGTCACTTCCGAACCACTAGTAAAACACCTGCAAAATAAAGA
GAAATTAATTAATACATAATAAATATTTAATAAAAAAATGAAATTTCCCTTATAAATAAAATAAAATAAAATATGAAATTTTATATAAA
TAGTCACATAGAATTCTCTGACGTAGATACTTATATGAAATTTTATATGAAATTTTATATGTAGTATGAGTTACTTCCAAATGTTCTCT
TAATAAATTTAAAACAGAGTCTGTACTGACAAAACTGTAAGAAAATTATAGTTTTACAAACATTAGGTACTTATAACGCTAAAAATAAA
ATTTTGGGTATTTATGCTACTATTTACCAAAAAAAATAATAATAAAAAAAGTTTATATTTTCTCTAAAAATATAGAATGGGGGGAGTGT
AAGAAACATAAACCTAACAAATAGGCTGAAATGGAAAAGAAGAAGGCCCATATTGAGATATGAGAATGGGGGCTATACTTAATTTAAGC
TAAATATAGGATCTGTCTGCAAAATAAGTACTATAAAAACATATCTAGGGTTTTAGTCGTAACCCTTCAGTCTGGTGTGCTAGTTCAGC

FIG. 10 (continued 4)

TCTACCTTCGCCGCACGAGAAGCTCAGGTTTCCTTCCCTTTTCTCTCTTCTCTGTCTCTGCTTCGTATGTGTTTTTCTCTAAGATAACG
AAAATGGAAATGAACTTCTTTCTGTTCATTCTCCTACATTTTGTGATGATACACACTGTGTTTTAGCAACATTTCTTGTACTCTCGTTA
GTTTGTGTTAGTTCATATTAGATCTGGATTCATGGGTTTTCATTAGATTGTTTTATATGTTTGAGGATAAGAAAATAATGGGTTTTGAT
TCTTTTGTTGCATTTCTGTTTTAGCACTTAAAATTTAGAGCTTTTTTGTTTAACTTTTAATTTGATTATATTCTTATGAAACTATATTT
GTTATTGCCAGTAGGAAGAAGAGAATGTCTCACAGGAAGTTTGAGCACCCCAGACATGGTTCTCTTGGATTTCTTCCAAGGAAGAGAGC
TGCCCGTCACAGAGGAAAGGgtaagttatttcttgtgtatttagtatttacttttgatttttttattacatatacataaatgattga
atagatttagtttgttcaaatgtttaaattctcatttcaatttatgtatgataaatttagattagttctattgataaatagttcattt
aaacgttgttctggattgtatactattacattgtttcattgggttttagaatctaatagcctttgttatatttgtatttgtgcagT
GAAGGCTTTCCCCAAGGATGACCCAGCTAAGCCCTGCAAGTTGACTGCCTTTTTGGGATACAAGGCTGGCATGACCCACATTGTTAGGG
AGGTGGAGAAGCCTGGATCAAgtaattgactttcaaatgatttaatttttttcttaaacttgtttcatttgtctttttgtcttatgaat
tttgttttaatttggttagAGCTTCACAAAAAGGAGACATGTGAAGCTGTGACTATTGTTGAGACACCCCCAATGGTTATTGTTGGTG
TTGTTGGTTACGTGAAGACTCCACGTGGTCTTCGTACCCTGAACACCGTCTGGGCTCAGCATCTGAGCGAGGAGGTGAAGAGGAGGTTC
TACAAGAACTGGTGCAAGTCCAAGAAGAAGGCCTTCACCAAGTACTCCAAGCAATACGAAAACGAAGAAGGAAAGAAAAGCATTCAAGC
TCAGCTTGAGAAGATGAAGAAGTATGCTACTATCATTCGAGTTTTGGCTCACACTCAGgtactttcacaatctctgttattgtgctgtt
gtgatttacttttttcatttgaatctctggtgatgtatctgttttgctgtgtatattcagATCAGGAAAATGAAGGGTTTGAAGCAG
AAGAAGGCTCACCTTATGGAGATTCAGGTCAATGGTGGTTCCATTGCCCAGAAGGTGGACTTTGCTTATGGTTTCTTCGAGAAGCAAGT
CCCTATTGATGCTGTCTTCCAGAAGGATGAGATGGTTGACATCATTGGTGTGACCAAGGGTAAGGGTTACGAAGGTGTTGTTACCAGGT
GGGGAGTTACCCGTCTTCCTCGTAAGACTCACAGGGGTCTTAGGAAGGTTGCTTGTATTGGTGCCTGGCATCCAGCCAGAGTGTCCTTC
ACAGTTGCTAGGGCTGGACAGAATGGATACCATCACCGTACCGAGATGAACAAGAAGATCTACAAGCTCGGCAAGGTTGGACAGGAGTC
CCACACTGCTTCCACTGAGTTTGACAGgttagtaaaatgactgattatttataattcgacaggagtcccacactgcttccactgagttt
gacaggttggtaaaatgactgattatttatagtttgaacaagggattgaattggctttctatttcgtcgttagacaattctaacttaat
tttttatatttaggaccgagaagGACATCACTCCCATCGGTGGGTTCCCTCATTATGGTGTGGTGAAGGATGACTATCTGATGATCAA
GGGAGGATGTgttggacattagaatttacctttaaaatcgtcgcatttatttatttatttgcaataaaggtgaaaaggtgatacttacc
atatttgtgaaagAATTTTGGGCTATCAAAGTAAAACTAGGAAAGTTTCAGTTTTTATGCTTGTGAGATTATGTGGAGACAGTTTTGAT
TTAGTTTTTATGTATTTTGAATATTTAATACTGCCTTTGATGCATGTGAGAATCTATTGGTTTTCGTCAGAATTAATATAATCAATTTT
CTTTTTAGTTTATTTGCTTATGTCTTGTTGGATA

40S ribosomal protein S3a

ACTTTGTTTTTAATTTTGCAGTTTCTTTTGGATGATTAAATGTTCTCTAGAATCTCAGACTCTTGTATTGCTTGCTCAAATACCTTAAA
AGTAATATTTTCTTTTTTGCCATTTTCAATATGATTTTGAAGCAAGGATTGTTTTGATGATATTAAACGCCCAATATGATAGAGGGTT
CTGAAATTTTAAAATACTTTTCAGCTAAAATTCACCAAGTAAAATTCTTACATCAAACACCCGACCCAAGAGTCTTTTTAACCATAAAT
TACCTTATTTCAAGTCTGTTATCTTAGTACACTGTAATTTTCGTTTAGTGTTGTTTGTTTTGTGTCGTGTTCACAGATTTGAGATGTTT
TTTTGTAGCAAATAACTATACGTTTAAAGCACATTGCATCATCAACTCATATAAACTAAAGAAAATCAACACTAATAATTCATCTCTAG
TAATGATATTAATCATTATATATATATTCTATGTTGTGTCTGGTGTGATTGTCTTAATTTCCAAGTTCTAACTTGTTATTTCCAAGTTC
AAGACTTAATATATCATCTTATTTGCAAATAATGACTCGTATTGCTAACAGGAAATAGATGTGTTTAGAGAATTTCTATTATATATAAA
AACAAAAAAAATCTACAAAGTATACACGTACAATCAATCGTCTAAGAAGTTGAACATAGTTGCAAAAACGTTACAGAACTCATAAATCT
CTTAACAGGCTATTATTGACTAAATAAAATGGTAACAATGAGAATAACCAAATTTCTTTGGCAATATTTAGATAGTTTCCTTTCAAAA
AGATAAAAAAACACACAAAAGAGGACCTCGTTGTTCCTAACCAGCTAATCAATCTGGAAAAGCCTCCAAAACGCACCCCTTGGCTTGGA
TACTCATGCAGGAAAGGAATACCTAAAGGAAGCTCATCTCATATATGAGAATCCACCATAATCGGAAGCTCTCACTCAATGGTAAGCTA
AAGGGAAGGCTCTCCACTTACCCCAAAGGAGAAAATTACACTCTATACCTTTTTTATATTGTCCTTTTTTATTTTTACCATCTTTTTTA
AAATCTATCATTTTTTACCTCTTTTTTAAATATTGTACCAATTTTGCCCTTGTCACTTCAAGATACTCTCCATGTGACTCTCTTATATCA
GGGTATTTTGGGTACAATACATATAAAAAGAGGTATGTTTCAAATAAATATAAAATTAGAGGCAAATTTGATTAATTGATTAATAAAAT

FIG. 10 (continued 5)

GGGTATTTTTCAACTTACCCCTTATTAAAGAGCCTCTGAGCTACGTGCCTAGAAAATGGAGCCCATCAATTGGAGAAACAAATAAGAGC
ATCTCCACTAATGATTTATATTTAAGAAATGCTTACTAGATTATTTATTTAGCAAAATATAAGGATGCTATGTTATTGGAGATAAATTA
GTACTATCATAGAAAATTATGTTGATGCCATTAAAGGTAAAATAGTGTGACAATATTTATAATTAAAATAAATAATATATTAAATAATA
ATGTGAGAGATTATAATTATAGCATTCTTGAAAGGTGTTATATTATTACAGTATTTTTAAAAGTTTATATTTTTGGATAAATATTATCA
GATTGACAATAAAAAAAATAATCCATAAAAATCAATATTATGACTTTTGGGTATTTACGAAGTAATTTAAAAAAAAGGATATTCATTGA
TCAAAAATACTTTTATATTATATATTTTTTTGAGTGGGTTGTCTAATATACTTTTAATCTCTACTTAAGCCTAGCTTATAATTTACAAT
AACTTAAGGAGTTTAATGATGACATTATCTATAAAAGTAGGTACATTTTAAAAAATATGAAAATAGAAGTAAAAATTAAAACAAATAAA
TTAAAATGGGTGCAATGTAATTTTCTAAAAAAAAAAATAAAAGGCCAATTTTATATTTTTATAAAAAGAATATGGGCTTTCAGCAAAAT
GAGCGCAAAAATAGAGGACTAGGCAGGCCCGTGTAAAGCCCAATAAGAAATATATATATTATAAGAAACAGAAGCGAGTTGCGCCTCTC
AGACTGAAACCCTAGCTAAGCTCTACTCTCTCCTCTCTTCTGCAACCATGGCCGTCGGgtacctcttctctatttctttcctccgctat
atgcttcattcatgtacttctgaatcatggatttctgtatgtttatttctttcttttctattttcataacatgcatgtgatctgatttt
ttagGAAGAACAAGAGGATTTCCAAGGGTAAGAAGGGAGGCAAGAAGAAGGCgtaagtcaattttcaacttttatcttttattcagatt
tgatttgagaatcaaaatctctataattgcattaacactttgttaataatataatacagAGCCGATCCCTTTGCCAAGAAGGATTGGTA
TGACATCAAGGCTCCTTCTCTATTCAACCAAAGACAAGTTGGCAAAACCCTTGTCACTAGAACTCAGGGAACCAAGgtttgtctcctca
aaatgctttcttttatcattataattattaagcttaggtgctcatgatgatttattgtttgttagttaagagcctaataagggattatt
attcctttttttgaatgtcaagctctatttggggaaatgtggttgataatttaaacttataatgatgatgatgattaagcattaggac
tatacttttctctagtattttttttttcatcagtagcaattgttagtttagttgaacttatatgtaagtgtatatttggattggagat
gagctgttatgttgtttcattaatatgcccaattgtgtgtgaggatatacttcatgtttctttgtatatttcatgtatttagaggcgc
attgatgtttaatttgttattatgttatcagATTGCTTCTGAAGGTCTAAAACACAGAGTGTTTGAGGTTTCCTTGGCTGATCTCCAGA
AGGATGAGGATCATGCTTACAGGAAAATCCGTTTGAGAGCTGAAGATGTTCAAGGGAAGAATGTTCTAACTAACTTCTGGgtaggtttc
tttttaatgaatttcattcatctatttggaacttcttttgtacaatgtttacttatttaattttataatgcgaatttgcagGGAA
TGGACTTCACCACCGATAAGTTGAGGTCACTTGTTCGCAAGTGGCAAACACTTATTGAGGCTCATGTAGATGTCAAGACCACTGACAAC
TACACCCTCAGGATGTTCTGCATTGCTTTCACAAAGAGACGTGCTAACCAGGTCAAGAGAACCTGCTACGCGCAATCCAGCCAGATTCG
TCAGgttcgatttgatttgattgtctctttctcttaaatgctccacatttcatttagtatgctatgctttgatgacatatagaaactt
gtgttaacaatctttgtttgcttatgtttaatttccttttcatagATTAGGAGAAAGATGAGAGAAATTATGATCAACCAGGCCACG
TCCTGTGATCTTAAGGATTTGGTGAACAAGTTTATTCCCGAAATGATTGGTAGAGAGATTGAGAAGGCAACATCAAGCATCTACCCACT
CCAGAATGTCTTCATCCGCAAAGTGAAGATCCTTAAAGCTCCCAAATTCGATCTTGGGAAGTTGATGGAGgtattcattggcattggat
tccattcttaacaccccttttaactcgtaggaaccttagattgtttttttgattttgtcgaattgtttgtgtagGTTCACGGTGATTA
CTCCGAGGATGTTGGAGTGAAGGTTGACAGGCCAGCTGATGAAACAGCGGTCGAGGGTGAGGTGACCGAGGTTGTGGGAGCATAATGAA
ACTCAAATTTTCTTTTTCATTTTGTTAAAATCAGTAACATTTAAGGTCTTTTCAATTTTGCGGATTTGTGTTTGACAGAGTAGAATTTG
TATGGATGGAATTTTGCTCTAATTAGACTTATGGCAGAAGAACAACAAACAAATACTGCTTAGAAAATTTTATCAGACATGTCATGTAT
TATCTTTGCTTCTTTTTTTATCATCTTATTTATAGATTCCTTACATGTTTGATTGATTTCTTCGAA Phi-1 protein TATGTTAGCAATTAGTGATACGGTTTATGGATAATAATCAATATTATAATGCCGCAGTAGTTTTTTTATTGATTAAAGTCTACTCTATT
TAATAAGTTCAAAAGGAAATGCATGCATCATTTCTTGGTACCTATTACATGAATCTAGCTCATAAATGTAATATACAAAATATAGTAAT
TTATGATGTATAAATTAAACTACATAGCCAATCAAGAAGTTTTGGTATTGCATGGTAGCTATTTATGAGGAAGAAACTTAATTATATTT
TCTTCTTTTCTAGATAAGGCAAAAGGTAGGCTTCTTTAATCTTAGATGAGTCTCAATGTAACGTTTGTTCTTTTATAGCTTCAACTGT
CCAAATATGGGCAAACCCTTCCTAAAAATGTATACATATTTTTATTAATTACAATATATATATATTTGTAATTACAGCTAATATATATT FIG. 10 (continued 6)

TACTATCGAAGTGTTATATATCTTTGAACTATTATCTTTGATTTAATAGTTATGCTAACTTACACCTAGAGGTGAGAAGTTCAAATATT
CCAACAAGAACATTTTTATTTCTTAATTATAAAGTTTACTTTTCAAAAAATGTAGCTTTAGAATTTAAACCCCTATATTTAATACATT
AACTATTGAAGAATTTTCTTTAAAGAAAAGTTACACAAAGTACTTAAGATTGTACTTGTTTTTTTTTTTTTTTTTAATGTTTTTAAGGA
TTTTTTCCTTTTTTTTTTTTTTTTACATTTTTACATACTGTATTTTTCAAAGAGAAAACAAAATATGTTGTTGTTATGCTGTGCAACGT
TATATTATATTCTCTTAATGTGAAAATAATATTTTTTTTTAGAACAACCTAAAAATAACAATTTATAAAAAAAAAAGTTTGTAAAAAA
TAATATTCTCTTATAATGTAATTTTTTTTTTTATTATTTATGGAGTATTATCAAGTAATTTCATATTTTTATGGTTACTTTTCATTTTAC
TTTGTATTATATTTACTACTATAAAAAAAAAATACAAGTATATATAAATATCACGTAGAAAAAAAATTATGTTCTCTGTCTTACAAAAA
AAGATATTTTTTTTTTTGAACTTTAAATTCTAAATCCGCATTTCAACATTTATTAGAGTTGGTTATATTTGAAATGAACATGACATT
TCTCGTATATCTGTATGTATGTATACAATGAAGAAAGTCACACTTCCAAAGTATGGCTGTTTGACAATGGTAGATAAATAATAACATCT
AAACTAATTAATGCTTCTTTAATGACCTGAACAATCCTAATTATACTTAAATCTCAATTAGAGAATTACTCAAGATTATTTAAATTACA
AATTAGAACACACAGCTGATGAACATCTCATAATAATCTTACGTGTAATTCCTTTTAAAGAATAAAAAATACATCTACATCATATTCAT
ATGCAAGTTGAAGGGAGAAAATTACAGGTCAAGCTATACAAACAAATAATACCCTTCGCCACATAATACATAACTTAGTATGTATTTAT
CCCCAAAACCAAACTAGAGGTTAGATATTATTTATTGAAATCATGAAAAGAGAAAATAATAGTACTTGTTTAAAGGCTGATGACAAAG
AGTTAGCTAAATATTTTTTTGTCATTTTCCTTCTCGTTGGCTGTCATGTTTGTCATAATATCTCTTCTTAGCTGGCTCTAGTCTTTAGT
CTGTAGATGAAGTCATTAGTAGATTTGGTGGAAACTTAAAAGTGGTATTATTATATGTAATAGCTGTGCCTAAAGATTTTAATCTTCTA
TCAACGCGCTTTCTTGCTGGCATTTCACTCTCTCCCTCTTAGCTACTTATTCATTTCTTTTTCTTTCTTTATCAATACGTTATATTAATT
AGCTTTCCACTACTGATGAATTAGCTAAACCTAAGCTCCTTCCGAGTAGTTGCTTTAGTTAGCCCACTAATCACCAAATTAACATACTC
ACATTATGTATATAAATACACCATTTTCCCTTGTCTTCTAAACTCACACAAAACAAAGCATAATTTAAGAGTCTCTTCTTTTCTCTAAG
CTCAGTATAATTAAAAATGGCATCTTTCGCCTCAGAAACTCTCACTTTCATCTTCTTCATCTCTCTACTCCATTTGGGTTCATCGGGGA
GGATTCTTTCCGACGAGTCTGACCAAACCCAACAGCCTCTTCCCTTTCAATACCATAATGGCCCTCTTCTGTTTGGAAAAATCTCCATT
AACTTAATATGGTACGGAAACTTCAAACCAATCCAACGAGCCATTGTCTCCGACTTCATTACCTCCCTCACTTCATCTTCTAAAACCAA
CACAGACCAACCATCAGTCAACACGTGGTGGAAGACCATCGAAAGCTACCAATACCACCACAAGATGAGCAACTCCGTCTCGTTAGGAT
CCCAGTTCATCGACGAGAACTACTCCCTGGGGAAATCGTTGACCAGTCAACAAATAGTGGGACTCTCCAGCAAGGGCGGCCAAAAGGAC
GCCATCAACGTTGTTCTGACTGCGGCTGATGTGGCGGTGGAAGGGTTCTGCTCTAGTAAGTGTGGAACACACGGTGTGTCATCTGGGTC
GGGACCCGGTAGTAAGAGGTCCAAGTTCGGTTACATATGGGTGGGAAACTCGGAGAGTCAGTGCCCAGGTCAATGCGCATGGCCTTTCC
ACCAGCCAATTTACGGACCACAAACACAGCCACTGATTGCCCCAAACAACGACGTGGGTTTGGACGGAATGATCATCAACGTGGCTAGC
CTTTTGGCTGGAACCGTAACGAACCCGTTCGGAAATGGGTACTTCCAAGGGCCGAAGGAGGCTCCACTTGAGGCGGCTTCGGCTTGTAG
CGGTACTTTTGGGAAGGGGGCGTATCCTGGATACCCTGGTCAACTCTTGGTTGACCCCACCACTGGTGCAAGCTACAATGCTCACGGTG
ACAATGGCAGGAAATACTTGCTTCCTGCTCTGTTTGACCCTTCCACCTCCACTTGTTCTACCTTGGTTTGAACATACATAATTAAATTA
CACACTGTATAAATATATATCTAGAGAGAGAGCATTGATTTTTTTTTTTTAATTCTTTTTATTATTATTCGACTATTCATCATGTATAC
TTGTTATACCACCATTATAATAAACTATTGGTATTATTCTTTATATATACGATTTTTTAATCAA

Eukaryotic translation initiation factor 5A-4

AGTGAACTGACAAATCAGGGAATAAACTTTCGAACATATAATTAAGATTATATTCCACTGTGTTGACAACACTATAATCATTAACAATTGATATGTTCTGG
ACTTAAATAGAATTCATACATTATGTACATATAATCATGAAATAAATCATGTGAACCATGCAACATTAAATGTTATTTATGATCTATATTAATAAGTAAATC
TAATTATATTGAAATGAGTTTTATTTAGGGCATAAAACCCAACATTTTCCAATTGTAATTGGGGGCAAAGATAAAAAGAAGTGCACAAATCTGGCACATATT
CTCACTGAAAGAAGAGAGTTCACACAAACAAAGCAGACTACCAAAAGTCGCTAGAGGGAGAAACCATGCAAGCCAACAAGCAACACTAACCAAAAGAAAGAT
CTAATCGGGCACTGAGCTACACACAATCCCCTCCACAACCACACAAACAAGCCTATGAGCACGACAAAACAAGACCACAGCTGAACCAGAAACAAGCTCCGA

FIG. 10 (continued 7)

Figure 10:
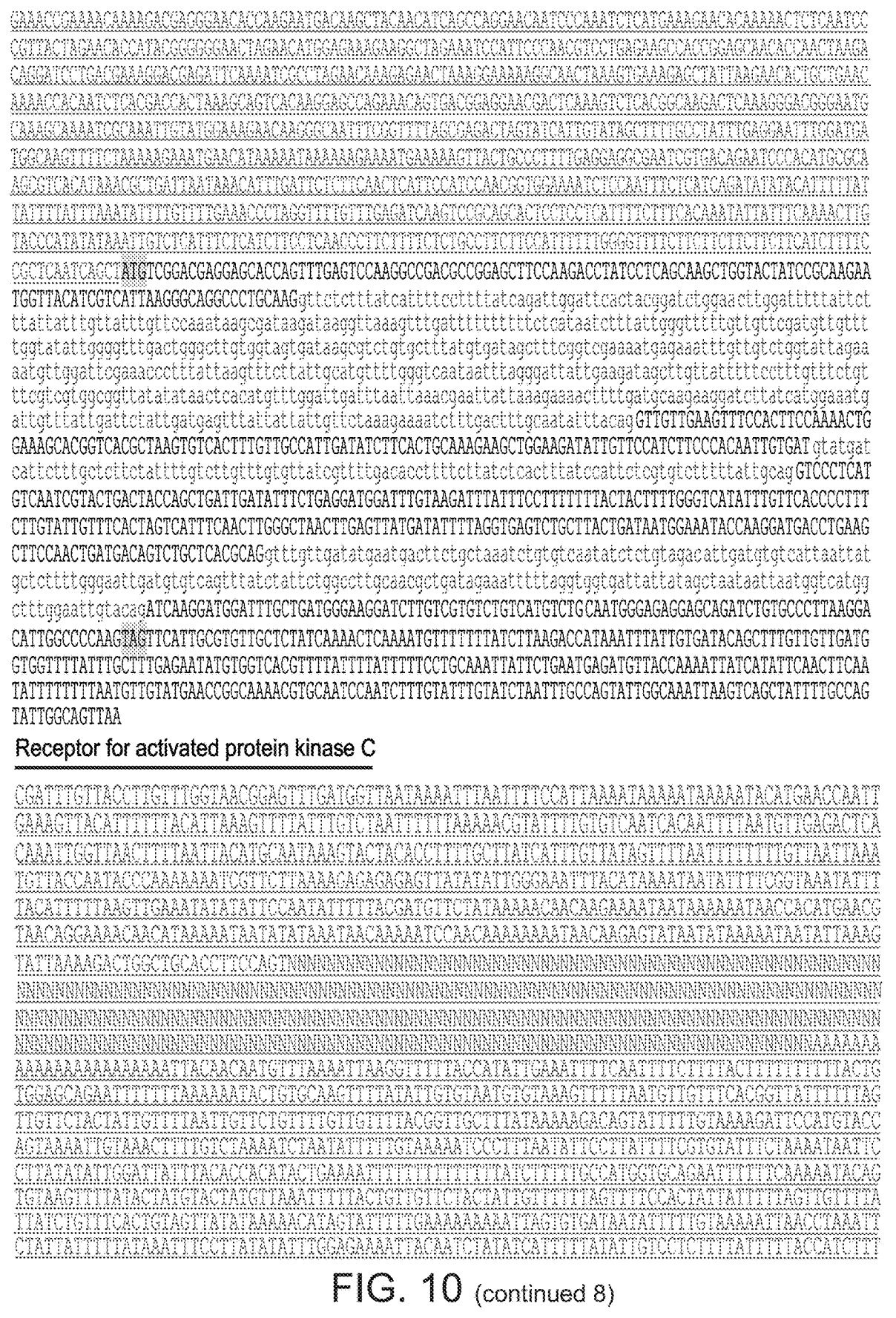

GAAACCGAAAACAAAAGACGAGGGAACACCAAGAATGACAAGCTACAACATCAGCCAGGAACAATCCCAAATCTCATGAAAGAACACAAAAACTCTCAATCC
CGTTACTAGAACACCATACGGGGGAACTAGAACATGGAGAAAGAAGGCTAGAAATCCATTCCCAACGTCCTGAGAAGCCACCGGAGCAACACCAACTAAGA
CAGGATCCTGACGAAAGGACGAGATTCAAAATCGCCTAGAACAAAGAGAACTAAAGGAAAAAGGCAACTAAAGTGAAAGAGCTATTAAGAACACTGCTGAAC
AAAACCACAATCTCACGACCACTAAAGCAGTCACAAGGAGCCAGAAACAGTGACGGAGGAACGACTCAAAGTCTCACGGCAAGACTCAAAGGGACGGGAATG
CAAAGCAAAATCGCAAATTGTATGGAAAGAACAAGGGCAATTTCGGTTTTAGCCGAGACTAGTATCATTGTATAGCTTTTGCCTATTTGAGGAATTTGGATGA
TGGCAAGTTTTCTAAAAAGAAATGAACATAAAAATAAAAAAGAAAATGAAAAAGTTACTGCCCTTTTGAGGAGGCGAATCGTGACAGAATCCCACATGCGCA
AGCGTCACATAAACGCTGATTAATAAACATTTGATTCTCTTCAACTCATTCCATCCAACGGTGGAAAATCTCCAATTTCTCATCAGATATATACATTTTTAT
TATTTTATTTAAATATTTTGTTTTGAAACCCTAGGTTTTGTTTGAGATCAAGTCCGCAGCACTCCTCCTCATTTTCTTTCACAAATATTATTTCAAAACTTG
TACCCATATATAAATTGTCTCATTTCTCATCTTCCTCAACCCTTCTTTTCTCTGCCTTCTTCCATTTTTTGGGGTTTTCTTCTTCTTCTTCTTCATCTTTTC
CGCTCAATCAGCTATGTCGGACGAGGAGCACCAGTTTGAGTCCAAGGCCGACGCCGGAGCTTCCAAGACCTATCCTCAGCAAGCTGGTACTATCCGCAAGAA
TGGTTACATCGTCATTAAGGGCAGGCCCTGCAAGgttctctttatcatttcctttatcagattggattcactacggatctggaacttggatttttattct
ttattatttgttatttgttccaaataagcgataagataaggttaaagtttgatttttttttctcataatcttattgggtttttgttgttcgatgttgttt
tggtatattggggtttgactgggcttgtggtagtgataagcgtctgtgctttatgtgatagctttcggtcgaaaatgagaaatttgttgtctggtattagaa
aatgttggattcgaaacccttattaagtttcttattgcatgttttgggtcaataatttagggattattgaagatagcttgttatttttcctttgtttctgt
ttcgtcgtggcggttatatataactcacatgtttggattgatttaattaaacgaattattaaagaaaactttttgatgcaagaaggatcttatcatggaaatg
attgtttattgattctattgatgagtttattattattgttctaaagaaaatctttgactttgcaatatttacagGTTGTTGAAGTTTCCACTTCCAAAACTG
GAAAGCACGGTCACGCTAAGTGTCACTTTGTTGCCATTGATATCTTCACTGCAAAGAAGCTGGAAGATATTGTTCCATCTTCCCACAATTGTGATgtatgat
cattctttgctcttctatttgtcttgtttgtgttatcgttttgacaccttttcttatctcactttatccattctcgtgtctttttattgcagGTCCCTCAT
GTCAATCGTACTGACTACCAGCTGATTGATATTTCTGAGGATGGATTTGTAAGATTTATTTCCTTTTTTTACTACTTTTGGGTCATATTTGTTCACCCCTTT
CTTGTATTGTTTCACTAGTCATTTCAACTTGGGCTAACTTGAGTTATGATATTTTAGGTGAGTCTGCTTACTGATAATGGAAATACCAAGGATGACCTGAAG
CTTCCAACTGATGACAGTCTGCTCACGCAGgtttgttgatatgaatgacttctgctaaatctgtgtcaatatctctgtagacattgatgtgtcattaattat
gctcttttgggaattgatgtgtcagtttatctattctggccttgcaacgctgatagaaatttttaggtggtgattattatagctaataattaatggtcatgg
ctttggaattgtacagATCAAGGATGGATTTGCTGATGGGAAGGATCTTGTCGTGTCTGTCATGTCTGCAATGGGAGAGGAGCAGATCTGTGCCCTTAAGGA
CATTGGCCCCAAGTAGTTCATTGCGTGTTGCTCTATCAAAACTCAAAATGTTTTTTTATCTTAAGACCATAAATTTATTGTGATACAGCTTTGTTGTTGATG
GTGGTTTTATTTGCTTTGAGAATATGTGGTCACGTTTTATTTTATTTTTCCTGCAAATTATTCTGAATGAGATGTTACCAAAATTATCATATTCAACTTCAA
TATTTTTTTTAATGTTGTATGAACCGGCAAAACGTGCAATCCAATCTTTGTATTTGTATCTAATTTGCCAGTATTGGCAAATTAAGTCAGCTATTTTGCCAG
TATTGGCAGTTAA Receptor for activated protein kinase C CGATTTGTTACCTTGTTTGGTAACGGAGTTTGATGGTTAATAAAATTTAATTTTCCATTAAAATAAAAATAAAAATACATGAACCAATT
GAAAGTTACATTTTTTACATTAAAGTTTTATTTGTCTAATTTTTTAAAAACGTATTTTGTGTCAATCACAATTTTAATGTTGAGACTCA
CAAATTGGTTAACTTTTAATTACATGCAATAAAGTACTACACCTTTTGCTTATCATTTGTTATAGTTTTAATTTTTTTTGTTAATTAAA
TGTTACCAATACCCAAAAAAATCGTTCTTAAAAGAGAGAGAGTTATATATTGGGAAATTTACATAAAATAATATTTTCGGTAAATATTT
TACATTTTTAAGTTGAAATATATATTCCAATATTTTTACGATGTTCTATAAAAACAACAAGAAAATAATAAAAAATAACCACATGAACG
TAACAGGAAAACAACATAAAAATAATATATAAATAACAAAAATCCAACAAAAAAAATAACAAGAGTATAATATAAAAATAATATTAAAG
TATTAAAAGACTGGCTGCACCTTCCAGTNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNAAAAAA
AAAAAAAAAAAAAAAATTACAACAATGTTTAAAATTAAGGTTTTTACCATATTGAAATTTCAATTTCTTTTACTTTTTTTTTACTG
TGGAGCAGAATTTTTTTAAAAAATACTGTGCAAGTTTTATATTGTGTAATGTGTAAAGTTTTTAATGTTGTTTCACGGTTATTTTTTAG
TTGTTCTACTATTGTTTTAATTGTTCTGTTTTGTTGTTTTACGGTTGCTTTATAAAAAGACAGTATTTTTGTAAAAGATTCCATGTACC
AGTAAAATTGTAAACTTTTGTCTAAAATCTAATATTTTTGTAAAAATCCCTTTAATATTCCTTATTTTCGTGTATTTCTAAAATAATTC
CTTATATATTGGATTATTTACACCACATACTGAAAATTTTTTTTTTTTTTTATCTTTTTGCCATGGTGCAGAATTTTTTCAAAAATACAG
TGTAAGTTTTATACTATGTACTATGTTAAATTTTTACTGTTGTTCTACTATTGTTTTTTAGTTTTCCACTATTATTTTTAGTTGTTTTA
TTATCTGTTTCACTGTAGTTATATAAAAACATAGTATTTTTGAAAAAAAAATTAGTGTGATAATATTTTTGTAAAAATTAACCTAAATT
CTATTATTTTTATAAATTTCCTTATATATTTGGAGAAAATTACAATCTATATCATTTTTATATTGTCCTCTTTTATTTTTACCATCTTT FIG. 10 (continued 8)

TTTAAAGTCTATCAATTTTACCTCTTTTTTTAAACATTGTACCAATTTTGCCCCTATCACTTCAAGATACTTTCCATGTGACTCTCTTA
TGTCAGAGTATTTTGAGTACAATACATATAAAAAGAAGTATGTTTCAATTAAATATAAAATTAAGTTAATTTGATTAATTGATTATTAA
AAATGATAATTTTCAACTTACCCCATATATTTGAGTGAAGAACCAACAATTGGGCTTTTTCCCAATTAATCCAAACCAAGAATAACCTT
ATCAACCCAACCAACCAAACAACCACCTTAGGGTTCGTTCATTCAGATATCCCCAAAAAAAACCCTAATCAAAACGATTTTCTCTCTTC
AAATCCCCACATATAAAAATCCCATTTTTAACACTTCTCATTTTCATTCTGGTTNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNTAAAATATACATCAAACCAACAAACCCTAGAAACACAGAGAGAGAGAGAGCTTCAGCAGCCGAAACC
CTAGACCCTTCTTCTCAATCCAACCATGGCAGCTGAAGGACTAGTTCTCCGTGGCATCATGAGGTCTCACACCGACATGGTAACAGCCA
TAGCTTGCCCAATTGACAACTCGGACATCATCGTCACTGCTTCCCGTGACAAATCCCTAATCCTATGGAAACTCACCAAGGACGACAAG
ACCTACGGTGTTCCCCACCGCAGGCTAACCGGCCACTCTCACTTCGTCCAAGACGTCGTTCTCTCATCAGATGGTCAGTTCGCTCTTTC
TGGATCTTGGGATGGTGAGCTTCGTTTGTGGGATCTAGCCGCCGGAGTCTCGGCAAGGAGATTCGTTGGTCACACAAAAGATGTTCTTT
CTGTGGCTTTCTCGATTGACAATCGTCAGATCGTTTCTGCTTCTCGTGACCGTACGATCAAGCTTTGGAACACACTCGGTGAGTGTAAG
TATACTATTACTGATGGTGAAGCTCATAATGATTGGGTTAGTTGTGTTAGGTTTAGCCCTAATAATCTTCAGCCAACTATTGTTTCTGC
TTCATGGGATCGTACTGTTAAGGTTTGGAATCTTTCCAACTGTAAACTGAGGTGTACTCTTGCTGGACATGGTGGGTATGTTAACACTG
TTGCTGTTTCACCTGATGGTTCACTCTGTGCCAGTGGTGGTAAAGATGGTGTTATCTTGCTTTGGGATTTGGCTGAGGGAAAGAGATTG
TATTCTCTTGATGCTGGTTCTATTATTCATGCTCTTTGCTTTAGCCCTAACAGGTACTGGCTTTGTGCTGCTACTGAGAACAGTATTAA
GATCTGGGATTTGGAGAGTAAGAGTATTGTTGAGGATTTGAAGGTTGATCTTAAGGCTGAGGCCGAGAAGACTGATGATACCCATGTTG
CAACTGCCAACAAGAAGAAGgtataattctaatgtcatttttgttttgattttgcttaatttgttggttttgagtaatctgaattgtg
tgtataaatattggttatttgagtttgaacattgattgttagatgaaaatggttttatgattcatttgtgtataaagataaaggtaatg
ctaactctttagatgatgtttcaggcttaagaacataactttgtattggggttttaaggacattattgtgtttaaggtttaatctcag
agttaactctttagacgacttttcaggtttatgaacatatttatgagatatagtcttgtaccgaaaagttagcatttttcctgttgtt
tattgtactattgtttttagtttnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnntatggttgatcttgaatgaattacagGTTATATACTGCACAAG
CTTGAGCTGGAGTGCTGATGGAAGCACTTTGTTTAGTGGATACACCGATGGAGTAATTAGAGTTTGGGGAATTGGTCGTTATTAGAAGG
AAAAAGCTTCTATCAGTAATATTATTCTCCCTAATGCACTTCTTCTACTGTTTTCTTAGTTTTTGAGAACAAAAAACCGTATTTACTAT
CTTCTTAAATTCTAGTGTTTTCGGAAAAAAGGTATTTAGGTTTTGTTGGAGATGTTGAATTTTTGGAATTCTCTTAAGTTGATGACTT
GTGGCTTTGAGGCCCCATTTGTTTTTTGGTTTTTGTTTTCTTTTATATATTTCATTAGATAATCATGTTGGTCTCTCTATACTTTTCTC
TATTTGAAATCCCAATTTGATGGTGGAATTCGATGGTGGTGTGTGCATGTGCAATGTTTCATGAATTGTATAGGCTCAATTCCCTTCAA
ATTGAATGATGAAATATTTTTAAAGTTGAAGAGTGAA FIG. 10 (continued 9)

FIG. 11

*CsSERK1 (SEQ ID NO: 45)*

>csa_locus_12407_iso_1_len_2292_ver_2

GTTTGGGTTTGGGGTTGGGGTAGGAATTTTTTGTGATGTTGTGTTTGGGTGTGGCATACCATTTGGATCTAAGGTTTTTGGTTAC
TTAGACTAAAATAGCAAGGGAGGAAATATGGAAAGGAAGAAGCTTTGGTGGTCTTCATTTTGCCTTTGGTTGATTTTGGTAGTTC
ATCCTTTATGGGTGATTATGGTATCTGCTAATATGGAAGGTGATGCCTTGCATAGTCTGAGGTCCAATTTACAGGATCCCAACAA
TGTTCTGCAGAGTTGGGATCCCACCCTTGTAAACCCGTGTACATGGTTTCATGTCACTTGCAACAATGATAATAGTGTGATAAGG
GTTGATCTTGGAAATGCAGCTTTGTCTGGTCAACTTGTTCCACAGCTTGGCCTTCTCAAGAATTTACAATATTTGGAACTTTACA
GTAATAACATTAGTGGAACAATTCCTAGTGATTTGGGGAATTTGACCAGCTTGGTTAGCTTGGATCTGTATTTGAATAGTTTTAC
TGGTCCTATCCCGGACACCTTGGGCAAGTTGTCAAAATTAAGATTTCTTCGGCTTAACAACAATAGTCTGACGGGTCCAATTCCT
ATGTCGTTGACCAACATCACCTCACTGCAAGTGCTGGATCTGTCAAATAACAAATTAACCGGAGAGGTTCCAGACAATGGCTCGT
TTTCTTTATTCACTCCCATCAGTTTTGCTAATAACTTAAATCTATGTGGCCCGGTTACTGGACGACCCTGCCCAGGATCCCCCCC
ATTTTCACCTCCTCCTCCTTTTGTCCCACCACCCCCAATTTCAGTCCCAGGTGGAAATAGTGCGACTGGGGCTATTGCTGGTGGA
GTTGCTGCTGGTGCTGCTTTATTATTTGCTGCTCCTGCTATTGCATTTGCTTGGTGGCGTCGAAGGAAGCCACAAGAATTTTTCT
TTGATGTACCCGCTGAGGAGGATCCTGAAGTTCATCTTGGGCAGCTTAAAAGGTTTTCGTTGCGAGAATTACAAGTGGCAACTGA
TAGTTTTAGCAACAAAAACATTCTGGGACGGGGTGGATTTGGTAAGGTCTACAAAGGTCGCCTTGCAGATGGTTCTTTGGTTGCT
GTAAAGAGACTGAAAGAAGAGCGTACACCTGGTGGCGAGTTGCAGTTTCAAACAGAAGTAGAGATGATCAGTATGGCTGTGCATC
GGAATCTTCTTCGATTACGTGGGTTCTGTATGACACCAACTGAACGATTACTTGTTTATCCTTATATGGCTAATGGGAGTGTTGC
CTCATGCTTAAGAGAACGGCCGCCACACCAACTGCCTCTTGATTGGCCTACTAGGAAACGAATAGCATTGGGTTCTGCAAGGGGT
CTTTCGTATTTGCATGATCATTGCGATCCAAAAATTATTCATCGTGATGTGAAAGCTGCTAATATTTTGTTGGATGAGGAGTTTG
AAGCAGTTGTTGGAGATTTCGGTTTGGCTAAACTTATGGACTACAAGGACACTCATGTTACTACAGCTGTACGAGGCACAATCGG
GCATATTGCTCCAGAGTACCTCTCTACCGGGAAGTCTTCTGAGAAAACCGATGTGTTTGGCTATGGAATCATGCTTTTGGAATTA
ATTACTGGACAGAGAGCTTTTGATCTTGCTCGGCTTGCAAATGATGATGATGTCATGTTGCTCGACTGGGTGAAAGGACTACTGA
AAGAGAAGAAGTTGGAAATGCTGGTGGACCCCGATCTTCAAAAGAACTACATAGAATCCGAAGTAGAGCAGCTTATTCAGGTTGC
ACTGCTCTGCACACAAGGTTCTCCCATGGACCGACCAAAGATGTCAGAGGTGGTGAGAATGCTCGAAGGCGATGGCTTGGCCGAG
AGATGGGATGAATGGCAAAAAGTGGAAGTACTACGACAAGAAGTCGAACTAGCCCCTCATCCAAACTCAGACTGGATAGTAGACT
CAACCGAAAACTTGCATGCGGTCGAGTTATCTGGTCCGAGGTAACCCTGGCACAATAGAAAGTGGAAGAAAAAGGGAATTTACTT
ACAACTTAATTTTTTTAATTAATTATAATAGCTTTTTTTTCTTCTTCTTAATGACCATAATCTGATTAATGTCTCTTTGTAAGT
CCATTCTGCATTGTATTCGTTACATTTGTGCATATGAGAGTCGCATTGGTAAGGTGCAAATTTGTATTGTCTGCTGCAGTGTGAC
AAAAGCCATAGATGTTTTTATAATATATGAAGCTGTGGCAGTTTTTATCTTTTGTTCACTGCAGCAGACAATACAAATTTGC

*CsBBM (SEQ ID NO: 47)*

>csa_locus_8084_iso_7_len_1661_ver_2

AATAATAATAATAATAATATTATGAGTATTATTACTAATGATAGTAATCTCAGTTGCCAGCTGGAAGCGCCGCCGTCTGCGGTGGCTCC
GGTGTCGTCTAAGAAGACCGTTGACACTTTTGGTCAACGTACCTCTATATACCGTGGTGTTACTCGACATAGATGGACTGGTAGATATG
AAGCTCATTTGTGGGACAACAGTTGCCGAAGAGAAGGCCAGAGTAGAAAAGGGCGACAAGTTTATTTGGGTGGATATGATAAAGAAGAA
AAGGCAGCAAGAGCTTATGATTTGGCTGCCCTTAAGTACTGGGGTCCTACCACCACTACAAATTTTGCAGTGTCTAATTACGAAAAAGA
ATTAGAAGATATGACGAACATGACTAGGCAAGAATTCGTTGCTTCACTTCGAAGGAAAAGTAGTGGATTTTCTAGAGGAGCTTCAATAT
ACAGAGGCGTCACAAGGCACCACCAACATGGTCGATGGCAGGCAAGAATTGGAAGAGTAGCAGGAAACAAAGATCTCTACCTTGGCACC
TTTAGCACACAAGAAGAAGCAGCCGAGGCATACGACATCGCGGCGATAAAATTCCGAGGCCTAAACGCCGTAACAAACTTCGACATGAG

CCGTTACGACGTTAAAAGCATAGCCAACTCTAATCTCCCCGTTGGAGGAATGTCAAACAACACCAAACTTTCCAAAACCTCACCCGAAC
GGGCGATTGACAACCTATCATCGCCCGCTTCATCATCCCTCGTCGCCTTCTCCTCCTCGGCCACCACCAACAACAACAACACAACACCC
CAACAACAACAACAACAACAAATGTCCTCCAATCTAAGCTTTACTCTTCCCATCAAACAAGACCTAACAACAACGACAACATCGTCAAC
GGATTATTGGTCAAACATTTTCGGTTTCCAAAACCCTAACCCTAGTAGTACTACTAGTACTACTCCTTCCTTATTGTTGGGCCATAATA
GTCACAACCTCTCGGCCACATCAACTAATGCAACAACAACTACAACAACAACAAGTAATGGAGGGTATTATGGTAATTTCATCGAGTCA
ATTTCTAATAATAATAATAATAATACTAACTTGGGTTATGGATCAGGATTAAGTAGCTGGATTAGTAATAGTAATCATAATATTAACGG
AGGGAGTAGTAATAGTAGTAATGTTCATAATCATCTTCATCATCATCATCATCATGAAGTTGTTCATGCGAAACAACCTAGTCTTTTTC
AAACACCAATATTCGGCATGGAATAATAATGATGATGATTTTTCTCGCACACTTGTTGGAAAACTACTGGCACGTGGGAATCTGTGGTG
TTTGAATTTGCATGGAAAAGGGAGCTAGGGTTGTTGTTGTTATTGTAATAATAATAATAATATGGTGGAAACTGACAATATTCATC
ATAATATTATTTTTCATGAGAGATGAGAATGTAGTAGTGAAATAGCTAGTACTAACTGAAGTTGGGTTCTTTTAGGGACCATGTTTTTA
CTTTTTTATTATATTTTTTGCTTTTTCTTTTTCCTTTAGTTTCATTACTAGATCTACTGACATTATTATTATTCTAGGTGTTAAGGAAA
GGAATCCTTTTTGTAATCCTTAGTTTTTTTCATATATATTATATAAATGCACCTTCTTC

FIG. 11 (continued)

SEQUENCE LISTING

```
<160> NUMBER OF SEQ ID NOS: 61

<210> SEQ ID NO 1
<211> LENGTH: 2773
<212> TYPE: DNA
<213> ORGANISM: Cannabis sativa

<400> SEQUENCE: 1

ccgtgaaaac ttaacacagt acacaatatt tttgagcccc atagtaaaaa aataaaaaag     60

ttaaaaattt gagtatgtgg cgtaaaaatt ccatatatat ggaatatgga agatatatag    120

aagggataat tacaccacat cgtgaaattt cttagttttt tactttcata ctgtggggcg    180

gaattttttt caaaaatact gtgtgagttt tatactggtt aagttttcac tgttgttcta    240

cggttgtttt tagttgttcc actgttattt ttagttgttc tgttttgtat tctattttgt    300

attctattgt tgttttataa aaatatagta ttttttaaaa aatttccggg tgacagtatt    360

tttataaatt ttcttatata aaactaaacc taataacgag gcccagccca gtaacacttc    420

taaatctcaa aatgggtcaa aaatgtttta actagaagcc caagcccatt aaacaggcaa    480

tgaatgacgt cattaccgta ggaattggtg gtcttggaaa ggccaactcg acaaaactaa    540

tattccaaac tttgcgtgta agcggagcgt aagacacgtc atcctttata cgtggcctaa    600

tataattggt aaccctagtc aagtgggttt ggtttggcct gaccaagtcg gtttaggatt    660

tatccatttc cttctttttt aaaaaaagaa atatcagaga aagtcggtca agttgattta    720
```

```
taaattgcct cttacccttc atctttcatc attactactt tctatctaag caattctcca    780
ataatcatca aattctccac aagaacccta atcccttctc ttcgtacatt caaggtaatc    840
aaattcttgc ttctgttatc atcatcatag aatttttgtt ttatataatt gtatcaatga    900
tcttcgcttt cgtataactt tagggttttt tttaattttc gttaaggttg cattttatct    960
ttaattctat cgaaaatttt ttatttttct ttttcatctg gaaagcgtgt atcgtatttt   1020
gaattttatt tgtgtgtata tataaaattg aacgaactgt atcaatgatc ttgggtttca   1080
tttaatttta ggttttttaa tttaccgaat aatgtttgga taatgatact tctttttcat   1140
ttgtcaaatt ggtcgtatct ttgaattttc ttttgtgttt atactgttta tatttgaagg   1200
aactgtatca attatatttg gtttcataca attttagggt tttttattac gccaagattg   1260
tttttttattt tcttttaaat tctacgggtt aatttttgta aaagagaact tttcttttgt   1320
ctgacattat tttattgtct tttttttttt tttttttgga aaaattctga tagattttgt   1380
tttaattctg tatttttaga tgcaaatctt cgtgaaaacc ctaaccggta aaaccatcac   1440
tctcgaggtc gagagttctg ataccataga caatgtcaag gctaagatcc aagacaagga   1500
ggggattccc ccagatcagc agaggctgat tttcgctgga aagcagctcg aggacggtcg   1560
caccctcgct gactacaaca tccaaaagga gtcgaccctt catctggtgc tccgtctacg   1620
aggcggtatg caaatcttcg ttaaaaccct cacaggaaag actattactt tagaggtcga   1680
gagctcggac accattgaca atgttaaagc taaaattcaa gataaggagg gcattccccc   1740
agaccagcag aggttgattt tcgctggaaa gcaacttgag gatggccgga ctctagctga   1800
ctacaacata caaaaggagt ccacccttca tttggttctc cgtcttcgtg gaggtatgca   1860
aatctttgtc aagaccctca ctggaaagac cataactttg gaggttgaga gctccgacac   1920
cattgacaac gtaaaagcta aaatacaaga caaggaggga atccccccag accagcagag   1980
gctcatcttt gccgggaagc agctagaaga tggtaggact cttgctgatt acaacattca   2040
aaaggagtct accctccact tggttctccg tcttcgtggt ggtatgcaga tttttgttaa   2100
gacccttact gggaagacaa taaccttgga ggttgagagc tccgacacaa ttgacaatgt   2160
caaagcaaaa atccaagaca aggagggtat cccaccagac cagcagagac ttatctttgc   2220
cggtaagcaa ctcgaggatg gaaggacact tgctgactac aacattcaga aagagtccac   2280
ccttcatctt gtgcttcgtc tccgtggtgg aatgcaaatt tttgtgaaga cccttaccgg   2340
aaagaccatc accctcgagg ttgaaagctc ggatacaatc gacaatgtaa aggcaaaaat   2400
tcaagataag gaaggaatcc cccctgacca acagaggttg atttttgctg ggaagcaatt   2460
ggaggatggc aggactcttg cggattacaa catccagaaa gagtcgaccc ttcaccttgt   2520
gctgcgtctg aggggtggca tgcagatctt tgtgaagaca ttgactggga agaccatcac   2580
tttggaggtg gagagctcgg ataccattga taatgtcaag gcgaaaattc aagacaaaga   2640
gggcatccca ccagaccagc agaggttgat ttttgctggg aaacaattgg aagatggaag   2700
gactttggct gattacaaca ttcagaagga gtctactctt caccttgttc tccgtcttcg   2760
tggtggcatt taa                                                      2773
```

<210> SEQ ID NO 2
<211> LENGTH: 750
<212> TYPE: DNA
<213> ORGANISM: Cannabis sativa

<400> SEQUENCE: 2

```
ccgtgaaaac ttaacacagt acacaatatt tttgagcccc atagtaaaaa aataaaaaag     60
```

```
ttaaaaattt gagtatgtgg cgtaaaaatt ccatatatat ggaatatgga agatatatag    120

aagggataat tacaccacat cgtgaaattt cttagttttt tactttcata ctgtggggcg    180

gaattttttt caaaaatact gtgtgagttt tatactggtt aagttttcac tgttgttcta    240

cggttgtttt tagttgttcc actgttattt ttagttgttc tgttttgtat tctattttgt    300

attctattgt tgttttataa aaatatagta ttttttaaaa aatttccggg tgacagtatt    360

tttataaatt ttcttatata aaactaaacc taataacgag gcccagccca gtaacacttc    420

taaatctcaa aatgggtcaa aaatgtttta actagaagcc caagcccatt aaacaggcaa    480

tgaatgacgt cattaccgta ggaattggtg gtcttggaaa ggccaactcg acaaaactaa    540

tattccaaac tttgcgtgta agcggagcgt aagacacgtc atcctttata cgtggcctaa    600

tataattggt aaccctagtc aagtgggttt ggtttggcct gaccaagtcg gtttaggatt    660

tatccatttc cttctttttt aaaaaaagaa atatcagaga aagtcggtca agttgattta    720

taaattgcct cttacccttc atctttcatc                                     750
```

<210> SEQ ID NO 3
<211> LENGTH: 2061
<212> TYPE: DNA
<213> ORGANISM: Cannabis sativa

<400> SEQUENCE: 3

```
ggtgactgat tccctcaatt tcccagcaat ctcaatgtgg ttcatattga accctccagg     60

caaagctaca atccagatcc agaacataga cagttttgac tggttgttca ccaagtataa    120

caatccacta ttgaagcaag agtccagtga ttctagattt acatttcaac tcaaccacct    180

tcgtttctat ctgcctgaga tcttccctgc actggataag gtagtactct ttgaccatga    240

tgtggtggta caaaaagacc taactggtct atggcatctt gacatgaagg gaaaagtagt    300

tggagcggta caaacttgtc tgaaaggaaa atcttcatat cgccggatgg actcctttct    360

caacttttcc gaccctttttg tagccaagag ttttgatatc aatgcctgca cttgggcatt    420

tgggttgaat ctatttgatc tacaggagtg gagaaaacaa aatctgactg ccctttacca    480

cagatactta caaatggtac atcaaaatct cttcacacat ctacttagtt tcaattaagc    540

cttaaaagtt aattataatc taatgcttat ctttttcggg tgtgttttgt tgcagggttc    600

tgaacgacct ttgtggatgg ctgggagttt gcccttaggg tgggttacct tttataagaa    660

aacagtggct ttggatagaa gatggcatat cactggattg ggttatgagt ctgaattggt    720

tcgtgtggag gttgagagag cagcagtgtt acacttcgat ggaattatga agccttggtt    780

agatatagca attgggaagt acaagcaata ttggtgtaga ttcagataat catacatcca    840

cgaataattg aacatttgca agactgtcaa tcaatcaatg gagggagagt acaataccat    900

gacaattctt agcagaaaat tttttacacc tttttttttt ttcctttctt gcattaggaa    960

ttgcacttgt tcacttaatt ctttttccca taatgattct tcatgtaaag ttcaactaat   1020

attttttccc acacagatat ttttctgggg atattacttt agggaagttt caaattatag   1080

aaataattcg aaaccaaaaa caaaaaagaa agtggtgtat tttaggggat tctgtaacac   1140

ttcactaggt tactttcctg tacatatttt tccattcaag gcgcttaaca tgtattccgg   1200

attattattt tcttggaata gcctaatcca tatattttgg gataaaaatg gaataaagag   1260

aattttacct gggcatatga gagcaacgga aatggaatta ttagaaaatg gattgtgtgg   1320

cacgtggaaa attttgattg ggtgtaagca gatagggata gggctaagct ttgtttgtgt   1380
```

```
ggtgcagtct ggacagattt ccaaccaatc agaatgctcc gttccttctc ttcaatccac   1440

tgcaaaaaaa caaaggcttt ttataacacc ataataacaa aatcttccac tgcaaaacca   1500

gttttttttt cccttcccgg aatatttttc tcggaaaatc aagcttcatc aagcgataat   1560

ggcaagcttc accgctagtg ctccaacctc ttcagtcctc cgggcatccc ttctccacaa   1620

accatccttg gggatccaat cctcacctgt tcttggtaat aagacctata agtttttgta   1680

gttagctact cttttttttc tttcaatttt caatatttgt ttttttttcg aacttgaatt   1740

tgaatttgaa ttgtacattt agcacttccc acaatggcga agggaggaaa agtgaggtgt   1800

tcaatggaga aatctgaaag caagcaaaag atgggtatgg gagcttcttt aatggctgca   1860

gctatggcag caacggtgtc tagtccagct atggctttgg tggatgagag attgagcaca   1920

gaaggtactg ggcttccgtt tgggctgagc aacaaccttc ttggttggat ccttcttggt   1980

gtgtttggtc tcatctgggc taactacttt atctacactt ccactcttga tgaagatgag   2040

gaatctggat tgtctctctg a                                              2061
```

```
<210> SEQ ID NO 4
<211> LENGTH: 1476
<212> TYPE: DNA
<213> ORGANISM: Cannabis sativa

<400> SEQUENCE: 4

ggtgactgat tccctcaatt tcccagcaat ctcaatgtgg ttcatattga accctccagg     60

caaagctaca atccagatcc agaacataga cagttttgac tggttgttca ccaagtataa    120

caatccacta ttgaagcaag agtccagtga ttctagattt acatttcaac tcaaccacct    180

tcgtttctat ctgcctgaga tcttccctgc actggataag gtagtactct ttgaccatga    240

tgtggtggta caaaaagacc taactggtct atggcatctt gacatgaagg gaaaagtagt    300

tggagcggta caaacttgtc tgaaaggaaa atcttcatat cgccggatgg actcctttct    360

caacttttcc gacccttttg tagccaagag ttttgatatc aatgcctgca cttgggcatt    420

tgggttgaat ctatttgatc tacaggagtg gagaaaacaa aatctgactg ccctttacca    480

cagatactta caaatggtac atcaaaatct cttcacacat ctacttagtt tcaattaagc    540

cttaaaagtt aattataatc taatgcttat ctttttcggg tgtgttttgt tgcagggttc    600

tgaacgacct ttgtggatgg ctgggagttt gcccttaggg tgggttacct tttataagaa    660

aacagtggct ttggatagaa gatggcatat cactggattg ggttatgagt ctgaattggt    720

tcgtgtggag gttgagagag cagcagtgtt acacttcgat ggaattatga agccttggtt    780

agatatagca attgggaagt acaagcaata ttggtgtaga ttcagataat catacatcca    840

cgaataattg aacatttgca agactgtcaa tcaatcaatg gagggagagt acaataccat    900

gacaattctt agcagaaaat tttttacacc tttttttttt ttcctttctt gcattaggaa    960

ttgcacttgt tcacttaatt ctttttccca taatgattct tcatgtaaag ttcaactaat   1020

atttttttccc acacagatat ttttctgggg atattacttt agggaagttt caaattatag   1080

aaataattcg aaaccaaaaa caaaaaagaa agtggtgtat tttaggggat tctgtaacac   1140

ttcactaggt tactttcctg tacatatttt tccattcaag gcgcttaaca tgtattccgg   1200

attattattt tcttggaata gcctaatcca tatattttgg gataaaaatg gaataaagag   1260

aattttacct gggcatatga gagcaacgga aatggaatta ttagaaaatg gattgtgtgg   1320

cacgtggaaa attttgattg ggtgtaagca gatagggata gggctaagct ttgtttgtgt   1380

ggtgcagtct ggacagattt ccaaccaatc agaatgctcc gttccttctc ttcaatccac   1440
```

tgcaaaaaaa caaaggcttt ttataacacc ataata 1476

<210> SEQ ID NO 5
<211> LENGTH: 4357
<212> TYPE: DNA
<213> ORGANISM: Cannabis sativa

<400> SEQUENCE: 5
gcagatactt accacatcat catgaaggtt tgcccaatac ttttgatgaa agagggcagg 60
gaggccatcc gctcctagag tttttgttgg tggcatctct ttcactgcca attaatagtt 120
tcttcttctt taaatgactc tagcaaatct cgattcattt ctagagtaac ccattgtggc 180
actgagttta ggacatcatc aaggacatca tgttggatca tggaaatggt gaaaagggta 240
tgaaagtacg tactaataat tctttgaacc acaaccttgt cttcttgcca aattatcatt 300
gtgtccacca acccatgtat ctcatttttt ttctttgagc agaagcttca tgatgaaagt 360
atttagtatt atgatcccca ctttttaacc atagagtcct acttctttgt cgccggtact 420
tctcatcctt atcaagaaaa aaatttgact tttttttctta tttttttaatt tccatcccaa 480 tggatggttg ctgaacctta gataagtcac ccaaggtctt cttaactcta tcaagttctt 540
cattgttttt tgttttttttt tcttattcca cttcttcgaa gctttcccac atagagaggc 600
cctccgtttg aacccctttg tcatacctaa attagctttg tccctctaat gctgctcagc 660
aatcgcttta cactccccat cctcgcacca agcctcttcg aaatgaaatc gagttctcct 720
cctgaccatt ccaaacttct atgttgaatg acctagtggt atgtcaatca caaaggctct 780
atggtcggac tccagccagc ccaacacctt aacatccgct ctcgcaaagc tttccatcta 840
aattacacaa tgccttgtct agcctctcca tgaccctatt ttccccatgc ccattacacc 900
aagtaagttc agttttacaa gtgcaaaaat tagccaatcc acattcatcg ataacctccc 960
taaattcctc catatccttc gaagctttaa cccgacccct attttttcag atagactaac 1020
aatttcatta aaatccccaa cacaaagcca tgggctagta atttcattat gtaaatagca 1080
tagtaattcc gaagaaaact tccgttgaga tgtattagga ttcccgtaaa aacccgtcaa 1140
attcaacggt aaaagtcctc caaccaccac agtcgtaatg taactaggag aactcgaatc 1200
cactcgtaat atttcttttt tttaaaaaaa aaaaaagcta atattttaat ttttttaatt 1260
aaattttagc atttgaaaat aaataaagtg gggagtaaaa tacatttata ataagggatg 1320
gagcccagcc caaccagcca agagtgcaac ccacgtactg tgttagctga caaatgaatg 1380
aaaagaatat agaaatggat ttgtttgaag acataatgac gagtccagac tgtactctta 1440
atctgatctg acggaccaca ttgcatcatc atcaccatcg ctcatcttta tatactatta 1500
ttacacacct tccctttccc tctcattctc cttcttctct ctcaaacctc taaactctaa 1560
accattcatt ctttcattca tttaccacaa accctctaaa cttccatctt gcttttcgca 1620
tttcaacagg ttcataatct ctttcgatct ctttatttca cccgatctgt gcttatgttt 1680
tagtattatc attttttaat ttcatattta tgtatgtttt acaatttgta tttcattgtt 1740
ggatttatga ttttgtgttt atttctttgt ccaagttgtt aaaattaatg ctcgatgaat 1800
tgggttttcg ttaaaaagat tttttttttt ttttgtttct ttttatgttt tttaagatta 1860
aatatgcaaa tataaatgtg gtaaataacc taaagaagaa gaagaaagag aaaagatcaa 1920
aaattgagtt catctctaca aattgattgt atctgtttta ttttgtgtgt acattcttat 1980
tttaacacaa gaatttggtg tacaaataga tacatgcatt cgatttatgt tgcattgtta 2040

-continued

```
gtatcattgt atcgctatat gacgatctac cgcttttatt tattatttta tgaaagatgt   2100
tcttataaca tagtttggtg aacaaatagg taagtgaaga tggcagatgc agaggatatt   2160
cagccacttg tctgcgataa tggaactgga atggtcaagg tattaatgtt atttgtcatt   2220
gttgaaaagt ttcccattga atcattaatc ttctgtgcaa aagctagctt aatgttactt   2280
gtgggtgtgt agaatttgcc tcttgaccat taattattgt gatcttacct attaggctgg   2340
gtttgctgga gatgatgctc cacgagctgt gttccccagt atcgtgggtc gtcctcgtca   2400
cactggtgta atggttggaa tgggccagaa agacgcatat gtgggtgatg aggcacaatc   2460
caagcgaggt atcttaactc tgaagtaccc aattgagcat ggtattgtca gcaactggga   2520
tgacatggaa aagatctggc atcacacttt ttacaatgag cttcgtgttg cccctgagga   2580
acaccccgtt cttctaaccg aagctccact taaccccaag gccaatcgtg aaaaaatgac   2640
ccagatcatg tttgagacct ttaacacccc tgctatgtat gttgccattc aagccgttct   2700
ttctctgtat gccagtggtc gtactaccgg tgagtaccaa gtactttctt cttttcattg   2760
tcatagcatg atttcttgtt agagtatcct atagacactg aaatgagaca ttaaatatgg   2820
taagaactga gattttacta ataccaatct cattctgttt accaactact tgcatcatga   2880
tatcttacct tgtcaaatat tgtagtgtgg ctttggtttt ggaaattata tttttcttga   2940
agtttaaacc ttgaccctca ttttctaata ctattatgta gcttttatat tgccctgtct   3000
taaaataatt tagctagaag ttttgcctta gttttgcagg tattgtgctg gattctggtg   3060
atggtgtaag ccatactgtc cccatatacg agggatatgc tcttcctcat gccattctac   3120
gtcttgatct tgctggtcgt gatcttactg atcacctaat gaagattctc accgagcgtg   3180
gatactcctt caccaccact gctgaacggg aaattgtgag ggacatgaag gagaagcttg   3240
cctacatagc tcttgacttt gagcaggaga tggagacagc caaaactagt tctgctgttg   3300
agaagagtta tgagttgcca gacgggcaag tcatcaccat tggcgccgag cgattccgat   3360
gtcctgaagt tcttttccaa ccttcattgg ttggaatgga agcagcaggc attcacgaaa   3420
ctacttacaa ctccatcatg aagtgcgatg ttgatatcag aaaggatctt tacggtaaca   3480
ttgtcctgtc tggtggttca accatgttcc caggcattgc tgataggatg agcaaggaaa   3540
tctctgctct tgcaccaagc tctatgaaga ttaaggtggt cgcaccacca gagaggaaat   3600
acagtgtctg gattggaggc tccatcttgg cctctctcag caccttccag caggtttata   3660
tttttcata tctaagtttg gcatgatgat cttaatatga tgattcaata attactgata   3720
tcatatttta tcttttcctt atgcagatgt ggattgcaaa agcagagtac gatgagtctg   3780
ggccatcaat tgttcatagg aaatgcttct aagcatgtga gaattagaac tactgcagag   3840
agaaaagcaa gtactgttgt tttgattatg ttggagaaaa gtgttgtttg cagaaggttc   3900
attctagctc gttacctttt ttttattctc aacttgaagt gacttcggaa ggccaggagt   3960
taatttatcc aatttgtttc ttttaaattt tattttattt ttgttattac aacttctttg   4020
attatcatta ttattatttt ttggtcattc catcccaaaa ttccgtactt acaaaagctc   4080
atattgaatg cttaaatttc ttatgaaccc aattcatgag ataaaacctt tattttatga   4140
atcaaataat ctgtatgatc cacgtgaaaa ctaaatttta tttacacggc aaaagcagtt   4200
cttctaaaag aagacttgca agtgaggctt cttctcagca tttttacact caaaatatca   4260
tcttcaaata aacaaaagtt tatcaaacaa tgtcaaaggt tgacttaaac tattgtaatc   4320
aattctcttt gactcttagt tctgccaagg aagaaag                              4357
```

-continued

<210> SEQ ID NO 6
<211> LENGTH: 2139
<212> TYPE: DNA
<213> ORGANISM: Cannabis sativa

<400> SEQUENCE: 6

```
gcagatactt accacatcat catgaaggtt tgcccaatac ttttgatgaa agagggcagg     60
gaggccatcc gctcctagag tttttgttgg tggcatctct ttcactgcca attaatagtt    120
tcttcttctt taaatgactc tagcaaatct cgattcattt ctagagtaac ccattgtggc    180
actgagttta ggacatcatc aaggacatca tgttggatca tggaaatggt gaaaagggta    240
tgaaagtacg tactaataat tctttgaacc acaaccttgt cttcttgcca aattatcatt    300
gtgtccacca acccatgtat ctcatttttt ttctttgagc agaagcttca tgatgaaagt    360
atttagtatt atgatcccca ctttttaacc atagagtcct acttctttgt cgccggtact    420
tctcatcctt atcaagaaaa aaatttgact tttttctta tttttaatt tccatcccaa      480
tggatggttg ctgaacctta gataagtcac ccaaggtctt cttaactcta tcaagttctt    540
cattgttttt tgtttttttt tcttattcca cttcttcgaa gctttcccac atagagaggc    600
cctccgtttg aacccctttg tcatacctaa attagctttg tccctctaat gctgctcagc    660
aatcgcttta cactccccat cctcgcacca agcctcttcg aaatgaaatc gagttctcct    720
cctgaccatt ccaaacttct atgttgaatg acctagtggt atgtcaatca caaaggctct    780
atggtcggac tccagccagc ccaacacctt aacatccgct ctcgcaaagc tttccatcta    840
aattacacaa tgccttgtct agcctctcca tgaccctatt ttccccatgc ccattacacc    900
aagtaagttc agttttacaa gtgcaaaaat tagccaatcc acattcatcg ataacctccc    960
taaattcctc catatccttc gaagctttaa cccgacccct attttttcag atagactaac   1020
aatttcatta aaatccccaa cacaaagcca tgggctagta atttcattat gtaaatagca   1080
tagtaattcc gaagaaaact tccgttgaga tgtattagga ttcccgtaaa aacccgtcaa   1140
attcaacggt aaaagtcctc caaccaccac agtcgtaatg taactaggag aactcgaatc   1200
cactcgtaat atttcttttt tttaaaaaaa aaaaaagcta atattttaat ttttttaatt   1260
aaattttagc atttgaaaat aaataaagtg gggagtaaaa tacatttata ataagggatg   1320
gagcccagcc caaccagcca agagtgcaac ccacgtactg tgttagctga caaatgaatg   1380
aaaagaatat agaaatggat ttgtttgaag acataatgac gagtccagac tgtactctta   1440
atctgatctg acggaccaca ttgcatcatc atcaccatcg ctcatcttta tatactatta   1500
ttacacacct tccctttccc tctcattctc cttcttctct ctcaaacctc taaactctaa   1560
accattcatt ctttcattca tttaccacaa accctctaaa cttccatctt gcttttcgca   1620
tttcaacagg ttcataatct ctttcgatct ctttatttca cccgatctgt gcttatgttt   1680
tagtattatc attttttaat ttcatattta tgtatgtttt acaatttgta tttcattgtt   1740
ggatttatga ttttgtgttt atttctttgt ccaagttgtt aaaattaatg ctcgatgaat   1800
tgggttttcg ttaaaaagat tttttttttt ttttgtttct ttttatgttt tttaagatta   1860
aatatgcaaa tataaatgtg gtaaataacc taaagaagaa gaagaaagag aaaagatcaa   1920
aaattgagtt catctctaca aattgattgt atctgtttta ttttgtgtgt acattcttat   1980
tttaacacaa gaatttggtg tacaaataga tacatgcatt cgatttatgt tgcattgtta   2040
gtatcattgt atcgctatat gacgatctac cgcttttatt tattatttta tgaaagatgt   2100
tcttataaca tagtttggtg aacaaatagg taagtgaag                          2139
```

<210> SEQ ID NO 7
<211> LENGTH: 4369
<212> TYPE: DNA
<213> ORGANISM: Cannabis sativa

<400> SEQUENCE: 7
cctcaacgaa catctgtttt aagtggagag gattttgtga aacaattatt aggtggtcat 60
gagagaacat gttacgaatt gttgcgaatg gataagaatg tatttgttga gctttgtact 120
tgtttaaaac aaaaagaata cattaaggac acccgagagg ttaaagttga agagtcagtt 180
gctatttttc ttatgattgt tggtcaaaat atgagaatga gacttatagc agatcgattt 240
caacattcgc ttgaaaccat tgataggcat tttcgtctaa cattgaaggc aatatgtaaa 300
ttaggacaag atatcattcg tccaactcag tctccattac cttctcgtat tgtcaattcc 360
tcgaaatact atccatggtt tcaggtattt aactacattt agtgtaagat aaataatact 420
ttcacatatt attagagtgt attttttttt tattaacttt tctttatttt tttaatcaga 480
attgtatagg tgcaattgat ggaacacatg tgagtgcatg tgtccctgca gataagcaag 540
tcagttacag aggtcgaaaa aatgtagtaa cacaaaatgt tttatgtgct tgtaacttcg 600
acatgttctt tacttttgta tctgctggtt gggaggcact gcaaatgatt ccagggtgtt 660
tatagatgca attacaacac ctgaatataa gtttccactg cctaaagaag gtatttgtaa 720
ccaaaattta gttattattt tattatttag tcatggtgct tatagaaaat gaatcctttt 780
gtaggtgaat attatgtttt ggattctgga tttccatgta caaaaggttt tctcccacca 840
tatcgtggtg aaagatacca tttgcaagaa tacaatagtg gacgtaatgg accgcgtggc 900
atgaaagaac tattcaatta tagacattct tcacttagaa atgtcattga acggtgcttt 960
ggtgtgctga aagctcgttt cctatattaa agatgatgcc accttacaaa ttgagtcgac 1020
aaactttaat agtaattgct tgttgtacac ttcataattt tattcgacaa cgcacccaat 1080
atgatcatat gtttagagaa tgggaagaaa aagaacttga gagtgaagac aacatagaag 1140
gatgggaaac cagtgtgtca agatatgaag ttaatttgtc tgatgaatct gctgcggcaa 1200
tggcacgtgt tcgagatcgt attgctcaaa ctatgtggac ggcttataat aatagaaatt 1260
agtcaattat attttaatgt ttgatgatac attcaggatt aaatttattt ttataaggat 1320
atattgtaga ctaatggtta ttttacatcg attttagatt aaaaaattct ttaagaattt 1380
cataattata tttttaagta ttataatatt atatttactt attatttaaa attatttttt 1440
taaataaatt agatattaat atgttattga attaaattaa aatttgtaat atttattttt 1500
ttaaaaaaaa aaacaacaca acaccaaaaa aataataata acagtaattt ttttatttat 1560
atatattttt ttaaaaaaaa gcaattttta aaaacttgtt gtttttacta tccaaacatg 1620
ttttcagttt ttgttgttta aaaactgttt ttaaaaaata ttagccaaac accatttaat 1680
ttttaaaatg acaaaaaact gttttctgtt ttcactttta aaaactgttt ttgaaaacta 1740
aaaactgaaa acacagccaa acagcctcta agagattccc cttttttgta aattagcttt 1800
ggaagattgc acaatgaaca acttgatatt tgtttgggat cttaacccaa gagatatttt 1860
ctttaacaag tctagtgata ttttccacta ctaaattatt acaattatag gcaagtccaa 1920
tagagtcaat tccctccaat tggaattcaa aaccacaacg gtcatgacag ctggacccca 1980
cacccacatc cccacaacgg tcagtttcaa attttgaaac gtccccaaat tttttaaaaa 2040
ccgacttaaa aatttgtcct ttttataccc taaaaaaacc ctagctgctc aatcatattt 2100
tctcttgtaa aaaaaagtaa ccgaaaagcc taaaacagaa gaaaaagcaa aacctaaaac 2160

```
cagagaagag aaatgagaga gtgcatctcg atccacattg gtcaggccgg aatccaagtc   2220
ggtaactcct gttgggagct ctattgcctt gaacatggca ttcaggttgg tttttcttct   2280
tcttcatttt gtgatttatt ctcatttgga tcttacttac aatgattctc ttctcttacc   2340
cagcccgatg gtcaaatgcc cagtgacaag accgttggag gtggagacga tgccttcaac   2400
acgtttttca gtgaaaccgg cgccggaaag catgttcccc gtgctgtgtt tttggatcta   2460
gaaccaacgg tcatcgatga agtgaggacc ggtacttacc gccagctttt ccatcccgaa   2520
cagcttatta gcgggaagga agacgcagct aataacttcg ctagaggcca ttacacaagt   2580
aagaagcttt ttaaattttt ggttaggttt ttgttttgtg agtgtttgtt gaaatgtcct   2640
tgaatttttt gttcaaattt ttgatttttt gtttttgttt tgtgggcagt tgggaaagag   2700
attgtagatc tatgccttga tagaatccga aagcttgctg ataactgtac tgggcttcaa   2760
gggtttctgg tttttcacgc tgttggcggt ggaactggat ctggtcttgg atctctactt   2820
cttgagagac tctctgttga ttatggaaaa aaatctaaac ttggtttaca gtttacccat   2880
ctccacaggt ttccacctct gtggttgaac cttacaacag tgttttgtct actcactccc   2940
ttttggaaca cacagatgtg tctgttcttc ttgataatga ggctatctac gacatttgca   3000
gaaaatcact tgatattgaa agacccactt acactaacct taacaggctt gtatctcagg   3060
tataaaatca cttgatgtaa tctagtctta tgttattctt gttttaggtt acttaatgag   3120
ctttttteta tgtttgggca acaggttatt tcttcactca ctgcttctct tcgattcgat   3180
ggagctctta atgtggatgt gactgagttt caaactaatc ttgtccctta cctagaatcc   3240
atttcatgct ttcgtcatat gcgcctgtga tttctgcaga gaaagcttac cacgagcaac   3300
tttcggtgtc tgaaatcaca aacagcgctt ttgaaccatc ttcaatgatg gccaaatgtg   3360
atcctcgaca tggaaagtac atggcttgtt gtttgatgta caggggagat gttgtaccaa   3420
aggatgtgaa cgcagcagtc gccaccatca agaccaagag aactattcag ttcgttgatt   3480
ggtgcccaac tgggttcaag tgcggtatca actaccaacc acccacagtc gttccaggag   3540
gtgacttggc taaggttcaa agggctgttt gtatgatttc aaactccaca agtgttgcag   3600
aggtgttctc taggattgac cataagtttg acttgatgta cgcaaagaga gcttttgtgc   3660
attggtatgt cggtgaaggt atggaggagg gtgagttttc tgaagcgaga gaagacttgg   3720
ctgcccttga gaaggactac gaggaagttg ggcagaatc tgccgaaggt gacgatgatg   3780
atgagggaga ggagtactaa gaaaaagctt tcattaatat aagtatgtgt tctgccaatg   3840
gactcattgg tctgtaactg agattacaaa catctactat ccttgttttt aatttgatgt   3900
tagttacatt ttgttctttg gttgttgaag tataacaatt gttcattttg cttaaaaaaa   3960
ttccaaattt ttcatatgtt gaaactgaac atatggatca acatgatttt gctcgcttct   4020
tggttatttt agataatgat tcactttgag agtgaggact ttcacaaaaa tcatcatcaa   4080
ttatggcacc atcatcaatt ttatttaatt aaacatgaaa aagttggatt gaaaaaggct   4140
tatttctcct cctagaacca ttatttcaga ctgtacagaa taaaggtaaa aaagaaaaac   4200
tgcttcacta tctatctctc actacttctt ggttactgac tcctccctat tctctaatca   4260
aagaaacata aacaataagc taaagaaaga aaagagagaa aaaagtaact aagtgaccga   4320
acatcacaaa catgtcttct caagttccca acttcatcat catctgctc               4369
```

<210> SEQ ID NO 8
<211> LENGTH: 2172
<212> TYPE: DNA

<213> ORGANISM: Cannabis sativa

<400> SEQUENCE: 8

```
cctcaacgaa catctgtttt aagtggagag gattttgtga aacaattatt aggtggtcat     60
gagagaacat gttacgaatt gttgcgaatg gataagaatg tatttgttga gctttgtact    120
tgtttaaaac aaaaagaata cattaaggac acccgagagg ttaaagttga agagtcagtt    180
gctatttttc ttatgattgt tggtcaaaat atgagaatga gacttatagc agatcgattt    240
caacattcgc ttgaaaccat tgataggcat tttcgtctaa cattgaaggc aatatgtaaa    300
ttaggacaag atatcattcg tccaactcag tctccattac cttctcgtat tgtcaattcc    360
tcgaaatact atccatggtt tcaggtattt aactacattt agtgtaagat aaataatact    420
ttcacatatt attagagtgt attttttttt tattaacttt tctttatttt tttaatcaga    480
attgtatagg tgcaattgat ggaacacatg tgagtgcatg tgtccctgca gataagcaag    540
tcagttacag aggtcgaaaa aatgtagtaa cacaaaatgt tttatgtgct tgtaacttcg    600
acatgttctt tacttttgta tctgctggtt gggaggcact gcaaatgatt ccagggtgtt    660
tatagatgca attacaacac ctgaatataa gtttccactg cctaaagaag gtatttgtaa    720
ccaaaattta gttattattt tattatttag tcatggtgct tatagaaaat gaatcctttt    780
gtaggtgaat attatgtttt ggattctgga tttccatgta caaaaggttt tctcccacca    840
tatcgtggtg aaagatacca tttgcaagaa tacaatagtg gacgtaatgg accgcgtggc    900
atgaaagaac tattcaatta tagacattct tcacttagaa atgtcattga acggtgcttt    960
ggtgtgctga aagctcgttt cctatattaa agatgatgcc accttacaaa ttgagtcgac   1020
aaactttaat agtaattgct tgttgtacac ttcataattt tattcgacaa cgcacccaat   1080
atgatcatat gtttagagaa tgggaagaaa aagaacttga gagtgaagac aacatagaag   1140
gatgggaaac cagtgtgtca agatatgaag ttaatttgtc tgatgaatct gctgcggcaa   1200
tggcacgtgt tcgagatcgt attgctcaaa ctatgtggac ggcttataat aatagaaatt   1260
agtcaattat attttaatgt ttgatgatac attcaggatt aaatttattt ttataaggat   1320
atattgtaga ctaatggtta ttttacatcg attttagatt aaaaaattct ttaagaattt   1380
cataattata tttttaagta ttataatatt atatttactt attatttaaa attatttttt   1440
taaataaatt agatattaat atgttattga attaaattaa aatttgtaat atttattttt   1500
ttaaaaaaaa aaacaacaca acaccaaaaa aataataata acagtaattt ttttatttat   1560
atatattttt ttaaaaaaaa gcaattttta aaaacttgtt gtttttacta tccaaacatg   1620
ttttcagttt ttgttgttta aaaactgttt ttaaaaaata ttagccaaac accatttaat   1680
ttttaaaatg acaaaaaact gttttctgtt ttcactttta aaaactgttt ttgaaaacta   1740
aaaactgaaa acacagccaa acagcctcta agagattccc ctttttttgta aattagcttt   1800
ggaagattgc acaatgaaca acttgatatt tgtttgggat cttaacccaa gagatatttt   1860
ctttaacaag tctagtgata ttttccacta ctaaattatt acaattatag gcaagtccaa   1920
tagagtcaat tccctccaat tggaattcaa aaccacaacg gtcatgacag ctggacccca   1980
cacccacatc cccacaacgg tcagtttcaa attttgaaac gtccccaaat tttttaaaaa   2040
ccgacttaaa aatttgtcct ttttataccc taaaaaaacc ctagctgctc aatcatattt   2100
tctcttgtaa aaaaaagtaa ccgaaaagcc taaaacagaa gaaaaagcaa aacctaaaac   2160
cagagaagag aa                                                       2172
```

<210> SEQ ID NO 9
<211> LENGTH: 3175
<212> TYPE: DNA
<213> ORGANISM: Cannabis sativa

<400> SEQUENCE: 9

```
agtgaactga caaatcaggg aataaacttt cgaacatata attaagatta tattccactg     60
tgttgacaac actataatca ttaacaaatt gatatgttct ggacttaaat agaattcata    120
cattatgtac atataatcat gaaataaatc atgtgaacca tgcaacatta aatgttattt    180
atgatctata ttaataagta aatctaatta tattgaaatg agttttattt agggcataaa    240
acccaacatt ttccaattgt aattgggggc aaagataaaa agaagtgcac aaatctggca    300
catattctca ctgaaagaag agagttcaca caaacaaagc agactaccaa aagtcgctag    360
agggagaaac catgcaagcc aacaagcaac actaaccaaa agaaagatct aatcgggcac    420
tgagctacac acaatcccct ccacaaccac acaaacaagc ctatgagcac gacaaaacaa    480
gaccacagct gaaccagaaa caagctccga gaaaccgaaa acaaaagacg agggaacacc    540
aagaatgaca agctacaaca tcagccagga acaatcccaa atctcatgaa agaacacaaa    600
aactctcaat cccgttacta gaacaccata cggggggaac tagaacatgg agaaagaagg    660
ctagaaatcc attcccaacg tcctgagaag ccaccggagc aacaccaact aagacaggat    720
cctgacgaaa ggacgagatt caaaatcgcc tagaacaaag agaactaaag gaaaaaggca    780
actaaagtga aagagctatt aagaacactg ctgaacaaaa ccacaatctc acgaccacta    840
aagcagtcac aaggagccag aaacagtgac ggaggaacga ctcaaagtct cacggcaaga    900
ctcaaaggga cgggaatgca aagcaaaatc gcaaattgta tggaaagaac aagggcaatt    960
tcggttttag cgagactagt atcattgtat agcttttgcc tatttgagga atttggatga   1020
tggcaagttt tctaaaaaga aatgaacata aaaataaaaa agaaaatgaa aaagttactg   1080
cccttttgag gaggcgaatc gtgacagaat cccacatgcg caagcgtcac ataaacgctg   1140
attaataaac atttgattct cttcaactca ttccatccaa cggtggaaaa tctccaattt   1200
ctcatcagat atatacattt ttattatttt atttaaatat tttgttttga aaccctaggt   1260
tttgtttgag atcaagtccg cagcactcct cctcattttc tttcacaaat attatttcaa   1320
aacttgtacc catatataaa ttgtctcatt tctcatcttc ctcaaccctt cttttctctg   1380
ccttcttcca ttttttgggg ttttcttctt cttcttcttc atcttttccg ctcaatcagc   1440
tatgtcggac gaggagcacc agtttgagtc caaggccgac gccggagctt ccaagaccta   1500
tcctcagcaa gctggtacta tccgcaagaa tggttacatc gtcattaagg gcaggccctg   1560
caaggttctc tttatcattt tccttttatc agattggatt cactacggat ctggaacttg   1620
gatttttatt ctttattatt tgttatttgt tccaaataag cgataagata aggttaaagt   1680
ttgatttttt ttttctcata atctttattg ggtttttgtt gttcgatgtt gttttggtat   1740
attggggttt gactgggctt gtggtagtga taagcgtctg tgctttatgt gatagctttc   1800
ggtcgaaaat gagaaatttg ttgtctggta ttagaaaatg ttggattcga aaccctttat   1860
taagtttctt attgcatgtt ttgggtcaat aatttaggga ttattgaaga tagcttgtta   1920
tttttccttt gtttctgttt cgtcgtggcg gttatatata actcacatgt ttggattgat   1980
ttaattaaac gaattattaa agaaaacttt tgatgcaaga aggatcttat catggaaatg   2040
attgtttatt gattctattg atgagtttat tattattgtt ctaaagaaaa tctttgactt   2100
tgcaatattt acaggttgtt gaagtttcca cttccaaaac tggaaagcac ggtcacgcta   2160
```

agtgtcactt tgttgccatt gatatcttca ctgcaaagaa gctggaagat attgttccat 2220
cttcccacaa ttgtgatgta tgatcattct ttgctcttct attttgtctt gtttgtgtta 2280
tcgttttgac accttttctt atctcacttt atccattctc gtgtcttttt attgcaggtc 2340
cctcatgtca atcgtactga ctaccagctg attgatattt ctgaggatgg atttgtaaga 2400
tttatttcct ttttttacta cttttgggtc atatttgttc accccttttct tgtattgttt 2460 cactagtcat ttcaacttgg gctaacttga gttatgatat tttaggtgag tctgcttact 2520
gataatggaa ataccaagga tgacctgaag cttccaactg atgacagtct gctcacgcag 2580
gtttgttgat atgaatgact tctgctaaat ctgtgtcaat atctctgtag acattgatgt 2640
gtcattaatt atgctctttt gggaattgat gtgtcagttt atctattctg gccttgcaac 2700
gctgatagaa atttttaggt ggtgattatt atagctaata attaatggtc atggctttgg 2760
aattgtacag atcaaggatg gatttgctga tgggaaggat cttgtcgtgt ctgtcatgtc 2820
tgcaatggga gaggagcaga tctgtgccct taaggacatt ggccccaagt agttcattgc 2880
gtgttgctct atcaaaactc aaaatgtttt tttatcttaa gaccataaat ttattgtgat 2940
acagctttgt tgttgatggt ggttttattt gctttgagaa tatgtggtca cgttttattt 3000
tatttttcct gcaaattatt ctgaatgaga tgttaccaaa attatcatat tcaacttcaa 3060 tattttttt aatgttgtat gaaccggcaa aacgtgcaat ccaatctttg tatttgtatc 3120
taatttgcca gtattggcaa attaagtcag ctattttgcc agtattggca gttaa 3175

<210> SEQ ID NO 10
<211> LENGTH: 1441
<212> TYPE: DNA
<213> ORGANISM: Cannabis sativa

<400> SEQUENCE: 10
agtgaactga caaatcaggg aataaacttt cgaacatata attaagatta tattccactg 60
tgttgacaac actataatca ttaacaaatt gatatgttct ggacttaaat agaattcata 120
cattatgtac atataatcat gaaataaatc atgtgaacca tgcaacatta aatgttattt 180
atgatctata ttaataagta aatctaatta tattgaaatg agttttattt agggcataaa 240
acccaacatt ttccaattgt aattgggggc aaagataaaa agaagtgcac aaatctggca 300
catattctca ctgaaagaag agagttcaca caaacaaagc agactaccaa aagtcgctag 360
agggagaaac catgcaagcc aacaagcaac actaaccaaa agaaagatct aatcgggcac 420
tgagctacac acaatcccct ccacaaccac acaaacaagc ctatgagcac gacaaaacaa 480
gaccacagct gaaccagaaa caagctccga gaaaccgaaa acaaaagacg agggaacacc 540
aagaatgaca agctacaaca tcagccagga acaatcccaa atctcatgaa agaacacaaa 600
aactctcaat cccgttacta gaacaccata cggggggaac tagaacatgg agaaagaagg 660
ctagaaatcc attcccaacg tcctgagaag ccaccggagc aacaccaact aagacaggat 720
cctgacgaaa ggacgagatt caaaatcgcc tagaacaaag agaactaaag gaaaaaggca 780
actaaagtga aagagctatt aagaacactg ctgaacaaaa ccacaatctc acgaccacta 840
aagcagtcac aaggagccag aaacagtgac ggaggaacga ctcaaagtct cacggcaaga 900
ctcaaaggga cgggaatgca aagcaaaatc gcaaattgta tggaaagaac aagggcaatt 960
tcggttttag cgagactagt atcattgtat agcttttgcc tatttgagga atttggatga 1020
tggcaagttt tctaaaaaga aatgaacata aaaataaaaa agaaaatgaa aaagttactg 1080 ccctttttgag gaggcgaatc gtgacagaat cccacatgcg caagcgtcac ataaacgctg 1140
attaataaac atttgattct cttcaactca ttccatccaa cggtggaaaa tctccaattt 1200
ctcatcagat atatacattt ttattatttt atttaaatat tttgttttga aaccctaggt 1260
tttgtttgag atcaagtccg cagcactcct cctcattttc tttcacaaat attatttcaa 1320
aacttgtacc catatataaa ttgtctcatt tctcatcttc ctcaaccctt cttttctctg 1380
ccttcttcca ttttttgggg ttttcttctt cttcttcttc atcttttccg ctcaatcagc 1440
t 1441

<210> SEQ ID NO 11
<211> LENGTH: 59
<212> TYPE: DNA
<213> ORGANISM: Artificial sequence
<220> FEATURE:
<223> OTHER INFORMATION: Sequencing results of DNA fragments
potentially containing mutations

<400> SEQUENCE: 11
tcatgacctg cacctgctag tatttcgcag tagataaacc agccaaacct acaagaatt 59

<210> SEQ ID NO 12
<211> LENGTH: 60
<212> TYPE: DNA
<213> ORGANISM: Artificial sequence
<220> FEATURE:
<223> OTHER INFORMATION: Sequencing results of DNA fragments
potentially containing mutations

<400> SEQUENCE: 12
tcatgacctg cacctgccta gtatttcgca gtagataaac cagccaaacc tacaagaatt 60

<210> SEQ ID NO 13
<211> LENGTH: 60
<212> TYPE: DNA
<213> ORGANISM: Artificial sequence
<220> FEATURE:
<223> OTHER INFORMATION: Sequencing results of DNA fragments
potentially containing mutations

<400> SEQUENCE: 13
tcatgacctg cacctgccaa gtatttcgca gtagataaac cagccaaacc tacaagaatt 60

<210> SEQ ID NO 14
<211> LENGTH: 60
<212> TYPE: DNA
<213> ORGANISM: Artificial sequence
<220> FEATURE:
<223> OTHER INFORMATION: Sequencing results of DNA fragments
potentially containing mutations

<400> SEQUENCE: 14
ttatgacctg catctgccaa gtatttcgca gtagataaac cagccaaacc tacaagaatt 60

<210> SEQ ID NO 15
<211> LENGTH: 60
<212> TYPE: DNA
<213> ORGANISM: Artificial sequence
<220> FEATURE:
<223> OTHER INFORMATION: Sequencing results of DNA fragments
potentially containing mutations

<400> SEQUENCE: 15
tcatgacctg catctgccaa gtatttcgca gtagataaac cagccaaacc tacaagaatt 60

<210> SEQ ID NO 16
<211> LENGTH: 1885
<212> TYPE: DNA
<213> ORGANISM: Artificial sequence
<220> FEATURE:
<223> OTHER INFORMATION: THC synthase gene Nucleic acid sequence

<400> SEQUENCE: 16

```
aaaaaaatca ttaggactga agaaaaatga attgctcagc attttccttt tggtttgttt     60

gcaaaataat atttttcttt ctctcattcc atatccaaat ttcaatagct aatcctcgag    120

aaaacttcct taaatgcttc tcaaaacata ttcccaacaa tgtagcaaat ccaaaactcg    180

tatacactca acacgaccaa ttgtatatgt ctatcctgaa ttcgacaata caaaatctta    240

gattcatctc tgatacaacc ccaaaaccac tcgttattgt cactccttca aataactccc    300

atatccaagc aactatttta tgctctaaga aagttggctt gcagattcga actcgaagcg    360

gtggccatga tgctgagggt atgtcctaca tatctcaagt cccatttgtt gtagtagact    420

tgagaaacat gcattcgatc aaaatagatg ttcatagcca aactgcgtgg gttgaagccg    480

gagctaccct tggagaagtt tattattgga tcaatgagaa gaatgagaat cttagttttc    540

ctggtgggta ttgccctact gttggcgtag gtggacactt tagtggagga ggctatggag    600

cattgatgcg aaattatggc cttgcggctg ataatattat tgatgcacac ttagtcaatg    660

ttgatggaaa agttctagat cgaaaatcca tgggagaaga tctgttttgg gctatacgtg    720

gtggtggagg agaaaacttt ggaatcattg cagcatggaa aatcaaactg gttgctgtcc    780

catcaaagtc tactatattc agtgttaaaa agaacatgga gatacatggg cttgtcaagt    840

tatttaacaa atggcaaaat attgcttaca agtatgacaa agatttagta ctcatgactc    900

acttcataac aaagaatatt acagataatc atgggaagaa taagactaca gtacatggtt    960

acttctcttc aatttttcat ggtggagtgg atagtctagt cgacttgatg aacaagagct   1020

ttcctgagtt gggtattaaa aaaactgatt gcaaagaatt tagctggatt gatacaacca   1080

tcttctacag tggtgttgta aattttaaca ctgctaattt taaaaaggaa attttgcttg   1140

atagatcagc tgggaagaag acggctttct caattaagtt agactatgtt aagaaaccaa   1200

ttccagaaac tgcaatggtc aaaattttgg aaaaattata tgaagaagat gtaggagctg   1260

ggatgtatgt gttgtaccct tacggtggta taatggagga gatttcagaa tcagcaattc   1320

cattccctca tcgagctgga ataatgtatg aactttggta cactgcttcc tgggagaagc   1380

aagaagataa tgaaaagcat ataaactggg ttcgaagtgt ttataatttt acgactcctt   1440

atgtgtccca aaatccaaga ttggcgtatc tcaattatag ggaccttgat ttaggaaaaa   1500

ctaatcatgc gagtcctaat aattacacac aagcacgtat ttggggtgaa aagtattttg   1560

gtaaaaattt taacaggtta gttaaggtga aaactaaagt tgatcccaat aatttttta   1620

gaaacgaaca aagtatccca cctcttccac cgcatcatca ttaattatct ttaaatagat   1680

atatttccct tatcaattag ttaatcatta taccatacat acatttattg tatatagttt   1740

atctactcat attatgtatg ctcccaagta tgaaaatcta cattagaact gtgtagacaa   1800

tcataagata tatttaataa aataaattgt ctttcttatt tcaatagcaa ataaaataat   1860

attattttaa aaaaaaaaaa aaaaa                                          1885
```

<210> SEQ ID NO 17
<211> LENGTH: 23
<212> TYPE: DNA
<213> ORGANISM: Artificial sequence
<220> FEATURE:

-continued

<223> OTHER INFORMATION: gRNA

<400> SEQUENCE: 17
cctcgagaaa acttccttaa atg 23

<210> SEQ ID NO 18
<211> LENGTH: 23
<212> TYPE: DNA
<213> ORGANISM: Artificial sequence
<220> FEATURE:
<223> OTHER INFORMATION: gRNA

<400> SEQUENCE: 18
ccaattgtat atgtctatcc tga 23

<210> SEQ ID NO 19
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 19
cactctcata gtttaactat ttcg 24

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
taagaaagtt caattagctt atgt 24

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27
<211> LENGTH: 2534
<212> TYPE: DNA
<213> ORGANISM: Cannabis sativa

<400> SEQUENCE: 27
actgtagtcg ttttttggag tagcaaatct agctgctgcc ctctttttct tcaattcccc 60
ctctgcctaa atatggaaaa gcatatgtat atatgctata gcttgcacac gtgtcacata 120
tttgcatata taatgctagc ccttccaatc atgggctgcc ccctttttttt ttctttttttt 180 ttttttttg tttctttatt attatttttt ttttttgcaa gcccattaga atagtaatta 240
tactttatga atattgtgta caagattttt gggctttgat agttcatgga cttttttact 300
ctatgacttt tgagacatta tgcacataat aaagtccaaa ctatatattt aagctcttac 360
aaaaatacac aatattaaga ataatacttt aacatgggaa actaaataaa attgataaaa 420
tattacaaaa attaactaaa attaatctaa aaatactaaa actaatattt atgcaaaact 480
aaataaaata attaaacagt cactaaaata aactaaaaat gcttgagaac aaaactaatt 540
taatggacaa aaagagctaa atagctctat tttcatagag ttatcaatag gcctatttgg 600
catttctctg acagtggttc tttctcggta aagagtggat attggagtac tgtgtccagg 660
ttgggtgggg ccaagcttca ggctcctctg gttcttcccg gtggtggaaa cttctttggc 720
agctgaatct tccgcctaag ataaaaaatt ttgtgtggaa ggcatgtctg aatttcattc 780
cggcttatgc caatttatct cgtcatggta tgaaggtttc tacaatatgt ccaatttgct 840
ctcaaaataa cgagactact cttcatgctc tttggctctg cccttctctt aagtctattc 900
gttcggtttg gtttttgagt gacctcgact ccttgaagga cgcctcttgc tattatgagt 960
tattattggg gtgtatggat atcttgaaac gacaggaact tgagcagttt ataacccttg 1020
gctagcatat ttggaacagg cgaaatacct ttgtgcatga tcataagctc ctctctgata 1080
acatggttag tgcttgggcc atggattatt tatggaaata tcaagatgct aataatgccg 1140
aggcagcttc tttgggttcg acttctagca atgcaagtaa tcgactggtc tcatctgaga 1200
cggatctggt tcttggtgag ttcaatcttt ttgtggatgc tggggtttgt gttgagaatc 1260
gaaaataggg atgggggctt tggtttccaa tcgtttgggg catgtcatat tctcgagtgc 1320
agctccttgc tccttgcgcg ggtttgtgtg aacctcacgt tgctgaagcc aaagctttgg 1380
tccatgagct ttcttgctgc gtgcagatgg ggtatacggt gattactgct ttctctgatt 1440
gtcaacgggt agagttcttg ctgtcaatag caggggccct tgtttcaata agtttggtat 1500
tgttcttaat gatattaatg atattaagaa ttctttcaat accatatctc tgtcgcattg 1560
taatcggtca aagaactatg atcctcattc tttagcaaaa cgagcgttag atttaaataa 1620
ggctcgggtg tggtggccga gcttgcctac tgatttagct gtttaaattt atctatctct 1680
tgtattctaa tcttttggct tgatggcttt taatagaatc tctctgtttt caagaaaaaa 1740
aaaataaata gattttatat atccattaaa agataaactt tttatatact aaaagtataa 1800
taatcatgat tgatgaccaa gtgcgcgaga tagacattag gacttatctc aaccggaacc 1860
gttgattata tctttgatca attaaagtca atcggacggt tgatacctta acgtcaacgt 1920
atagagaaaa ctctagacac atgtgccaac atctgagata aaaagggggg ccacgtggga 1980
gttagagcac cgtggatccc ttgattagca catgtacggt agagattgac tcgctcttgc 2040
tctataaaaa gaggtgcggt ttagttcatt tctgatttcg cactcaaaac tcgctctatc 2100
ttcaatcatc aaaaccgaat cttcctcatc tctgaagaaa atttgttatt tcaattcaaa 2160
ctatactcaa acatgtcttg ctgtggagga agctgtggct gtggatctgg ttgcaagtgc 2220
ggaagcggct gtggagggtg agtttttctt catttttttt aagttctaaa tcattgcatt 2280
gcatatttgc atggcctttg ttttactcct gaaacttttc cgattcttcg tatctttttt 2340
ttttttttct ttttcccaga tgcaagatgt accccgactt tggctacatg gagaaaacca 2400
ccacgtccga gactctcatc accggtgttg caccggcgaa gctacaattg gagggttctg 2460
agatgagcga ggtagcagag aacggatgca agtgtggaga caactgcaag tgcgacccat 2520
gcacttgtaa atga 2534

<210> SEQ ID NO 28
<211> LENGTH: 2172
<212> TYPE: DNA
<213> ORGANISM: Cannabis sativa

<400> SEQUENCE: 28
actgtagtcg ttttttggag tagcaaatct agctgctgcc ctctttttct tcaattcccc 60
ctctgcctaa atatggaaaa gcatatgtat atatgctata gcttgcacac gtgtcacata 120
tttgcatata taatgctagc ccttccaatc atgggctgcc cccttttttt ttcttttttt 180
tttttttttg tttctttatt attatttttt ttttttgcaa gcccattaga atagtaatta 240
tactttatga atattgtgta caagattttt gggctttgat agttcatgga ctttttttact 300 ctatgacttt tgagacatta tgcacataat aaagtccaaa ctatatattt aagctcttac 360
aaaaatacac aatattaaga ataatacttt aacatgggaa actaaataaa attgataaaa 420
tattacaaaa attaactaaa attaatctaa aaatactaaa actaatattt atgcaaaact 480
aaataaaata attaaacagt cactaaaata aactaaaaat gcttgagaac aaaactaatt 540
taatggacaa aaagagctaa atagctctat tttcatagag ttatcaatag gcctatttgg 600
catttctctg acagtggttc tttctcggta aagagtggat attggagtac tgtgtccagg 660
ttgggtgggg ccaagcttca ggctcctctg gttcttcccg gtggtggaaa cttctttggc 720
agctgaatct tccgcctaag ataaaaaatt ttgtgtggaa ggcatgtctg aatttcattc 780
cggcttatgc caatttatct cgtcatggta tgaaggtttc tacaatatgt ccaatttgct 840
ctcaaaataa cgagactact cttcatgctc tttggctctg cccttctctt aagtctattc 900
gttcggtttg gtttttgagt gacctcgact ccttgaagga cgcctcttgc tattatgagt 960
tattattggg gtgtatggat atcttgaaac gacaggaact tgagcagttt ataaccccttg 1020 gctagcatat ttggaacagg cgaaatacct ttgtgcatga tcataagctc ctctctgata 1080
acatggttag tgcttgggcc atggattatt tatggaaata tcaagatgct aataatgccg 1140
aggcagcttc tttgggttcg acttctagca atgcaagtaa tcgactggtc tcatctgaga 1200
cggatctggt tcttggtgag ttcaatcttt ttgtggatgc tggggtttgt gttgagaatc 1260
gaaaataggg atgggggctt tggtttccaa tcgtttgggg catgtcatat tctcgagtgc 1320
agctccttgc tccttgcgcg ggtttgtgtg aacctcacgt tgctgaagcc aaagctttgg 1380
tccatgagct ttcttgctgc gtgcagatgg ggtatacggt gattactgct ttctctgatt 1440
gtcaacgggt agagttcttg ctgtcaatag caggggccct tgtttcaata agtttggtat 1500
tgttcttaat gatattaatg atattaagaa ttctttcaat accatatctc tgtcgcattg 1560

```
taatcggtca aagaactatg atcctcattc tttagcaaaa cgagcgttag atttaaataa   1620

ggctcgggtg tggtggccga gcttgcctac tgatttagct gtttaaattt atctatctct   1680

tgtattctaa tcttttggct tgatggcttt taatagaatc tctctgtttt caagaaaaaa   1740

aaaataaata gattttatat atccattaaa agataaactt tttatatact aaaagtataa   1800

taatcatgat tgatgaccaa gtgcgcgaga tagacattag gacttatctc aaccggaacc   1860

gttgattata tctttgatca attaaagtca atcggacggt tgatacctta acgtcaacgt   1920

atagagaaaa ctctagacac atgtgccaac atctgagata aaaagggggg ccacgtggga   1980

gttagagcac cgtggatccc ttgattagca catgtacggt agagattgac tcgctcttgc   2040

tctataaaaa gaggtgcggt ttagttcatt tctgatttcg cactcaaaac tcgctctatc   2100

ttcaatcatc aaaaccgaat cttcctcatc tctgaagaaa atttgttatt tcaattcaaa   2160

ctatactcaa ac                                                        2172


<210> SEQ ID NO 29
<211> LENGTH: 5856
<212> TYPE: DNA
<213> ORGANISM: Cannabis sativa
<220> FEATURE:
<221> NAME/KEY: misc_feature
<222> LOCATION: (2516)..(2646)
<223> OTHER INFORMATION: n is a, c, g, or t

<400> SEQUENCE: 29

ataatgatat aataatattt aaatgatata aaaaacatat agaaaacttg atgtatatat     60

aaaagtgtga ggtgaaatag agaaggtaga gttttagtaa aatattttaa atgatagaat    120

agagaagttg ttaagagtcc tctaataatt gtaagtgtaa ttgtaattat aaataattcg    180

gttgtttctc tttaaaccaa ttttccaaag aggccctaca aagaagtctt tgatactata    240

tccaacggtt acactatttt agtgttttac actacatact aaaaatttta acttttgtat    300

tgtggaatgg aatttttttt tcgaaaatac tgtgtaagtt ttatattgtg tatagtgtta    360

aattttcaca attgttttac gattgttttt tacttgttcc attgttattt taattgtttt    420

gttttgttgt tttacgttgt tttataaaaa gacaatattt ttataaaaaa ttccatgtga    480

caataaaatt gtaaattttt atcaaaaatc tatattttta taaaaatcgc tatatttttt    540

tttttgaatg atttaataca aaaaaaaaaa aaaaattcat tacactcttt cgattgtctt    600

tctgcctctc ctctgttttc tccttaatat tttctgtcga tccttctttt tagcttggta    660

tcagagcagg tatggcatcc ccaggcgact cctcagtcaa caacgcaaga tctcaagctg    720

ttgaagctcc tcctccagct ccagcccctg caccagctgc tcaacctcta cctgcacctc    780

tgctgcagcc cctcacgcct atcacaatcc gcctggacag agacaactac ccatattggc    840

gctaaaaaaa aaaaaaaaaa taccacacta gatatgatac gaaacaaaaa tatctttttt    900

ttaaaaaaaa aatctcacat tacaaataaa attatattaa taatttatta ttacttttta    960

aaacaaacta aaaaaggtta gaaattacaa taaaaaacga caataataaa aagttatatg   1020

caacaattta gtccataatt tattttaggc taataaggat ttttgccccc taaattttaa   1080

catgtactaa attataccct tgaactttta aggtcgttaa aaatgatccc tgaactattg   1140

agattgttgg gtttaaggac tttttccaat tttagtaaaa aagtctaaca tggataaaaa   1200

ttcaagaggc ataatttaat acatgttaaa attcgagggg catgatttag tagatatcaa   1260

agtatatgaa ttatggttta gtacataaac aatcagtgaa atagtacaat tgaatgaaat   1320
```

-continued

```
taaataaaat tctttaaatt caacaatcta aaatagttta aacgatattt ttaactacct   1380
taaaagttaa agaagcatga tttaatacat gtcaaagttt aaggacaaaa atcctaatta   1440
atctttattt tatcttgtga aaattccaca ctaatttaca cacacccgtt caaatgttca   1500
tgagattgct attgtgggtg ggacctctag ttgtgtaatg tcactaaatt ttgtatttta   1560
gaattttgga taacattatt gataatagac attattgtgt tttcccctaa ataatggagt   1620
agggagtgat ttttcttttt ctttttcctt tttttttact gtactcatta taatgtcaac   1680
ttttactatt aataggataa atgtgaaaat ataattatta tgttattttt gaaaagtcta   1740
tggaggcttc tttataaata ctggtatttg aagtaaggtt tccacacgct tcaaaaccaa   1800
acctcactca ctcactcttt ttctctctct aaatcttgat ccaacctttg ctccatcttc   1860
aaacatggat ccttacaagg tattaatatt aattatattt ctttagtttt gttgtaataa   1920
taataatcta aacccctaat actttagttt gtttatttaa ttaaaccaac atcatgatca   1980
gcttttcatc ttcttctgta tttatttttt taatccaaat aaaataaaag aaagagtgag   2040
agagaatatc tgatctgagt ttattagtca gtttacaaat cttattttaa tttgatccat   2100
agttaaaata tattattaaa gctaaagttg gcatacataa tatatataaa ctataattac   2160
actatatgac actaatttat atacgtaagc tgatctgtac taatactagc ttgatctaga   2220
gactaaaaat aaaattattg ttattattat aataataata aaagtaataa ttaaaaagaa   2280
aaagaaatac tagtttattt tgtagtttag attgaattta ttattaatat taattataat   2340
ttgaagatga tgattatatt ataagctatt aatgaagatt tggtgtttgg atataaaaca   2400
gtatcgacca tcgagtgctt acaacgcacc gtttatgact acaaatgccg gagctccggt   2460
ttacaacaat gagtcggctt taactgtcgg acccagaggt atttttcgg cgaaannnnn   2520
nnnnnnnnnn nnnnnnnnnn nnnnnnnnnn nnnnnnnnnn nnnnnnnnnn nnnnnnnnnn   2580
nnnnnnnnnn nnnnnnnnnn nnnnnnnnnn nnnnnnnnnn nnnnnnnnnn nnnnnnnnnn   2640
nnnnnnttgc aactcgcacc tatgcatata cacatggtta tcaaattata gtttttaaag   2700
gattttccta cgaaaaaaat aaaaaactat acatataaaa attaaaatct aaaaagagat   2760
tttaccgcta ataatttttt atacatataa atatttggat ttttatcaat atatatttat   2820
atatatgtct ggataactct atctatgtcc ataattaaga agtttggact cattatatgt   2880
acacaatcta ctaaaattac atatagtgac gtttggtttg ttttatttta ctaaaattaa   2940
atatataaat atgttttaaa aattatctta ttttgaaagc caagatccat cacgtttttt   3000
ttctttacat taaatactcg gactatctca atcagatcat gttttttatt gtttgataaa   3060
gaaaatcaga ttgtatctgc tatataaaat aaagttttgt acataattat taaatatatt   3120
tattaaaata tataaaaccc actaatgaaa tcatatgcct tcttttaagg tgcgtttata   3180
actatttatt tagacacata tttaaataaa ttgtacaaaa tattttacct acaataattg   3240
catcagttta atttgtatca atttatatca aaaataggtt tataactagt tctggaatac   3300
catatattta attttttttt tatttgtatt tcaaacaaaa aggaagaaat tttaaagcat   3360
ttagcaaacc taatcagtaa aaaaagctaa aaacaaacaa aatatcatta aaaaaaatgg   3420
acaaaattaa atctgcaaaa attttttaaa ctcttatata taatttcctc tttttttaaat  3480
ttaaatatta atttggcgtg gcactcgtgg acatgcaatg caattgagct tgtgatttgt   3540
tttttcgatc cttcacgcaa ttaaacgtta taaataaaat ggaggtgatt taatttggat   3600
agttgcagtt gataaacatc tgtgaataat ttactgtagt tgatgattaa tcttcgtaat   3660
tcagatacaa gatatgttga tgatttttac cgaagaaaaa ttattgagtc tctttaacgt   3720
```

```
gtttgacaaa ttaaaggtgt gaatgaaaat gttgatgttg ttgtttgaca ggtccaatcc   3780
tgttggagga ttatcatctg gtggagaaga ttgctaactt caccagggaa aggatgccag   3840
agcgtattgt ccatgccagg ggagccagtg ctaagggttt ctttgaggtg actcatgatg   3900
tttcaaacct cacctgtgct gacttcctcc gagctcctgg ggttcagaca cctgtcattg   3960
ttcgtttctc cactgtcatc cacgaacgtg gtagtcctga aactatcaga gaccctcgtg   4020
gttttgcagt caagttttac accagagagg tagataataa aaagctttcg agttttactt   4080
gtgctctaaa tcgtattcca tataacatgt tacactgtta ttactttttc atggttgcag   4140
ggtaatttcg atattgtggg aaataacttc cctgtgtttt tcatccgtga tggaatccaa   4200
ttccctgatg tgatccatgc ttttaaacca aaccccaagt ctcacatcca ggagtattgg   4260
agggtgcttg acttcttgtc attccatcct gaaagtatgc tcacctttgc ctggctattc   4320
gatgatgtgg gtgttccaca agattacagg cacatggaag gctttggtgt tcacaccttt   4380
actttagtca acaaggctgg aaaggtaact tttgtcaagt tccactggaa gcccacctgt   4440
ggtgttaagt ccatgttgga ggaagaggcc attagggttg gaggaaccaa ccacagccat   4500
gccacccaag atctttatga gtcaattgcc tctggaaact accctgagtg gaagctctac   4560
atccaaacac ttgatcctgc tgatgaggac aagtttgact ttgacatact cgacacaaca   4620
caaatctggc cagaggacct cattcctctt cacccagttg gtcgtttggt tctcaacagg   4680
aacattgaca atttctttgc agagaatgaa caactcgcca tgaaccctgc ccataccgtc   4740
cctggtatcc actattccga tgacaagatg cttcaggctc gtctctttgc ttacagtgat   4800
actcacagat accgtattgg agtgaactac cttcaactcc ctgttaatgc tcccaagtgt   4860
gcccaccaca acaatcacta tgatggttgc atgaatttca ctcacagaga tgaggaggta   4920
acactcacat tattcctcca acaaactcat atactttgct tctttgcttc tttgcttatt   4980
catatattat ttagttggct ctactaatca catactgttt tttctttttc acttctttgt   5040
tatagattga ctacttccct tcaaggtatg ataccgttcg ccatgctgaa aagttcccca   5100
ttcctgctaa aatcatccat ggaaagcgtg aaagggtaat tcttccatca ccaaactcaa   5160
tatatagtaa aagtaactcc ttactaatac tttggtatat gtgttacttc tctttttggt   5220
gaatacagtg tactattcca aaggaggaca actttacaca agctggtgtg agataccgat   5280
cttgggcacc agacaggtac atgcatatgt ggtcatttta ccatgtcaaa aacagtattg   5340
aagtgtttgg tttcatttgt atgcaattca ccaatgtaga ttttgactaa ctttcttctt   5400
acattacatc tatgcagaca agacaggttt gtgaagcgat gggtggatgt gttggctgac   5460
caccgtgtca cccatgagat ccgcagcatc tggatctcct acttgtctca ggtcagtttc   5520
caaccaatct acttctgtta acactgttga ataatgttca tttgctgatg ttatgtattg   5580
gtgtcggttt gtacaggcgg acaagtctct cggtcagaag gtagcttccc gtctcaatgt   5640
taggcctaac atttgagagt ggacagcagg cacgtatgca agatgttttt aagattcgaa   5700
atatgcaaga aggaactaaa tggcgaaaag tgcagattat aaatatggaa tgatgaataa   5760
ctcctgtgta ctatcttgtg tacttttctt ctgtaatctt atgttttgtg ttgttatatt   5820
atgttatgta actctttatg tacactattt attaaa                             5856
```

<210> SEQ ID NO 30
<211> LENGTH: 1864
<212> TYPE: DNA
<213> ORGANISM: Cannabis sativa

<400> SEQUENCE: 30

```
ataatgatat aataatattt aaatgatata aaaaacatat agaaaacttg atgtatatat     60
aaaagtgtga ggtgaaatag agaaggtaga gttttagtaa aatattttaa atgatagaat    120
agagaagttg ttaagagtcc tctaataatt gtaagtgtaa ttgtaattat aaataattcg    180
gttgtttctc tttaaaccaa ttttccaaag aggccctaca aagaagtctt tgatactata    240
tccaacggtt acactatttt agtgttttac actacatact aaaaatttta acttttgtat    300
tgtggaatgg aatttttttt tcgaaaatac tgtgtaagtt ttatattgtg tatagtgtta    360
aattttcaca attgttttac gattgttttt tacttgttcc attgttattt taattgtttt    420
gttttgttgt tttacgttgt tttataaaaa gacaatattt ttataaaaaa ttccatgtga    480
caataaaatt gtaaattttt atcaaaaatc tatattttta taaaaatcgc tatatttttt    540
tttttgaatg atttaataca aaaaaaaaaa aaaaattcat tacactcttt cgattgtctt    600
tctgcctctc ctctgtttc tccttaatat tttctgtcga tccttctttt tagcttggta    660
tcagagcagg tatggcatcc ccaggcgact cctcagtcaa caacgcaaga tctcaagctg    720
ttgaagctcc tcctccagct ccagcccctg caccagctgc tcaacctcta cctgcacctc    780
tgctgcagcc cctcacgcct atcacaatcc gcctggacag agacaactac ccatattggc    840
gctaaaaaaa aaaaaaaaaa taccacacta gatatgatac gaaacaaaaa tatctttttt    900
ttaaaaaaaa aatctcacat tacaaataaa attatattaa taatttatta ttacttttta    960
aaacaaacta aaaaaggtta gaaattacaa taaaaaacga caataataaa aagttatatg   1020
caacaattta gtccataatt tattttaggc taataaggat ttttgccccc taaattttaa   1080
catgtactaa attatacctt tgaactttta aggtcgttaa aaatgatccc tgaactattg   1140
agattgttgg gtttaaggac tttttccaat tttagtaaaa aagtctaaca tggataaaaa   1200
ttcaagaggc ataatttaat acatgttaaa attcgagggg catgatttag tagatatcaa   1260
agtatatgaa ttatggttta gtacataaac aatcagtgaa atagtacaat tgaatgaaat   1320
taaataaaat tctttaaatt caacaatcta aaatagttta aacgatattt ttaactacct   1380
taaaagttaa agaagcatga tttaatacat gtcaaagttt aaggacaaaa atcctaatta   1440
atctttattt tatcttgtga aaattccaca ctaatttaca cacacccgtt caaatgttca   1500
tgagattgct attgtgggtg ggacctctag ttgtgtaatg tcactaaatt ttgtatttta   1560
gaattttgga taacattatt gataatagac attattgtgt tttcccctaa ataatggagt   1620
agggagtgat ttttcttttt ctttttcctt tttttttact gtactcatta taatgtcaac   1680
ttttactatt aataggataa atgtgaaaat ataattatta tgttattttt gaaaagtcta   1740
tggaggcttc tttataaata ctggtatttg aagtaaggtt tccacacgct tcaaaaccaa   1800
acctcactca ctcactcttt ttctctctct aaatcttgat ccaacctttg ctccatcttc   1860
aaac                                                                1864
```

<210> SEQ ID NO 31
<211> LENGTH: 6146
<212> TYPE: DNA
<213> ORGANISM: Cannabis sativa
<220> FEATURE:
<221> NAME/KEY: misc_feature
<222> LOCATION: (793)..(1585)
<223> OTHER INFORMATION: n is a, c, g, or t
<220> FEATURE:
<221> NAME/KEY: misc_feature
<222> LOCATION: (2423)..(2597)
<223> OTHER INFORMATION: n is a, c, g, or t

<400> SEQUENCE: 31
aataaaaaat atttaaatat ttggataata aaaataacat caatatattt atcaattaaa 60
gttcactgaa aatttacctt ttattcaaaa aaaaaaaaaa gaaaaaagta tagcttgctt 120
tcagtttcta ctttctaaat aaaataccta tttactttta atattaatga gtatttactt 180
taaatgttta atgtggaaaa gaggaaaagt caatttcaat aaatgaatat ttattacaag 240
tgtcagattg taatagatta cacaaaatta gacagtagat ttaaatccat tattcctttc 300
tgaccggatt agaaagaaat gttcaaaagc tgagtcagca ttgtcaagta ggggaagtta 360
atcttacttt catggaaatg gataaacctt accttggtgc atgaccggga aacttggaga 420
cccaagagaa aatagaaaga gcattgatac gccaccttaa actactccct accttatccc 480
ataacacata atattttttt ttcttttttt ttttttaaac gaacacatga tattattatg 540
tactcacatt aactcacaca tgataattaa atataattat cttatagagt attctacact 600
ataaatgggc aattatcaaa tagaaaaatt tattatttga gtattactat gacatactct 660
aaaccactga acaccttaat taaaacatta ataaaattta cataaaccaa atttttttaa 720
aaaaatatta taaaaattca tcaacgaaac atgatcattg ttttttactt tctctctctt 780
tcttttcacc cgnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnntaata taataatttt taagaagtat tattaactaa 1620
gagaagttta aagatgctag acacaagtag tttcttagct ctataaaata agatgttagc 1680
attttctatt attatttaaa tgtatattat taaataaata aaaaagagag aggtgaagag 1740
aacaaaccat gtgagaacac gtggcaaaaa cggagaggag aagagagggt gtgggggcag 1800
gatggggttg taaacattgg tagtgacgac gccgtttgat ggtcacacta ccactataaa 1860
tacgtggctt gagatgggga gtttattact ataatcttca tattccaact ccttccctcc 1920
cccactcata atatacgtgt tgctcttctc ccttatttcc actcctgcca cctttgtctt 1980
cttctatatc cataaccaaa aattttcaat tcaaaatgtg tggaatactt gctgttcttg 2040
gttgctccga tgacactcag gccaaacggt tccgtgttct tgagctttca cgcaggcaat 2100
taccattcct ttatattaac ttgatttgtt tcatttcttt ctatagagac cgagaaaaaa 2160
tccattactt ttgtggttgg gcgtgtgtgt gtgcgtcaga ttcaaaatct agttaaacaa 2220
acggtttgaa gccctttttc ctatttattt cccaagatcg gctttccttt ttttctttcc 2280

-continued

```
ttttttttt ttttttatct cattcgctta atactttttc caatttttat cttagaattt   2340
agataaagtg ggattaaagt atatgaaatt ctatttcaaa attaattgtt aataggaaga   2400
ataatttatt tatcttatat atnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn nnnnnnnnnn nnnnnnnnnn nnnnnnnnnn nnnnnnnnnn   2580
nnnnnnnnnn nnnnnnnact tgtacttcca taaggcatat atcatggtcc cgcactagag   2640
ttacttctag ctaagaccaa aaatatatat gtcattacca ttcaaataaa acacacgatt   2700
atatcaatca tggtagtatt agtatacact aatttaaaat ttcggatcga agagctagtt   2760
tatagggaat cccaaagtga ataattggaa ttaaaataga attgtgtcat tatccaattc   2820
tttctctaat tttgattaag ataaagcatg tggggagtgg ggtccattaa tgaaagtgtg   2880
gtttagaact acttgtacaa tttgattttg tcgttaagat ttaactgata gggccttcta   2940
ctactacgta cctacctgga ccaggatttg gagtctaggc gtccgtacgt gcaaaacagt   3000
agtaatataa agaacagaat taatgagtgg tagtactgac tataattaca ctgttgtaat   3060
gtgtaccata cagattgaag caccgtggtc cagactggag tggtctatac cagcacggtg   3120
actgttactt agctcatcaa aggctagcca tcattgaccc tgcttctggg gaccaacccc   3180
tcttcaatga agacaaatct gttgttgtta cagtaagtcc atcatatctt ccaaccttgt   3240
tattttaaaa tgtttgattt atgaatatta atatggtgtc tgaaaaaacc aggtgaatgg   3300
agaaatctat aaccatgagg aactcaggag ccgtctcccc aaccacaagt tcagaaccgg   3360
aagtgattgt gatgttattg ctcatttggt cagtaggcag tctaaaaatt ttgttactaa   3420
atttcccaca caaattatta gattgatttt ttgaaaaaaa ttcttttatc ttatgtagta   3480
tgaggagttt ggggaagatt tcgttgacat gcttgatggg attttcgctt tcgtgttgct   3540
ggacacccga gacaacagct tcattgctgc tcgtgatgct attggagtta ctcctctcta   3600
tattggatgg ggactagatg gtattagttt tagtatattt actctgtttt acatggtgaa   3660
acttatgttt ctttttctat gtttggtaag tgaggatgaa atgaatgatc gttgtgtttt   3720
gaattttgta ttcaggatcc atttggatat catctgagat gaagggctta aatgatgact   3780
gtgaacattt tgaggtcttt cctccgggtc atttgtactc aagcaaacaa ggtggattca   3840
ggcgttggta caacccacca tggttctctg aggctgttcc atcaacccca tatgatccac   3900
ttgttcttag aaaggctttt gaggatgtaa gattctagtc aattctgatt ttatttagaa   3960
ttaagtcaac ttcgttttg ttttgacaaa ataacttatg tattgaaaca taacacatgc    4020
aggctgttat caaaaggttg atgacagatg tgccttttgg tgttctactc tctggtggct   4080
tggattcatc gttagtcgcc tccatcactg ctagacactt agcaggcacc aaagctgcca   4140
agcaatgggg aacacagctc cattctttct gcgttggttt agaggtaaat tacttattca   4200
aaaggactca acatcacatg cctacttttt ctttattttg tacttggtat taagatcttc   4260
aacctttaca attgtgagca gggttccccc gatttaaagg ctggaagaga agttgcagac   4320
tatttgggga cagttcacca tgagttccac tttaccgttc aggtaataac aataacaacc   4380
tctattatgt tgcttaatag ataactaaca tactatattt attttaatat gtaaacaatt   4440
ttgcgatttg tgtgtaccgc aggatggaat agatgcaatt gaggatgtga tttttcacat   4500
tgaaacttat gatgttacca caattcgtgc tgctacaccg atgtttctta tgtccaggaa   4560
gatcaaatct ttaggtgtta aaatggtgat atctggggaa ggctctgatg agatctttgg   4620
tggctacttg tacttccata aggcaccaaa caaggaagag tttcaccaag agacctgcag   4680
```

```
aaaggtactt ggtttttctt cattttggcc tgctatatgt ggcttaacta cgtgtgtgtg   4740

tttatgaaag atcaatgact ttattactct ttacctttca gattaaggca ctgtgtttat   4800

gaaagatcaa tgactttatt actctttacc tttcagatta aggcactgca tcagtatgac   4860

tgcttgaggg caaacaaagc aacatcagcc tggggtttgg aagccagagt cccattccta   4920

gacaaagcat ttatcaacac tgcaatggct attgatcctg aggctaaaat ggtaacatag   4980

tttgctttgt ttggttttaa gatgccttta gtttgattat tttttaacat ggtcaaacta   5040

cagaggccaa tgttaatcaa cctgtattga atttcagata cacccagaag aaggaagaat   5100

tgaaaagtgg gtgcttagaa gggcctttga tgatgagaag caaccctatc tgccaaaggt   5160

gaaactcttt tcccaacttg tattatcaga tgccttctta tataacttct tattttcccc   5220

cttttctaac tattgtttct atgtgattcc ttgcagcata tcctgtacag gcaaaaagaa   5280

cagtttagtg atggagttgg atatagctgg attgatggcc ttaaagatca tgctgctaaa   5340

catgtagaat agcctcttta acttgtttta ttcacttgtc atttttgaaa atgaaaccac   5400

tattatcttg gaaactcact tgaaatctta tcattcttgc tcatttgtac tcacaggtaa   5460

ctgacaaggt gatgcaaaat gctggaaata tcttcccaca caacactccc accacaaaag   5520

aagcatacta ctaccgaacc attttcgaaa ggttcttccc acaggtaaaa ataacacaaa   5580

gattaactta acttgtgctt ctgtcattat gctcttctgt attaacttgt gctattggat   5640

ttttgcagaa ctcagctcgg ctgactgtac caggggggagc aagtgttgcc tgcagcacag   5700

cgaaagccgt tgagtgggac gcttcatggt ctaaaaatct cgatccatct ggcagggccg   5760

cccttggagt ccatgtttct gcttatgaca actcttctgc taatagtggg gtggttcaac   5820

ctgtgatcat taacgatgta ccacatattt cagtgagcac tcatggtgtt gagatcctca   5880

gctagtaaaa tcttacacat aatgatgcta gatggaataa tactactact aataataata   5940

atgatttgta agtctactga ggctagaatt taagatgagt tctttccttc ctctgccttg   6000

acttggcata tattatcgta taggcagtat gtaaaaattt gagagagtag tactctctct   6060

gtgctatggt gacttgaaat atatatgtta tccttgtatt ggtgttcata atataagaag   6120

tgacactttc ttttgctttg ggtaca                                        6146


<210> SEQ ID NO 32
<211> LENGTH: 2015
<212> TYPE: DNA
<213> ORGANISM: Cannabis sativa
<220> FEATURE:
<221> NAME/KEY: misc_feature
<222> LOCATION: (793)..(1585)
<223> OTHER INFORMATION: n is a, c, g, or t

<400> SEQUENCE: 32

aataaaaaat atttaaatat ttggataata aaaataacat caatatattt atcaattaaa     60

gttcactgaa aatttacctt ttattcaaaa aaaaaaaaaa gaaaaaagta tagcttgctt    120

tcagtttcta ctttctaaat aaaataccta tttactttta atattaatga gtatttactt    180

taaatgttta atgtggaaaa gaggaaaagt caatttcaat aaatgaatat ttattacaag    240

tgtcagattg taatagatta cacaaaatta gacagtagat ttaaatccat tattcctttc    300

tgaccggatt agaaagaaat gttcaaaagc tgagtcagca ttgtcaagta ggggaagtta    360

atcttacttt catggaaatg gataaacctt accttggtgc atgaccggga aacttggaga    420

cccaagagaa aatagaaaga gcattgatac gccaccttaa actactccct accttatccc    480
```

ataacacata atattttttt ttcttttttt ttttttaaac gaacacatga tattattatg 540
tactcacatt aactcacaca tgataattaa atataattat cttatagagt attctacact 600
ataaatgggc aattatcaaa tagaaaaatt tattatttga gtattactat gacatactct 660
aaaccactga acaccttaat taaaacatta ataaaattta cataaaccaa atttttttaa 720
aaaaatatta taaaaattca tcaacgaaac atgatcattg tttttttactt tctctctctt 780 tcttttcacc cgnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnnnn nnnnnnnnnn nnnnnnnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn nnnnnnnnnn 1440
nnnnnnnnnn nnnnnnnnnn nnnnnnnnnn nnnnnnnnnn nnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnntaata taataatttt taagaagtat tattaactaa 1620
gagaagttta aagatgctag acacaagtag tttcttagct ctataaaata agatgttagc 1680
attttctatt attatttaaa tgtatattat taaataaata aaaaagagag aggtgaagag 1740
aacaaaccat gtgagaacac gtggcaaaaa cggagaggag aagagagggt gtgggggcag 1800
gatggggttg taaacattgg tagtgacgac gccgtttgat ggtcacacta ccactataaa 1860
tacgtggctt gagatgggga gtttattact ataatcttca tattccaact ccttccctcc 1920
cccactcata atatacgtgt tgctcttctc ccttatttcc actcctgcca cctttgtctt 1980
cttctatatc cataaccaaa aattttcaat tcaaa 2015

<210> SEQ ID NO 33
<211> LENGTH: 4128
<212> TYPE: DNA
<213> ORGANISM: Cannabis sativa

<400> SEQUENCE: 33
ataatttctt ttcgtcatga atgtaatatt tattctctag taatgtaata tttatgttat 60
tgtaatatga tattttaatt tattgagttt cgccgatttt acagtattat tatctttaat 120
ctaattaata agtttattta aattattagt taaatataac aattgtgata atttttttaa 180
ttaatataat atatttttta ttttattaaa aaattaatat aataataagg aatattattt 240
agtttaattt ttagtactat ggttatagta gaaatatttt ttgacgcaaa atttggtgat 300
agtaatacca tatttagctt atccttagag atgctcttag taaaatttta gtaattgaat 360
aaaggttaat taagattttt gccccttgaa ctatgacatg tactaaatca tgccctctga 420
acttttcaag tcgttaaaaa ttccccatga actattgaaa ttgttagatt taaggactta 480
tgtccatttt tattcaattt tgctaatgtg aaaattgtcc atgtactaaa ttatacctct 540
ctaactttaa tatctactaa atcatgccct ctgaacctta acatgtacca aattgtgccc 600

-continued

```
ctaaattttt atccacgtca gacgtttttt tagtaaaatt agacaaaagt ccttaaatcc    660
aataatttca atagttcatg gagaattttt aacgacctga aaagttcagg ggtaaaaatc    720
caaattagcc tataccaaat catgctcctc gaactttgac atgtactaaa tcatgccctt    780
gaactttcat ccatatgaga ctttttttact aaaatcggac aaaagtcctt aaattcaaca    840
atctcaatag ttcggggcaa aaattctaat tagccttgaa taaatgttat attttctatg    900
attttatata aaaaaaataa gggtaaatag cggcaaaagt acccaaagtt ttatgtttgt    960
aagcggcata agcccaatgt ttatttttag cggcataagt acccaatatt tgtaaaactg   1020
caattttttct ctaaatttat cagtacaaac tctgtcattg tcttaaacaa agcacatata   1080
aggcctaaat tctttttttt tttttttttt ttttttttg tagggtaacc gatacaggtt   1140
aaaataacaa aggtaacaaa gttacacaac cagaggagaa ttttcttcca tctataatag   1200
tttattgtct atcctaagag catgcagaga taccctagga gagctagaca ataaaaccat   1260
aatatcagaa aagaaaacct caaaactgag agttgtcact tccgaaccac tagtaaaaca   1320
cctgcaaaat aaagagaaat taattaatac ataataaata tttaataaaa aaatgaaatt   1380
tcccttataa ataaaataaa ataaaatatg aaattttata taaatagtca catagaattc   1440
tctgacgtag atacttatat gaaattttat atgaaatttt atatgtagta tgagttactt   1500
ccaaatgttc tcttaataaa tttaaaacag agtctgtact gacaaaactg taagaaaatt   1560
atagttttac aaacattagg tacttataac gctaaaaata aaatttgggg tatttatgct   1620
actatttacc aaaaaaaata ataataaaaa aagtttatat tttctctaaa aatatagaat   1680
ggggggagtg taagaaacat aaacctaaca aataggctga aatggaaaag aagaaggccc   1740
atattgagat atgagaatgg gggctatact taatttaagc taaatatagg atctgtctgc   1800
aaaataagta ctataaaaac atatctaggg ttttagtcgt aacccttcag tctggtgtgc   1860
tagttcagct ctaccttcgc cgcacgagaa gctcaggttt ccttcccttt tctctcttct   1920
ctgtctctgc ttcgtatgtg tttttctcta agataacgaa aatggaaatg aacttctttc   1980
tgttcattct cctacatttt gtgatgatac acactgtgtt ttagcaacat ttcttgtact   2040
ctcgttagtt tgtgttagtt catattagat ctggattcat gggttttcat tagattgttt   2100
tatatgtttg aggataagaa aataatgggt tttgattctt ttgttgcatt tctgttttag   2160
cacttaaaat ttagagcttt tttgtttaac ttttaatttg attatattct tatgaaacta   2220
tatttgttat tgccagtagg aagaagagaa tgtctcacag gaagtttgag caccccagac   2280
atggttctct tggatttctt ccaaggaaga gagctgcccg tcacagagga aagggtaagt   2340
tatttcttgt gtattttagt atttactttt gatttttttt attacatata cataaatgat   2400
tgaatagatt tagtttgttc aaatgtttaa attctcattt tcaatttatg tatgataaat   2460
ttagattagt tctattgata aatagttcat ttaaacgttg ttctggattg tatactatta   2520
cattgtttca ttgggttttt agaatctaat agcctttttgt tatattttgt atttgtgcag   2580
tgaaggcttt ccccaaggat gacccagcta agccctgcaa gttgactgcc tttttgggat   2640
acaaggctgg catgacccac attgttaggg aggtggagaa gcctggatca agtaattgac   2700
tttcaaatga tttaattttt tcttaaaact tgtttcattt gtctttttgt cttatgaatt   2760
tttgttttaa tttggttaga gcttcacaaa aaggagacat gtgaagctgt gactattgtt   2820
gagacacccc caatggttat tgttggtgtt gttggttacg tgaagactcc acgtggtctt   2880
cgtaccctga acaccgtctg ggctcagcat ctgagcgagg aggtgaagag gaggttctac   2940
```

-continued aagaactggt gcaagtccaa gaagaaggcc ttcaccaagt actccaagca atacgaaaac 3000
gaagaaggaa agaaaagcat tcaagctcag cttgagaaga tgaagaagta tgctactatc 3060
attcgagttt tggctcacac tcaggtactt tcacaatctc tgttattgtg ctgttgtgat 3120
tttacttttt tcattttgaa tctctggtga tgtatctgtt ttgctgtgta tattcagatc 3180
aggaaaatga agggtttgaa gcagaagaag gctcacctta tggagattca ggtcaatggt 3240
ggttccattg cccagaaggt ggactttgct tatggtttct tcgagaagca agtccctatt 3300
gatgctgtct tccagaagga tgagatggtt gacatcattg gtgtgaccaa gggtaagggt 3360
tacgaaggtg ttgttaccag gtggggagtt acccgtcttc ctcgtaagac tcacaggggt 3420
cttaggaagg ttgcttgtat tggtgcctgg catccagcca gagtgtcctt cacagttgct 3480
agggctggac agaatggata ccatcaccgt accgagatga acaagaagat ctacaagctc 3540
ggcaaggttg gacaggagtc ccacactgct tccactgagt ttgacaggtt agtaaaatga 3600
ctgattattt ataattcgac aggagtccca cactgcttcc actgagtttg acaggttggt 3660
aaaatgactg attatttata gtttgaacaa gggattgaat tggctttcta tttcgtcgtt 3720
agacaattct aacttaattt tttatatttt aggaccgaga aggacatcac tcccatcggt 3780
gggttccctc attatggtgt ggtgaaggat gactatctga tgatcaaggg aggatgtgtt 3840
ggacattaga atttaccttt aaaatcgtcg catttattta tttatttgca ataaaggtga 3900
aaaggtgata cttaccatat ttgtgaaaga attttgggct atcaaagtaa aactaggaaa 3960
gtttcagttt ttatgcttgt gagattatgt ggagacagtt ttgatttagt ttttatgtat 4020
tttgaatatt taatactgcc tttgatgcat gtgagaatct attggttttc gtcagaatta 4080
atataatcaa ttttcttttt agtttatttg cttatgtctt gttggata 4128

<210> SEQ ID NO 34
<211> LENGTH: 2249
<212> TYPE: DNA
<213> ORGANISM: Cannabis sativa

<400> SEQUENCE: 34
ataatttctt ttcgtcatga atgtaatatt tattctctag taatgtaata tttatgttat 60
tgtaatatga tattttaatt tattgagttt cgccgatttt acagtattat tatctttaat 120
ctaattaata agtttattta aattattagt taaatataac aattgtgata atttttttaa 180
ttaatataat atatttttta ttttattaaa aaattaatat aataataagg aatattattt 240
agtttaattt ttagtactat ggttatagta gaaatatttt ttgacgcaaa atttggtgat 300
agtaatacca tatttagctt atccttagag atgctcttag taaaatttta gtaattgaat 360
aaaggttaat taagattttt gccccttgaa ctatgacatg tactaaatca tgccctctga 420
acttttcaag tcgttaaaaa ttccccatga actattgaaa ttgttagatt taaggactta 480
tgtccatttt tattcaattt tgctaatgtg aaaattgtcc atgtactaaa ttatacctct 540
ctaactttaa tatctactaa atcatgccct ctgaacctta acatgtacca aattgtgccc 600
ctaaattttt atccacgtca gacgtttttt tagtaaaatt agacaaaagt ccttaaatcc 660
aataatttca atagttcatg gagaattttt aacgacctga aaagttcagg ggtaaaaatc 720
caaattagcc tataccaaat catgctcctc gaactttgac atgtactaaa tcatgccctt 780
gaactttcat ccatatgaga ctttttttact aaaatcggac aaaagtcctt aaattcaaca 840
atctcaatag ttcggggcaa aaattctaat tagccttgaa taaatgttat attttctatg 900
attttatata aaaaaaataa gggtaaatag cggcaaaagt acccaaagtt ttatgtttgt 960
aagcggcata agcccaatgt ttatttttag cggcataagt acccaatatt tgtaaaactg 1020
caatttttct ctaaatttat cagtacaaac tctgtcattg tcttaaacaa agcacatata 1080
aggcctaaat tctttttttt tttttttttt tttttttttg tagggtaacc gatacaggtt 1140
aaaataacaa aggtaacaaa gttacacaac cagaggagaa ttttcttcca tctataatag 1200
tttattgtct atcctaagag catgcagaga taccctagga gagctagaca ataaaaccat 1260
aatatcagaa aagaaaacct caaaactgag agttgtcact tccgaaccac tagtaaaaca 1320
cctgcaaaat aaagagaaat taattaatac ataataaata tttaataaaa aaatgaaatt 1380
tcccttataa ataaaataaa ataaaatatg aaattttata taaatagtca catagaattc 1440
tctgacgtag atacttatat gaaattttat atgaaatttt atatgtagta tgagttactt 1500
ccaaatgttc tcttaataaa tttaaaacag agtctgtact gacaaaactg taagaaaatt 1560
atagttttac aaacattagg tacttataac gctaaaaata aaattttggg tatttatgct 1620
actatttacc aaaaaaaata ataataaaaa aagtttatat tttctctaaa aatatagaat 1680 gggggggagtg taagaaacat aaacctaaca aataggctga aatggaaaag aagaaggccc 1740
atattgagat atgagaatgg gggctatact taatttaagc taaatatagg atctgtctgc 1800
aaaataagta ctataaaaac atatctaggg ttttagtcgt aacccttcag tctggtgtgc 1860
tagttcagct ctaccttcgc cgcacgagaa gctcaggttt ccttcccttt tctctcttct 1920
ctgtctctgc ttcgtatgtg tttttctcta agataacgaa aatggaaatg aacttctttc 1980
tgttcattct cctacatttt gtgatgatac acactgtgtt ttagcaacat ttcttgtact 2040
ctcgttagtt tgtgttagtt catattagat ctggattcat gggttttcat tagattgttt 2100
tatatgtttg aggataagaa aataatgggt tttgattctt ttgttgcatt tctgttttag 2160
cacttaaaat ttagagcttt tttgtttaac ttttaatttg attatattct tatgaaacta 2220
tatttgttat tgccagtagg aagaagaga 2249

<210> SEQ ID NO 35
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 35
ccgtgaaaac ttaacacagt acac 24

<210> SEQ ID NO 36
<211> LENGTH: 31
<212> TYPE: DNA
<213> ORGANISM: Artificial sequence
<220> FEATURE:
<223> OTHER INFORMATION: Single strand DNA oligonucleotide

<400> SEQUENCE: 36
ctaaaaatac agaattaaaa caaaatctat c 31

<210> SEQ ID NO 37
<211> LENGTH: 4071
<212> TYPE: DNA
<213> ORGANISM: Cannabis sativa

<400> SEQUENCE: 37
actttgtttt taattttgca gtttcttttg gatgattaaa tgttctctag aatctcagac 60

-continued

```
tcttgtattg cttgctcaaa taccttaaaa gtaatatttt ctttttttgcc attttcaata    120
tgatttttga agcaaggatt gttttgatga tattaaacgc ccaatatgat agagggttct    180
gaaattttaa aatacttttc agctaaaatt caccaagtaa aattcttaca tcaaacaccc    240
gacccaagag tctttttaac cataaattac cttatttcaa gtctgttatc ttagtacact    300
gtaattttcg tttagtgttg tttgttttgt gtcgtgttca cagatttgag atgttttttt    360
gtagcaaata actatacgtt taaagcacat tgcatcatca actcatataa actaaagaaa    420
atcaacacta ataattcatc tctagtaatg atattaatca ttatatatat attctatgtt    480
gtgtctggtg tgattgtctt aatttccaag ttctaacttg ttatttccaa gttcaagact    540
taatatatca tcttatttgc aaataatgac tcgtattgct aacaggaaat agatgtgttt    600
agagaatttc tattatatat aaaaacaaaa aaaatctaca aagtatacac gtacaatcaa    660
tcgtctaaga agttgaacat agttgcaaaa acgttacaga actcataaat ctcttaacag    720
gctattattg actaaataaa atggtaacaa tgagaataac caaatttctt tgggcaatat    780
ttagatagtt tcctttcaaa aagataaaaa aacacacaaa agaggacctc gttgttccta    840
accagctaat caatctggaa aagcctccaa aacgcacccc ttggcttgga tactcatgca    900
ggaaaggaat acctaaagga agctcatctc atatatgaga atccaccata atcggaagct    960
ctcactcaat ggtaagctaa agggaaggct ctccacttac cccaaaggag aaaattacac   1020
tctatacctt ttttatattg tcctttttta tttttaccat ctttttttaaa atctatcatt   1080
tttacctctt ttttaaatat tgtaccaatt ttgcccttgt cacttcaaga tactctccat   1140
gtgactctct tatatcaggg tattttgggt acaatacata taaaaagagg tatgtttcaa   1200
ataaatataa aattagaggc aaatttgatt aattgattaa taaaatgggt atttttcaac   1260
ttacccctta ttaaagagcc tctgagctac gtgcctagaa aatggagccc atcaattgga   1320
gaaacaaata agagcatctc cactaatgat ttatatttaa gaaatgctta ctagattatt   1380
tatttagcaa aatataagga tgctatgtta ttggagataa attagtacta tcatagaaaa   1440
ttatgttgat gccattaaag gtaaaatagt gtgacaatat ttataattaa aataaataat   1500
atattaaata ataatgtgag agattataat tatagcattc ttgaaaggtg ttatattatt   1560
acagtatttt taaaagttta tatttttgga taaatattat cagattgaca ataaaaaaaa   1620
taatccataa aaatcaatat tatgactttt gggtatttac gaagtaattt aaaaaaaagg   1680
atattcattg atcaaaaata cttttatatt atatattttt ttgagtgggt tgtctaatat   1740
acttttaatc tctacttaag cctagcttat aatttacaat aacttaagga gtttaatgat   1800
gacattatct ataaaagtag gtacatttta aaaaatatga aaatagaagt aaaaattaaa   1860
acaaataaat taaaatgggt gcaatgtaat tttctaaaaa aaaaaataaa aggccaattt   1920
tatattttta taaaaagaat atgggctttc agcaaaatga gcgcaaaaat agaggactag   1980
gcaggcccgt gtaaagccca ataagaaata tatatattat aagaaacaga agcgagttgc   2040
gcctctcaga ctgaaaccct agctaagctc tactctctcc tctcttctgc aaccatggcc   2100
gtcgggtacc tcttctctat ttctttcctc cgctatatgc ttcattcatg tacttctgaa   2160
tcatggattt ctgtatgttt atttctttct tttctatttt cataacatgc atgtgatctg   2220
atttttttagg aagaacaaga ggatttccaa gggtaagaag ggaggcaaga agaaggcgta   2280
agtcaatttt caacttttat cttttattca gatttgattt gagaatcaaa atctctataa   2340
ttgcattaac actttgttaa taatataata cagagccgat ccctttgcca agaaggattg   2400
gtatgacatc aaggctcctt ctctattcaa ccaaagacaa gttggcaaaa cccttgtcac   2460
```

```
tagaactcag ggaaccaagg tttgtctcct caaaatgctt tcttttatca ttataattat   2520
taagcttagg tgctcatgat gatttattgt ttgttagtta agagcctaat aagggattat   2580
tattcctttt ttttgaatgt caagctctat ttggggaaat gtggttgata atttaaactt   2640
ataatgatga tgatgattaa gcattaggac tatacttttc tctagtattt tttttttcat   2700
cagtagcaat tgttagttta gttgaactta tatgtaagtg tatattttgg attggagatg   2760
agctgttatg ttgtttcatt aatatgccca attgtgtgtg aggatatact tcatgttttc   2820
tttgtatatt tcatgtattt agaggcgcat tgatgtttaa tttgttatta tgttatcaga   2880
ttgcttctga aggtctaaaa cacagagtgt ttgaggtttc cttggctgat ctccagaagg   2940
atgaggatca tgcttacagg aaaatccgtt tgagagctga agatgttcaa gggaagaatg   3000
ttctaactaa cttctgggta ggtttctttt ttaatgaatt tcattcatct atttggaact   3060
tctttttgta caatgtttta cttatttaat ttttataatg cgaatttgca gggaatggac   3120
ttcaccaccg ataagttgag gtcacttgtt cgcaagtggc aaacacttat tgaggctcat   3180
gtagatgtca agaccactga caactacacc ctcaggatgt tctgcattgc tttcacaaag   3240
agacgtgcta accaggtcaa gagaacctgc tacgcgcaat ccagccagat tcgtcaggtt   3300
cgatttgatt tgattgtctc tttctcttaa atgctccaca ttttcattta gtatgctatg   3360
ctttgatgac atatagaaac ttgtgttaac aatctttgtt tgcttatgtt ttaatttcct   3420
ttttcataga ttaggagaaa gatgagagaa attatgatca accaggccac gtcctgtgat   3480
cttaaggatt tggtgaacaa gtttattccc gaaatgattg gtagagagat tgagaaggca   3540
acatcaagca tctacccact ccagaatgtc ttcatccgca aagtgaagat ccttaaagct   3600
cccaaattcg atcttgggaa gttgatggag gtattcattg gcattggatt ccattcttaa   3660
cacccctttt aactcgtagg aaccttagat tgttttttg atttttgtcg aattgtttgt   3720
gtaggttcac ggtgattact ccgaggatgt tggagtgaag gttgacaggc cagctgatga   3780
aacagcggtc gagggtgagg tgaccgaggt tgtgggagca taatgaaact caaattttct   3840
ttttcatttt gttaaaatca gtaacattta aggtcttttc aattttgcgg atttgtgttt   3900
gacagagtag aatttgtatg gatggaattt tgctctaatt agacttatgg cagaagaaca   3960
acaaacaaat actgcttaga aaattttatc agacatgtca tgtattatct ttgcttcttt   4020
ttttatcatc ttatttatag attccttaca tgtttgattg atttcttcga a            4071
```

<210> SEQ ID NO 38
<211> LENGTH: 2094
<212> TYPE: DNA
<213> ORGANISM: Cannabis sativa

<400> SEQUENCE: 38

```
actttgtttt taattttgca gtttcttttg gatgattaaa tgttctctag aatctcagac     60
tcttgtattg cttgctcaaa taccttaaaa gtaatatttt cttttttgcc attttcaata    120
tgatttttga agcaaggatt gttttgatga tattaaacgc ccaatatgat agagggttct    180
gaaattttaa aatacttttc agctaaaatt caccaagtaa aattcttaca tcaaacaccc    240
gacccaagag tctttttaac cataaattac cttatttcaa gtctgttatc ttagtacact    300
gtaattttcg tttagtgttg tttgttttgt gtcgtgttca cagatttgag atgttttttt    360
gtagcaaata actatacgtt taaagcacat tgcatcatca actcatataa actaaagaaa    420
atcaacacta ataattcatc tctagtaatg atattaatca ttatatatat attctatgtt    480
```

```
gtgtctggtg tgattgtctt aatttccaag ttctaacttg ttatttccaa gttcaagact    540

taatatatca tcttatttgc aaataatgac tcgtattgct aacaggaaat agatgtgttt    600

agagaatttc tattatatat aaaaacaaaa aaaatctaca aagtatacac gtacaatcaa    660

tcgtctaaga agttgaacat agttgcaaaa acgttacaga actcataaat ctcttaacag    720

gctattattg actaaataaa atggtaacaa tgagaataac caaatttctt tgggcaatat    780

ttagatagtt tcctttcaaa aagataaaaa aacacacaaa agaggacctc gttgttccta    840

accagctaat caatctggaa aagcctccaa aacgcacccc ttggcttgga tactcatgca    900

ggaaaggaat acctaaagga agctcatctc atatatgaga atccaccata atcggaagct    960

ctcactcaat ggtaagctaa agggaaggct ctccacttac cccaaaggag aaaattacac   1020

tctatacctt ttttatattg tcctttttta tttttaccat ctttttttaaa atctatcatt   1080

tttacctctt ttttaaatat tgtaccaatt ttgcccttgt cacttcaaga tactctccat   1140

gtgactctct tatatcaggg tattttgggt acaatacata taaaaagagg tatgtttcaa   1200

ataaatataa aattagaggc aaatttgatt aattgattaa taaaatgggt atttttcaac   1260

ttacccctta ttaaagagcc tctgagctac gtgcctagaa aatggagccc atcaattgga   1320

gaaacaaata agagcatctc cactaatgat ttatatttaa gaaatgctta ctagattatt   1380

tatttagcaa aatataagga tgctatgtta ttggagataa attagtacta tcatagaaaa   1440

ttatgttgat gccattaaag gtaaaatagt gtgacaatat ttataattaa aataaataat   1500

atattaaata ataatgtgag agattataat tatagcattc ttgaaaggtg ttatattatt   1560

acagtatttt taaaagttta tatttttgga taaatattat cagattgaca ataaaaaaaa   1620

taatccataa aaatcaatat tatgactttt gggtatttac gaagtaattt aaaaaaaagg   1680

atattcattg atcaaaaata cttttatatt atatattttt ttgagtgggt tgtctaatat   1740

acttttaatc tctacttaag cctagcttat aatttacaat aacttaagga gtttaatgat   1800

gacattatct ataaaagtag gtacatttta aaaaatatga aaatagaagt aaaaattaaa   1860

acaaataaat taaaatgggt gcaatgtaat tttctaaaaa aaaaaataaa aggccaattt   1920

tatattttta taaaaagaat atgggctttc agcaaaatga gcgcaaaaat agaggactag   1980

gcaggcccgt gtaaagccca ataagaaata tatatattat aagaaacaga agcgagttgc   2040

gcctctcaga ctgaaaccct agctaagctc tactctctcc tctcttctgc aacc         2094
```

<210> SEQ ID NO 39
<211> LENGTH: 3179
<212> TYPE: DNA
<213> ORGANISM: Cannabis sativa

<400> SEQUENCE: 39

```
tatgttagca attagtgata cggtttatgg ataataatca atattataat gccgcagtag     60

ttttttttatt gattaaagtc tactctattt aataagttca aaaggaaatg catgcatcat    120

ttcttggtac ctattacatg aatctagctc ataaatgtaa tatacaaaat atagtaattt    180

atgatgtata aattaaacta catagccaat caagaagttt tggtattgca tggtagctat    240

ttatgaggaa gaaacttaat tatattttct tcttttctag ataaggcaaa aaggtaggct    300

tctttaatct tagatgagtc tcaatgtaac gtttgttctt ttatagcttc aactgtccaa    360

atatgggcaa acccttccta aaaatgtata catatttttta ttaattacaa tatatatata    420

tttgtaatta cagctaatat atatttacta tcgaagtgtt atatatcttt gaactattat    480

ctttgattta atagttatgc taacttacac ctagaggtga gaagttcaaa tattccaaca    540
```

```
agaacatttt tatttcttaa ttataaaagt ttacttttca aaaaatgtag ctttagaatt    600
taaacccccta tatttaatac attaactatt gaagaatttt ctttaaagaa aagttacaca    660
aagtacttaa gattgtactt gttttttttt tttttttaa tgtttttaag gatttttttc    720
cttttttttt tttttacat ttttacatac tgtattttc aaagagaaaa caaaatatgt    780
tgttgttatg ctgtgcaacg ttatattata ttctcttaat gtgaaaataa tattttttt    840
tagaacaacc taaaaataac aatttataaa aaaaaaaagt ttgtaaaaaa taatattctc    900
ttataatgta atttttttt tattatttat ggagtattat caagtaattt catattttta    960
tggttacttt tcattttact ttgtattata tttactacta taaaaaaaaa atacaagtat   1020
atataaatat cacgtagaaa aaaaattatg ttctctgtct tacaaaaaaa gatatttttt   1080
tttttgaac tttaaattct aaatccgcat ttcaacattt attagagttg gttatatttt   1140
gaaatgaaca tgacatttct cgtatatctg tatgtatgta tacaatgaag aaagtcacac   1200
ttccaaagta tggctgtttg acaatggtag ataaataata acatctaaac taattaatgc   1260
ttctttaatg acctgaacaa tcctaattat acttaaatct caattagaga attactcaag   1320
attatttaaa ttacaaatta gaacacacag ctgatgaaca tctcataata atcttacgtg   1380
taattccttt taaagaataa aaaatacatc tacatcatat tcatatgcaa gttgaaggga   1440
gaaaattaca ggtcaagcta tacaaacaaa taatacccttt cgccacataa tacataactt   1500
agtatgtatt tatccccaaa accaaactag aggttagata ttatttattg aaatcatgaa   1560
aagagaaaat aatagtactt gtttaaaggc tgatgacaaa agagttagct aaatattttt   1620
ttgtcatttt ccttctcgtt ggctgtcatg tttgtcataa tatctcttct tagctggctc   1680
tagtctttag tctgtagatg aagtcattag tagatttggt ggaaacttaa aagtggtatt   1740
attatatgta atagctgtgc ctaaagattt taatcttcta tcaacgcgct ttcttgctgg   1800
catttcactc tctcctctta gctacttatt catttctttt tctttcttta tcaatacgtt   1860
atattaatta gctttccact actgatgaat tagctaaacc taagctcctt ccgagtagtt   1920
gctttagtta gcccactaat caccaaatta acatactcac attatgtata taaatacacc   1980
attttccctt gtcttctaaa ctcacacaaa acaaagcata atttaagagt ctcttctttt   2040
ctctaagctc agtataatta aaaatggcat ctttcgcctc agaaactctc actttcatct   2100
tcttcatctc tctactccat ttgggttcat cggggaggat tctttccgac gagtctgacc   2160
aaacccaaca gcctcttccc tttcaatacc ataatggccc tcttctgttt ggaaaaatct   2220
ccattaactt aatatggtac ggaaacttca aaccaatcca acgagccatt gtctccgact   2280
tcattacctc cctcacttca tcttctaaaa ccaacacaga ccaaccatca gtcaacacgt   2340
ggtggaagac catcgaaagc taccaatacc accacaagat gagcaactcc gtctcgttag   2400
gatcccagtt catcgacgag aactactccc tggggaaatc gttgaccagt caacaaatag   2460
tgggactctc cagcaagggc ggccaaaagg acgccatcaa cgttgttctg actgcggctg   2520
atgtggcggt ggaagggttc tgctctagta agtgtggaac acacggtgtg tcatctgggt   2580
cgggacccgg tagtaagagg tccaagttcg gttacatatg ggtgggaaac tcggagagtc   2640
agtgcccagg tcaatgcgca tggcctttcc accagccaat ttacggacca caaacacagc   2700
cactgattgc cccaaacaac gacgtgggtt tggacggaat gatcatcaac gtggctagcc   2760
ttttggctgg aaccgtaacg aacccgttcg gaaatgggta cttccaaggg ccgaaggagg   2820
ctccacttga ggcggcttcg gcttgtagcg gtacttttgg gaagggggcg tatcctggat   2880
```

```
accctggtca actcttggtt gaccccacca ctggtgcaag ctacaatgct cacggtgaca   2940

atggcaggaa atacttgctt cctgctctgt ttgacccttc cacctccact tgttctacct   3000

tggtttgaac atacataatt aaattacaca ctgtataaat atatatctag agagagagca   3060

ttgatttttt ttttttaatt ctttttatta ttattcgact attcatcatg tatacttgtt   3120

ataccaccat tataataaac tattggtatt attctttata tatacgattt tttaatcaa    3179


<210> SEQ ID NO 40
<211> LENGTH: 2063
<212> TYPE: DNA
<213> ORGANISM: Cannabis sativa

<400> SEQUENCE: 40

tatgttagca attagtgata cggtttatgg ataataatca atattataat gccgcagtag     60

ttttttttatt gattaaagtc tactctattt aataagttca aaaggaaatg catgcatcat    120

ttcttggtac ctattacatg aatctagctc ataaatgtaa tatacaaaat atagtaattt    180

atgatgtata aattaaacta catagccaat caagaagttt tggtattgca tggtagctat    240

ttatgaggaa gaaacttaat tatattttct tcttttctag ataaggcaaa aaggtaggct    300

tctttaatct tagatgagtc tcaatgtaac gtttgttctt ttatagcttc aactgtccaa    360

atatgggcaa acccttccta aaaatgtata catattttta ttaattacaa tatatatata    420

tttgtaatta cagctaatat atatttacta tcgaagtgtt atatatcttt gaactattat    480

ctttgattta atagttatgc taacttacac ctagaggtga gaagttcaaa tattccaaca    540

agaacatttt tatttcttaa ttataaaagt ttacttttca aaaaatgtag ctttagaatt    600

taaaccccta tatttaatac attaactatt gaagaatttt ctttaaagaa aagttacaca    660

aagtacttaa gattgtactt gttttttttt ttttttttaa tgtttttaag gatttttttc    720

cttttttttt ttttttacat ttttacatac tgtatttttc aaagagaaaa caaaatatgt    780

tgttgttatg ctgtgcaacg ttatattata ttctcttaat gtgaaaataa tatttttttt    840

tagaacaacc taaaaataac aatttataaa aaaaaaaagt ttgtaaaaaa taatattctc    900

ttataatgta attttttttt tattatttat ggagtattat caagtaattt catattttta    960

tggttacttt tcattttact ttgtattata tttactacta taaaaaaaaa atacaagtat   1020

atataaatat cacgtagaaa aaaaattatg ttctctgtct tacaaaaaaa gatatttttt   1080

ttttttgaac tttaaattct aaatccgcat ttcaacattt attagagttg gttatatttt   1140

gaaatgaaca tgacatttct cgtatatctg tatgtatgta tacaatgaag aaagtcacac   1200

ttccaaagta tggctgtttg acaatggtag ataaataata acatctaaac taattaatgc   1260

ttctttaatg acctgaacaa tcctaattat acttaaatct caattagaga attactcaag   1320

attatttaaa ttacaaatta gaacacacag ctgatgaaca tctcataata atcttacgtg   1380

taattccttt taaagaataa aaaatacatc tacatcatat tcatatgcaa gttgaaggga   1440

gaaaattaca ggtcaagcta tacaaacaaa taataccctt cgccacataa tacataactt   1500

agtatgtatt tatccccaaa accaaactag aggttagata ttatttattg aaatcatgaa   1560

aagagaaaat aatagtactt gtttaaaggc tgatgacaaa agagttagct aaatattttt   1620

ttgtcatttt ccttctcgtt ggctgtcatg tttgtcataa tatctcttct tagctggctc   1680

tagtctttag tctgtagatg aagtcattag tagatttggt ggaaacttaa aagtggtatt   1740

attatatgta atagctgtgc ctaaagattt taatcttcta tcaacgcgct ttcttgctgg   1800

catttcactc tctcctctta gctacttatt catttctttt tctttcttta tcaatacgtt   1860
```

atattaatta gctttccact actgatgaat tagctaaacc taagctcctt ccgagtagtt 1920
gctttagtta gcccactaat caccaaatta acatactcac attatgtata taaatacacc 1980
attttccctt gtcttctaaa ctcacacaaa acaaagcata atttaagagt ctcttctttt 2040
ctctaagctc agtataatta aaa 2063

<210> SEQ ID NO 41
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 41
ggtgactgat tccctcaatt tccc 24

<210> SEQ ID NO 42
<211> LENGTH: 28
<212> TYPE: DNA
<213> ORGANISM: Artificial sequence
<220> FEATURE:
<223> OTHER INFORMATION: Single strand DNA oligonucleotide

<400> SEQUENCE: 42
taaagaagct cccataccca tcttttgc 28

<210> SEQ ID NO 43
<211> LENGTH: 4220
<212> TYPE: DNA
<213> ORGANISM: Cannabis sativa
<220> FEATURE:
<221> NAME/KEY: misc_feature
<222> LOCATION: (563)..(883)
<223> OTHER INFORMATION: n is a, c, g, or t
<220> FEATURE:
<221> NAME/KEY: misc_feature
<222> LOCATION: (2013)..(2247)
<223> OTHER INFORMATION: n is a, c, g, or t
<220> FEATURE:
<221> NAME/KEY: misc_feature
<222> LOCATION: (3586)..(3695)
<223> OTHER INFORMATION: n is a, c, g, or t

<400> SEQUENCE: 43
cgatttgtta ccttgtttgg taacggagtt tgatggttaa taaaatttaa ttttccatta 60
aaataaaaat aaaaatacat gaaccaattg aaagttacat tttttacatt aaagttttat 120
ttgtctaatt ttttaaaaac gtattttgtg tcaatcacaa ttttaatgtt gagactcaca 180
aattggttaa cttttaatta catgcaataa agtactacac cttttgctta tcatttgtta 240
tagttttaat tttttttgtt aattaaatgt taccaatacc caaaaaaatc gttcttaaaa 300
gagagagagt tatatattgg gaaatttaca taaaataata ttttcggtaa atattttaca 360
tttttaagtt gaaatatata ttccaatatt tttacgatgt tctataaaaa caacaagaaa 420
ataataaaaa ataaccacat gaacgtaaca ggaaaacaac ataaaaataa tatataaata 480
acaaaaatcc aacaaaaaaa ataacaagag tataatataa aaataatatt aaagtattaa 540
aagactggct gcaccttcca gtnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780

```
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnaaaaaaa aaaaaaaaaa    900
aaaaaattac aacaatgttt aaaattaagg tttttaccat attgaaattt tcaattttct    960
tttacttttt tttttactgt ggagcagaat ttttttaaaa aatactgtgc aagttttata   1020
ttgtgtaatg tgtaaagttt ttaatgttgt ttcacggtta ttttttagtt gttctactat   1080
tgttttaatt gttctgtttt gttgttttac ggttgcttta taaaaagaca gtatttttgt   1140
aaaagattcc atgtaccagt aaaattgtaa acttttgtct aaaatctaat atttttgtaa   1200
aaatcccttt aatattcctt attttcgtgt atttctaaaa taattcctta tatattggat   1260
tatttacacc acatactgaa aatttttttt ttttttatct ttttgccatg gtgcagaatt   1320
ttttcaaaaa tacagtgtaa gttttatact atgtactatg ttaaattttt actgttgttc   1380
tactattgtt ttttagtttt ccactattat ttttagttgt tttattatct gtttcactgt   1440
agttatataa aaacatagta tttttgaaaa aaaaattagt gtgataatat ttttgtaaaa   1500
attaacctaa attctattat ttttataaat ttccttatat atttggagaa aattacaatc   1560
tatatcattt ttatattgtc ctcttttatt tttaccatct tttttaaagt ctatcaattt   1620
tacctctttt tttaaacatt gtaccaattt tgcccctatc acttcaagat actttccatg   1680
tgactctctt atgtcagagt attttgagta caatacatat aaaaagaagt atgtttcaat   1740
taaatataaa attaagttaa tttgattaat tgattattaa aaatgataat tttcaactta   1800
ccccatatat ttgagtgaag aaccaacaat tgggcttttt cccaattaat ccaaaccaag   1860
aataacctta tcaacccaac caaccaaaca accaccttag ggttcgttca ttcagatatc   1920
cccaaaaaaa accctaatca aaacgatttt ctctcttcaa atccccacat ataaaaatcc   1980
catttttaac acttctcatt ttcattctgg ttnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnnnnnnnn nnnnnnnnnn   2220
nnnnnnnnnn nnnnnnnnnn nnnnnnntaa aatatacatc aaaccaacaa accctagaaa   2280
cacagagaga gagagagctt cagcagccga aaccctagac ccttcttctc aatccaacca   2340
tggcagctga aggactagtt ctccgtggca tcatgaggtc tcacaccgac atggtaacag   2400
ccatagcttg cccaattgac aactcggaca tcatcgtcac tgcttcccgt gacaaatccc   2460
taatcctatg gaaactcacc aaggacgaca agacctacgg tgttccccac cgcaggctaa   2520
ccggccactc tcacttcgtc caagacgtcg ttctctcatc agatggtcag ttcgctcttt   2580
ctggatcttg ggatggtgag cttcgtttgt gggatctagc cgccggagtc tcggcaagga   2640
gattcgttgg tcacacaaaa gatgttcttt ctgtggcttt ctcgattgac aatcgtcaga   2700
tcgtttctgc ttctcgtgac cgtacgatca agctttggaa cacactcggt gagtgtaagt   2760
atactattac tgatggtgaa gctcataatg attgggttag ttgtgttagg tttagcccta   2820
ataatcttca gccaactatt gtttctgctt catgggatcg tactgttaag gtttggaatc   2880
tttccaactg taaactgagg tgtactcttg ctggacatgg tgggtatgtt aacactgttg   2940
ctgtttcacc tgatggttca ctctgtgcca gtggtggtaa agatggtgtt atcttgcttt   3000
gggatttggc tgagggaaag agattgtatt ctcttgatgc tggttctatt attcatgctc   3060
tttgctttag ccctaacagg tactggcttt gtgctgctac tgagaacagt attaagatct   3120
gggatttgga gagtaagagt attgttgagg atttgaaggt tgatcttaag gctgaggccg   3180
```

agaagactga tgatacccat gttgcaactg ccaacaagaa gaaggtataa ttctaatgtc 3240
atttttgttt tgattttgct taattttgtt ggttttgagt aatctgaatt gtgtgtataa 3300
atattggtta tttgagtttg aacattgatt gttagatgaa aatggtttta tgattcattt 3360
gtgtataaag ataaaggtaa tgctaactct ttagatgatg tttcaggctt aagaacataa 3420
cttttgtatt ggggttttaa ggacattatt gtgtttaagg tttaatctca gagttaactc 3480
tttagacgac ttttcaggtt tatgaacata tttatgagat atagtcttgt accgaaaagt 3540
tagcattttt tcctgttgtt tattgtacta ttgtttttta gttttnnnnn nnnnnnnnnn 3600
nnnnnnnnnn nnnnnnnnnn nnnnnnnnnn nnnnnnnnnn nnnnnnnnnn nnnnnnnnnn 3660
nnnnnnnnnn nnnnnnnnnn nnnnnnnnnn nnnnntatgg ttgatcttga atgaattaca 3720
ggttatatac tgcacaagct tgagctggag tgctgatgga agcactttgt ttagtggata 3780
caccgatgga gtaattagag tttggggaat tggtcgttat tagaaggaaa aagcttctat 3840
cagtaatatt attctcccta atgcacttct tctactgttt tcttagtttt tgagaacaaa 3900
aaaccgtatt tactatcttc ttaaattcta gtgttttcgg aaaaaaggta tttaggtttt 3960
tgttggagat gttgaatttt tggaattctc ttaagttgat gacttgtggc tttgaggccc 4020
catttgtttt ttggtttttg ttttctttta tatatttcat tagataatca tgttggtctc 4080
tctatacttt tctctatttg aaatcccaat ttgatggtgg aattcgatgg tggtgtgtgc 4140
atgtgcaatg tttcatgaat tgtataggct caattccctt caaattgaat gatgaaatat 4200
ttttaaagtt gaagagtgaa 4220

<210> SEQ ID NO 44
<211> LENGTH: 2339
<212> TYPE: DNA
<213> ORGANISM: Cannabis sativa
<220> FEATURE:
<221> NAME/KEY: misc_feature
<222> LOCATION: (563)..(883)
<223> OTHER INFORMATION: n is a, c, g, or t
<220> FEATURE:
<221> NAME/KEY: misc_feature
<222> LOCATION: (2013)..(2247)
<223> OTHER INFORMATION: n is a, c, g, or t

<400> SEQUENCE: 44
cgatttgtta ccttgtttgg taacggagtt tgatggttaa taaaatttaa ttttccatta 60
aaataaaaat aaaaatacat gaaccaattg aaagttacat tttttacatt aaagttttat 120
ttgtctaatt ttttaaaaac gtattttgtg tcaatcacaa ttttaatgtt gagactcaca 180
aattggttaa cttttaatta catgcaataa agtactacac cttttgctta tcatttgtta 240
tagttttaat tttttttgtt aattaaatgt taccaatacc caaaaaaatc gttcttaaaa 300
gagagagagt tatatattgg gaaatttaca taaaataata ttttcggtaa atattttaca 360
tttttaagtt gaaatatata ttccaatatt tttacgatgt tctataaaaa caacaagaaa 420
ataataaaaa ataaccacat gaacgtaaca ggaaaacaac ataaaaataa tatataaata 480
acaaaaatcc aacaaaaaaa ataacaagag tataatataa aaataatatt aaagtattaa 540
aagactggct gcaccttcca gtnnnnnnnn nnnnnnnnnn nnnnnnnnnn nnnnnnnnnn 600
nnnnnnnnnn nnnnnnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnnnnnnn 720
nnnnnnnnnn nnnnnnnnnn nnnnnnnnnn nnnnnnnnnn nnnnnnnnnn nnnnnnnnnn 780

```
nnnnnnnnnn nnnnnnnnnn nnnnnnnnnn nnnnnnnnnn nnnnnnnnnn nnnnnnnnnn    840

nnnnnnnnnn nnnnnnnnnn nnnnnnnnnn nnnnnnnnnn nnnaaaaaaa aaaaaaaaaa    900

aaaaaattac aacaatgttt aaaattaagg tttttaccat attgaaattt tcaattttct    960

tttacttttt tttttactgt ggagcagaat ttttttaaaa aatactgtgc aagttttata   1020

ttgtgtaatg tgtaaagttt ttaatgttgt ttcacggtta ttttttagtt gttctactat   1080

tgttttaatt gttctgtttt gttgttttac ggttgcttta taaaaagaca gtatttttgt   1140

aaaagattcc atgtaccagt aaaattgtaa acttttgtct aaaatctaat atttttgtaa   1200

aaatcccttt aatattcctt attttcgtgt atttctaaaa taattcctta tatattggat   1260

tatttacacc acatactgaa aatttttttt ttttttatct ttttgccatg gtgcagaatt   1320

ttttcaaaaa tacagtgtaa gttttatact atgtactatg ttaaattttt actgttgttc   1380

tactattgtt ttttagtttt ccactattat ttttagttgt tttattatct gtttcactgt   1440

agttatataa aaacatagta tttttgaaaa aaaaattagt gtgataatat ttttgtaaaa   1500

attaacctaa attctattat ttttataaat ttccttatat atttggagaa aattacaatc   1560

tatatcattt ttatattgtc ctcttttatt tttaccatct tttttaaagt ctatcaattt   1620

tacctctttt tttaaacatt gtaccaattt tgcccctatc acttcaagat actttccatg   1680

tgactctctt atgtcagagt attttgagta caatacatat aaaaagaagt atgtttcaat   1740

taaatataaa attaagttaa tttgattaat tgattattaa aaatgataat tttcaactta   1800

ccccatatat ttgagtgaag aaccaacaat tgggcttttt cccaattaat ccaaaccaag   1860

aataacctta tcaacccaac caaccaaaca accaccttag ggttcgttca ttcagatatc   1920

cccaaaaaaa accctaatca aaacgatttt ctctcttcaa atccccacat ataaaaatcc   1980

catttttaac acttctcatt ttcattctgg ttnnnnnnnn nnnnnnnnnn nnnnnnnnnn   2040

nnnnnnnnnn nnnnnnnnnn nnnnnnnnnn nnnnnnnnnn nnnnnnnnnn nnnnnnnnnn   2100

nnnnnnnnnn nnnnnnnnnn nnnnnnnnnn nnnnnnnnnn nnnnnnnnnn nnnnnnnnnn   2160

nnnnnnnnnn nnnnnnnnnn nnnnnnnnnn nnnnnnnnnn nnnnnnnnnn nnnnnnnnnn   2220

nnnnnnnnnn nnnnnnnnnn nnnnnnntaa aatatacatc aaaccaacaa accctagaaa   2280

cacagagaga gagagagctt cagcagccga aaccctagac ccttcttctc aatccaacc    2339
```

<210> SEQ ID NO 45
<211> LENGTH: 2292
<212> TYPE: DNA
<213> ORGANISM: Cannabis sativa

<400> SEQUENCE: 45

```
gtttgggttt ggggttgggg taggaatttt ttgtgatgtt gtgtttgggt gtggcatacc     60

atttggatct aaggtttttg gttacttaga ctaaaatagc aagggaggaa atatggaaag    120

gaagaagctt tggtggtctt cattttgcct ttggttgatt ttggtagttc atcctttatg    180

ggtgattatg gtatctgcta atatggaagg tgatgccttg catagtctga ggtccaattt    240

acaggatccc aacaatgttc tgcagagttg ggatcccacc cttgtaaacc cgtgtacatg    300

gtttcatgtc acttgcaaca atgataatag tgtgataagg gttgatcttg gaaatgcagc    360

tttgtctggt caacttgttc cacagcttgg ccttctcaag aatttacaat atttggaact    420

ttacagtaat aacattagtg gaacaattcc tagtgatttg gggaatttga ccagcttggt    480

tagcttggat ctgtatttga atagttttac tggtcctatc ccggacacct tgggcaagtt    540

gtcaaaatta agatttcttc ggcttaacaa caatagtctg acgggtccaa ttcctatgtc    600
```

gttgaccaac atcacctcac tgcaagtgct ggatctgtca aataacaaat taaccggaga 660
ggttccagac aatggctcgt tttctttatt cactcccatc agttttgcta ataacttaaa 720
tctatgtggc ccggttactg gacgaccctg cccaggatcc cccccatttt cacctcctcc 780
tccttttgtc ccaccacccc caatttcagt cccaggtgga aatagtgcga ctggggctat 840
tgctggtgga gttgctgctg gtgctgcttt attatttgct gctcctgcta ttgcatttgc 900
ttggtggcgt cgaaggaagc cacaagaatt tttctttgat gtacccgctg aggaggatcc 960
tgaagttcat cttgggcagc ttaaaaggtt ttcgttgcga gaattacaag tggcaactga 1020
tagttttagc aacaaaaaca ttctgggacg ggtggattt ggtaaggtct acaaaggtcg 1080
ccttgcagat ggttctttgg ttgctgtaaa gagactgaaa gaagagcgta cacctggtgg 1140
cgagttgcag tttcaaacag aagtagagat gatcagtatg gctgtgcatc ggaatcttct 1200
tcgattacgt gggttctgta tgacaccaac tgaacgatta cttgtttatc cttatatggc 1260
taatgggagt gttgcctcat gcttaagaga acggccgcca caccaactgc ctcttgattg 1320
gcctactagg aaacgaatag cattgggttc tgcaaggggt ctttcgtatt tgcatgatca 1380
ttgcgatcca aaaattattc atcgtgatgt gaaagctgct aatattttgt tggatgagga 1440
gtttgaagca gttgttggag atttcggttt ggctaaactt atggactaca aggacactca 1500
tgttactaca gctgtacgag gcacaatcgg gcatattgct ccagagtacc tctctaccgg 1560
gaagtcttct gagaaaaccg atgtgtttgg ctatggaatc atgcttttgg aattaattac 1620
tggacagaga gcttttgatc ttgctcggct tgcaaatgat gatgatgtca tgttgctcga 1680
ctgggtgaaa ggactactga aagagaagaa gttggaaatg ctggtggacc ccgatcttca 1740
aaagaactac atagaatccg aagtagagca gcttattcag gttgcactgc tctgcacaca 1800
aggttctccc atggaccgac caaagatgtc agaggtggtg agaatgctcg aaggcgatgg 1860
cttggccgag agatgggatg aatggcaaaa agtggaagta ctacgacaag aagtcgaact 1920
agcccctcat ccaaactcag actggatagt agactcaacc gaaaacttgc atgcggtcga 1980
gttatctggt ccgaggtaac cctggcacaa tagaaagtgg aagaaaaagg gaatttactt 2040
acaacttaat ttttttaat taattataat agcttttttt tcttcttctt aatgaccata 2100
atctgattaa tgtctctttg taagtccatt ctgcattgta ttcgttacat ttgtgcatat 2160
gagagtcgca ttggtaaggt gcaaatttgt attgtctgct gcagtgtgac aaaagccata 2220
gatgttttta taatatatga agctgtggca gtttttatct tttgttcact gcagcagaca 2280
atacaaattt gc 2292

<210> SEQ ID NO 46
<211> LENGTH: 598
<212> TYPE: PRT
<213> ORGANISM: Cannabis sativa

<400> SEQUENCE: 46

Met Glu Gly Asp Ala Leu His Ser Leu Arg Ser Asn Leu Gln Asp Pro
1 5 10 15

Asn Asn Val Leu Gln Ser Trp Asp Pro Thr Leu Val Asn Pro Cys Thr
20 25 30

Trp Phe His Val Thr Cys Asn Asn Asp Asn Ser Val Ile Arg Val Asp
35 40 45

Leu Gly Asn Ala Ala Leu Ser Gly Gln Leu Val Pro Gln Leu Gly Leu
50 55 60

-continued

```
Leu Lys Asn Leu Gln Tyr Leu Glu Leu Tyr Ser Asn Asn Ile Ser Gly
65                  70                  75                  80

Thr Ile Pro Ser Asp Leu Gly Asn Leu Thr Ser Leu Val Ser Leu Asp
                85                  90                  95

Leu Tyr Leu Asn Ser Phe Thr Gly Pro Ile Pro Asp Thr Leu Gly Lys
            100                 105                 110

Leu Ser Lys Leu Arg Phe Leu Arg Leu Asn Asn Asn Ser Leu Thr Gly
        115                 120                 125

Pro Ile Pro Met Ser Leu Thr Asn Ile Thr Ser Leu Gln Val Leu Asp
    130                 135                 140

Leu Ser Asn Asn Lys Leu Thr Gly Glu Val Pro Asp Asn Gly Ser Phe
145                 150                 155                 160

Ser Leu Phe Thr Pro Ile Ser Phe Ala Asn Asn Leu Asn Leu Cys Gly
                165                 170                 175

Pro Val Thr Gly Arg Pro Cys Pro Gly Ser Pro Pro Phe Ser Pro Pro
            180                 185                 190

Pro Pro Phe Val Pro Pro Pro Pro Ile Ser Val Pro Gly Gly Asn Ser
        195                 200                 205

Ala Thr Gly Ala Ile Ala Gly Gly Val Ala Ala Gly Ala Ala Leu Leu
    210                 215                 220

Phe Ala Ala Pro Ala Ile Ala Phe Ala Trp Trp Arg Arg Arg Lys Pro
225                 230                 235                 240

Gln Glu Phe Phe Phe Asp Val Pro Ala Glu Glu Asp Pro Glu Val His
                245                 250                 255

Leu Gly Gln Leu Lys Arg Phe Ser Leu Arg Glu Leu Gln Val Ala Thr
            260                 265                 270

Asp Ser Phe Ser Asn Lys Asn Ile Leu Gly Arg Gly Gly Phe Gly Lys
        275                 280                 285

Val Tyr Lys Gly Arg Leu Ala Asp Gly Ser Leu Val Ala Val Lys Arg
    290                 295                 300

Leu Lys Glu Glu Arg Thr Pro Gly Gly Glu Leu Gln Phe Gln Thr Glu
305                 310                 315                 320

Val Glu Met Ile Ser Met Ala Val His Arg Asn Leu Leu Arg Leu Arg
                325                 330                 335

Gly Phe Cys Met Thr Pro Thr Glu Arg Leu Leu Val Tyr Pro Tyr Met
            340                 345                 350

Ala Asn Gly Ser Val Ala Ser Cys Leu Arg Glu Arg Pro Pro His Gln
        355                 360                 365

Leu Pro Leu Asp Trp Pro Thr Arg Lys Arg Ile Ala Leu Gly Ser Ala
    370                 375                 380

Arg Gly Leu Ser Tyr Leu His Asp His Cys Asp Pro Lys Ile Ile His
385                 390                 395                 400

Arg Asp Val Lys Ala Ala Asn Ile Leu Leu Asp Glu Glu Phe Glu Ala
                405                 410                 415

Val Val Gly Asp Phe Gly Leu Ala Lys Leu Met Asp Tyr Lys Asp Thr
            420                 425                 430

His Val Thr Thr Ala Val Arg Gly Thr Ile Gly His Ile Ala Pro Glu
        435                 440                 445

Tyr Leu Ser Thr Gly Lys Ser Ser Glu Lys Thr Asp Val Phe Gly Tyr
    450                 455                 460

Gly Ile Met Leu Leu Glu Leu Ile Thr Gly Gln Arg Ala Phe Asp Leu
465                 470                 475                 480

Ala Arg Leu Ala Asn Asp Asp Asp Val Met Leu Leu Asp Trp Val Lys
```

```
                485                 490                 495

Gly Leu Leu Lys Glu Lys Lys Leu Glu Met Leu Val Asp Pro Asp Leu
            500                 505                 510

Gln Lys Asn Tyr Ile Glu Ser Glu Val Glu Gln Leu Ile Gln Val Ala
        515                 520                 525

Leu Leu Cys Thr Gln Gly Ser Pro Met Asp Arg Pro Lys Met Ser Glu
    530                 535                 540

Val Val Arg Met Leu Glu Gly Asp Gly Leu Ala Glu Arg Trp Asp Glu
545                 550                 555                 560

Trp Gln Lys Val Glu Val Leu Arg Gln Glu Val Glu Leu Ala Pro His
                565                 570                 575

Pro Asn Ser Asp Trp Ile Val Asp Ser Thr Glu Asn Leu His Ala Val
            580                 585                 590

Glu Leu Ser Gly Pro Arg
        595


<210> SEQ ID NO 47
<211> LENGTH: 1661
<212> TYPE: DNA
<213> ORGANISM: Cannabis sativa

<400> SEQUENCE: 47

aataataata ataataatat tatgagtatt attactaatg atagtaatct cagttgccag      60

ctggaagcgc cgccgtctgc ggtggctccg gtgtcgtcta agaagaccgt tgacactttt     120

ggtcaacgta cctctatata ccgtggtgtt actcgacata gatggactgg tagatatgaa     180

gctcatttgt gggacaacag ttgccgaaga gaaggccaga gtagaaaagg gcgacaagtt     240

tatttgggtg gatatgataa agaagaaaag gcagcaagag cttatgattt ggctgccctt     300

aagtactggg gtcctaccac cactacaaat tttgcagtgt ctaattacga aaaagaatta     360

gaagatatga cgaacatgac taggcaagaa ttcgttgctt cacttcgaag gaaaagtagt     420

ggattttcta gaggagcttc aatatacaga ggcgtcacaa ggcaccacca acatggtcga     480

tggcaggcaa gaattggaag agtagcagga aacaaagatc tctaccttgg cacctttagc     540

acacaagaag aagcagccga ggcatacgac atcgcggcga taaaattccg aggcctaaac     600

gccgtaacaa acttcgacat gagccgttac gacgttaaaa gcatagccaa ctctaatctc     660

cccgttggag gaatgtcaaa caacaccaaa ctttccaaaa cctcacccga acgggcgatt     720

gacaacctat catcgcccgc ttcatcatcc ctcgtcgcct tctcctcctc ggccaccacc     780

aacaacaaca acacaacacc ccaacaacaa caacaacaac aaatgtcctc caatctaagc     840

tttactcttc ccatcaaaca agacctaaca acaacgacaa catcgtcaac ggattattgg     900

tcaaacattt tcggtttcca aaaccctaac cctagtagta ctactagtac tactccttcc     960

ttattgttgg gccataatag tcacaacctc tcggccacat caactaatgc aacaacaact    1020

acaacaacaa caagtaatgg agggtattat ggtaatttca tcgagtcaat ttctaataat    1080

aataataata atactaactt gggttatgga tcaggattaa gtagctggat tagtaatagt    1140

aatcataata ttaacggagg gagtagtaat agtagtaatg ttcataatca tcttcatcat    1200

catcatcatc atgaagttgt tcatgcgaaa caacctagtc tttttcaaac accaatattc    1260

ggcatggaat aataatgatg atgatttttc tcgcacactt gttggaaaac tactggcacg    1320

tgggaatctg tggtgtttga atttgcatgg aaaagggagc tagggttgtt gttgttgtta    1380

ttgtaataat aataataata tggtggaaac tgacaatatt catcataata ttatttttca    1440
```

```
tgagagatga gaatgtagta gtgaaatagc tagtactaac tgaagttggg ttcttttagg   1500

gaccatgttt ttactttttt attatatttt ttgctttttc tttttccttt agtttcatta   1560

ctagatctac tgacattatt attattctag gtgttaagga aaggaatcct ttttgtaatc   1620

cttagttttt ttcatatata ttatataaat gcaccttctt c                       1661


<210> SEQ ID NO 48
<211> LENGTH: 416
<212> TYPE: PRT
<213> ORGANISM: Cannabis sativa

<400> SEQUENCE: 48

Met Ser Ile Ile Thr Asn Asp Ser Asn Leu Ser Cys Gln Leu Glu Ala
1               5                   10                  15

Pro Pro Ser Ala Val Ala Pro Val Ser Ser Lys Lys Thr Val Asp Thr
            20                  25                  30

Phe Gly Gln Arg Thr Ser Ile Tyr Arg Gly Val Thr Arg His Arg Trp
        35                  40                  45

Thr Gly Arg Tyr Glu Ala His Leu Trp Asp Asn Ser Cys Arg Arg Glu
    50                  55                  60

Gly Gln Ser Arg Lys Gly Arg Gln Val Tyr Leu Gly Gly Tyr Asp Lys
65                  70                  75                  80

Glu Glu Lys Ala Ala Arg Ala Tyr Asp Leu Ala Ala Leu Lys Tyr Trp
                85                  90                  95

Gly Pro Thr Thr Thr Thr Asn Phe Ala Val Ser Asn Tyr Glu Lys Glu
            100                 105                 110

Leu Glu Asp Met Thr Asn Met Thr Arg Gln Glu Phe Val Ala Ser Leu
        115                 120                 125

Arg Arg Lys Ser Ser Gly Phe Ser Arg Gly Ala Ser Ile Tyr Arg Gly
    130                 135                 140

Val Thr Arg His His Gln His Gly Arg Trp Gln Ala Arg Ile Gly Arg
145                 150                 155                 160

Val Ala Gly Asn Lys Asp Leu Tyr Leu Gly Thr Phe Ser Thr Gln Glu
                165                 170                 175

Glu Ala Ala Glu Ala Tyr Asp Ile Ala Ala Ile Lys Phe Arg Gly Leu
            180                 185                 190

Asn Ala Val Thr Asn Phe Asp Met Ser Arg Tyr Asp Val Lys Ser Ile
        195                 200                 205

Ala Asn Ser Asn Leu Pro Val Gly Gly Met Ser Asn Asn Thr Lys Leu
    210                 215                 220

Ser Lys Thr Ser Pro Glu Arg Ala Ile Asp Asn Leu Ser Ser Pro Ala
225                 230                 235                 240

Ser Ser Ser Leu Val Ala Phe Ser Ser Ser Ala Thr Thr Asn Asn Asn
                245                 250                 255

Asn Thr Thr Pro Gln Gln Gln Gln Gln Gln Gln Met Ser Ser Asn Leu
            260                 265                 270

Ser Phe Thr Leu Pro Ile Lys Gln Asp Leu Thr Thr Thr Thr Thr Ser
        275                 280                 285

Ser Thr Asp Tyr Trp Ser Asn Ile Phe Gly Phe Gln Asn Pro Asn Pro
    290                 295                 300

Ser Ser Thr Thr Ser Thr Thr Pro Ser Leu Leu Leu Gly His Asn Ser
305                 310                 315                 320

His Asn Leu Ser Ala Thr Ser Thr Asn Ala Thr Thr Thr Thr Thr Thr
                325                 330                 335
```

-continued

```
Thr Ser Asn Gly Gly Tyr Tyr Gly Asn Phe Ile Glu Ser Ile Ser Asn
            340                 345                 350

Asn Asn Asn Asn Asn Thr Asn Leu Gly Tyr Gly Ser Gly Leu Ser Ser
        355                 360                 365

Trp Ile Ser Asn Ser Asn His Asn Ile Asn Gly Gly Ser Ser Asn Ser
    370                 375                 380

Ser Asn Val His Asn His Leu His His His His His His Glu Val Val
385                 390                 395                 400

His Ala Lys Gln Pro Ser Leu Phe Gln Thr Pro Ile Phe Gly Met Glu
                405                 410                 415


<210> SEQ ID NO 49
<211> LENGTH: 55
<212> TYPE: DNA
<213> ORGANISM: Artificial sequence
<220> FEATURE:
<223> OTHER INFORMATION: Single strand DNA oligonucleotide

<400> SEQUENCE: 49

tgtggtctca attgttaact ttttggaagc tggttttaga gctagaaata gcaag          55


<210> SEQ ID NO 50
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 50

tgtggtctca attgcgaaat acttggcaga tgcgttttag agctagaaat agcaag         56


<210> SEQ ID NO 51
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 51

ccaattgtat atgtctatcc tga                                             23


<210> SEQ ID NO 52
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 52

atgagtatta ttactaatga tagtaatctc ag                                   32


<210> SEQ ID NO 53
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 53

ttattccatg ccgaatattg gtgtt                                           25


<210> SEQ ID NO 54
<211> LENGTH: 25
<212> TYPE: DNA
```

<213> ORGANISM: Artificial sequence
<220> FEATURE:
<223> OTHER INFORMATION: Single strand DNA oligonucleotide

<400> SEQUENCE: 54
atggaaggtg atgccttgca tagtc 25

<210> SEQ ID NO 55
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 55
ttacctcgga ccagataact cgacc 25

<210> SEQ ID NO 56
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 56
atgttacgtc ctgtagaaac cc 22

<210> SEQ ID NO 57
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 57
tcattgtttg cctccctgct gcg 23

<210> SEQ ID NO 58
<211> LENGTH: 536
<212> TYPE: PRT
<213> ORGANISM: Cannabis sativa

<400> SEQUENCE: 58

```
Met Ala Ser Leu Ala Phe Gly Ser Asn Gln Phe Met Pro Pro Gly Thr
1               5                   10                  15

Arg Leu Lys Lys Lys Lys Gly Val Leu Pro Leu Lys Val Val Cys Val
            20                  25                  30

Asp Tyr Pro Arg Pro Glu Leu Asp Ser Thr Val Asn Phe Leu Glu Ala
        35                  40                  45

Ala Ala Leu Ser Ala Ser Phe Arg Gly Ser Pro Arg Pro Ala Lys Pro
    50                  55                  60

Leu Lys Val Val Ile Ala Gly Ala Gly Leu Ala Gly Leu Ser Thr Ala
65                  70                  75                  80

Lys Tyr Leu Ala Asp Ala Gly His Lys Pro Ile Leu Leu Glu Ala Arg
                85                  90                  95

Asp Val Leu Gly Gly Lys Val Ala Ala Trp Lys Asp Asp Asp Gly Asp
            100                 105                 110

Trp Tyr Glu Thr Gly Leu His Ile Phe Phe Gly Ala Tyr Pro Asn Val
        115                 120                 125

Gln Asn Leu Phe Gly Glu Leu Gly Ile Asp Asp Arg Leu Gln Trp Lys
    130                 135                 140
```

```
Glu His Ser Met Ile Phe Ala Met Pro Ser Lys Pro Gly Glu Phe Ser
145                 150                 155                 160

Arg Phe Asp Phe Thr Asp Ala Leu Pro Ala Pro Leu Asn Gly Ile Trp
                165                 170                 175

Ala Ile Leu Arg Asn Asn Glu Met Leu Thr Trp Ala Glu Lys Val Lys
            180                 185                 190

Phe Ala Ile Gly Leu Leu Pro Ala Met Val Gly Gly Gln Pro Tyr Val
        195                 200                 205

Glu Ala Gln Asp Gly Phe Thr Val Lys Asp Trp Met Arg Lys Gln Gly
    210                 215                 220

Ile Pro Asp Arg Val Thr Asp Glu Val Phe Ile Ala Met Ser Lys Ala
225                 230                 235                 240

Leu Asn Phe Ile Asn Pro Asp Glu Leu Ser Met Gln Cys Ile Leu Ile
                245                 250                 255

Ala Leu Asn Arg Phe Leu Gln Glu Lys His Gly Ser Lys Met Ala Phe
            260                 265                 270

Leu Asp Gly Asn Pro Pro Glu Arg Leu Cys Met Pro Ile Val Asp His
        275                 280                 285

Ile Gln Ser Leu Gly Gly Glu Val Arg Leu Asn Ser Arg Ile Gln Lys
    290                 295                 300

Ile Asp Leu Asn Asp Asp Gly Thr Val Lys Lys Phe Leu Leu Thr Asn
305                 310                 315                 320

Gly Ser Glu Ile Glu Gly Asp Ala Tyr Val Phe Ala Thr Pro Val Asp
                325                 330                 335

Ile Leu Lys Leu Leu Leu Pro Glu Asn Trp Lys Glu Ile Pro Tyr Phe
            340                 345                 350

Lys Lys Leu Asp Lys Leu Val Gly Val Pro Val Ile Asn Val His Ile
        355                 360                 365

Trp Phe Asp Arg Lys Leu Lys Asn Thr Tyr Asp His Leu Leu Phe Ser
    370                 375                 380

Arg Ser Pro Leu Leu Ser Val Tyr Ala Asp Met Ser Val Thr Cys Lys
385                 390                 395                 400

Glu Tyr Tyr Asn Pro Asn Gln Ser Met Leu Glu Leu Val Phe Ala Pro
                405                 410                 415

Ala Glu Glu Trp Ile Ser Arg Ser Asp Ser Asp Ile Ile Asp Ala Thr
            420                 425                 430

Met Lys Glu Leu Ser Lys Leu Phe Pro Asp Glu Ile Ala Ala Asp Gln
        435                 440                 445

Ser Lys Ala Lys Ile Leu Lys Tyr His Val Val Lys Thr Pro Arg Ser
    450                 455                 460

Val Tyr Lys Thr Val Pro Asp Cys Glu Pro Cys Arg Pro Arg Gln Arg
465                 470                 475                 480

Ser Pro Leu Glu Gly Phe Tyr Leu Ala Gly Asp Tyr Thr Lys Gln Lys
                485                 490                 495

Tyr Leu Ala Ser Met Glu Gly Ala Val Leu Ser Gly Lys Phe Cys Ala
            500                 505                 510

Gln Ala Ile Val Gln Asp Tyr Glu Leu Leu Ala Ala Arg Gly Gln Arg
        515                 520                 525

Ile Leu Ala Glu Ala Gly Ser Arg
    530                 535
```

<210> SEQ ID NO 59
<211> LENGTH: 4384
<212> TYPE: DNA

-continued

<213> ORGANISM: Cannabis sativa

<400> SEQUENCE: 59

```
atgtctcagt ggggttctgt ttcagctact aacttcagct cccaccagag tcgtatcttc     60
gaatttccaa acgtaggaac agtacccaga tgttgttttt cattgagttc caaaaaaatg    120
gcgtctttgg cttttgggtc taatcaattt atgcctcctg gtacaagact gaagaagaag    180
aagggtgttt tgcctttaaa ggtatttttg tgttgaattt gaatgttttt cttgttggga    240
tgaaagaaaa atgagaaatt tattaactga attgagtttt gaaataggtg gtttgtgtgg    300
attatccaag accagagctt gatagtactg ttaacttttt ggaagctgcg gctttgtctg    360
cttcttttcg tggctctcct cgtccagcta agcctttgaa agttgtaatt gctggtgcag    420
gtgaagaaag attgcatttt tatttactta atgatttttt gtgtttctta cttttgagta    480
ttgtttgctt gagaataggg gagaataatc aagtttaaga aaaatcttta cttataataa    540
gaaagttcaa ttagcctatt ttttataatt aagaaagatt tgatatgaaa atatgtattc    600
tgtttttat cttaattata ctgaattttg taactaatct tgtctattcg agtcactttg    660
gtgtgaagct tgcgaatcgt tttcgagttg tattatcgtg tttgactcat caacatcatc    720
aagtttacct gcttgtaata aaaaacatta cttataataa gaaagttcaa ttagcttatg    780
ttttttttc ttcattttat ttgtatgcaa atgattaaaa aagatttggt gtgaaaatgt    840
ttattttgct tttatcttaa ttttactcaa ttttgtaact aatcttgtct gttagagtca    900
cctcagtgtg aagagtgtga atcgttttcg agttgtatta tcattttgta aagcttttat    960
gattttgtat atgtatggtg agtccttcgc taattgtttt ctcaaattct tgtaggtttg   1020
gctggtttat ctactgcgaa atacttggca gatgcaggtc atgaaccgat attactcgaa   1080
gcaagagatg ttttaggtgg aaaggttttt acactgatct agtttacccc ccatgttaac   1140
atcaaactta ttctttcatt acaattcatt ttcattttca cttttcaatt caaggacaaa   1200
ctcatttttt gcttatctta tagtttacat ttcaatcctt tttgttgggt agtttcgaaa   1260
tagttaaact atgagagtgt ttttgctcat tagaaatctt tgccctttag gtggcagcat   1320
ggaaagatga tgacggtgac tggtatgaga ccggtctaca tatattctgt aagttgaatc   1380
tcggaaccat ttcattttac caaattcagt tttacccccct ttgaattttc gagtgcttat   1440
tttctttgta tgcgtcgcaa gttggagctt atcccaacgt acagaacttg ttcggagagc   1500
taggtattga tgatcggttg caatggaaag aacattcaat gatctttgca atgcccagca   1560
agccaggaga attcagccga tttgatttca ccgatgctct gccagctccc ttaaatggta   1620
agagactaca tcatggccaa cctatctctg tacttttttta taactaagaa aatggggttt   1680
tcctccgagg tggagagtaa ctatgttttt gaaacaaatg aattagttgg tcaattactc   1740
aattatgtgc atttgaaatc agaatgtgtt tcgtcgatta gaattctgca atgcgtggat   1800
acgctattgt tcaaactggg tgttcttgaa acctagtata ttctacctct ttaatccaag   1860
tattcccgca aaagctgttt tgttggcatt tttggtgttt aacagttttt gtgctcattt   1920
ggcaggactg atgttcttgt aaccttattc tttgcttctg ttaagtattt tgtttccttt   1980
cggaaatttt actatacact atcttgtttt tcctaggaat atgggccatt ttacggaaca   2040
atgagatgct gacctgggca gaaaaagtca aatttgcaat tgggcttctg cctgcaatgg   2100
ttggcggaca gccttatgtc gaagctcaag atggtttcac cgtcaaagat tggatgagaa   2160
agcaggtaaa ataatggaag aagtgattct tttatagata taagtttgta aaagtattca   2220
aagggattca ttttatggtc tcatgtgaat tttagaagtt tcaagttcga agagtgattt   2280
```

-continued atgatgtttc tgttttcttt cagggcatac ctgatcgtgt aacagatgag gtcttcattg 2340
ccatgtctaa ggccttaaac ttcattaacc cagatgaact ttcaatgcaa tgtatactga 2400
ttgctttaaa ccgatttctt caagtatgtt gcttacattt atccttctag gttgatatat 2460
catatcgata ccataatttt attttattcc cgctcatgta aacaatgaaa ggaatctaga 2520
ggttaagtta ctatttccta tcagactgga atttcgggac ggttaggatt ccacattgac 2580
caattataag attagttagt agcgtataac tatttgggca agctagcgtt tgtgagtgag 2640
ttctacccaa gtgattgtat taagtagtat caaagccatg catcctcaag tgggatcgac 2700
gtcgcgggat gggcaacttg tggttcaagc ccagagtggg acactgcaga gtaggctacc 2760
gtagagtggg ctcccataaa cgtcagctcc aaagagattg gttagtagta tataactatt 2820
tggacaccct cgtctcttag actagttttt gggaatgagt tctacccgag tggttgtatc 2880
ataagactac tgtgatctgt ctaccataaa gtatttgaag caatagtgtt aaaagtagtc 2940
aacataccga actaagaatt tcgaagatgt gaatggaggg aggttaagta atacttatac 3000
actttttgta ccggtacaat ttttaatgtc tcaaagggat catttcttct tcggttttga 3060
acattttgat actactgttt ttgtcataaa aggaagaaac ttatttaagc caaatacttt 3120
ttgatgagtt ttttgtggaa agttacattg aaattaaatg aacaggaaaa gcatggttcc 3180
aagatggctt tcctagatgg aaatccccca gagagactct gtatgcccat agtcgatcat 3240
atccagtcat tgggcggtga agtccgactt aattcccgta tacaaaaaat cgacctgaat 3300
gatgatggaa ctgtaaagag atttttacta actaatggta gtgaaatcga aggggatgca 3360
tatgtgtttg caacaccagg tatgttttcg acccttgttt tcccgtccga tataaagttt 3420
gtattgagtt caaaatcata atatctctaa tgatatcaac aacttacatt ccaaacagtt 3480
gatatcctca agcttctatt gcccgaaaac tggaaagaga ttccgtattt caagaaattg 3540
gataaattag ttggcgtccc cgttattaat gtccacatat ggttagtaac agactctctc 3600
tctctctgtc tctccttaat caagcataga aaaattcaga agttagatag aggtaggtgg 3660
tctttgattc atggattgac caaatttatg aatatttttc ttcaagtagg tatcttaata 3720
atttctaaag attcaatttt atcttaacca tttgtttgaa gcaattttat ataatatttt 3780
cttgataaat ttacatatta agttatgttt atcatgtgta tgtgtgaata atatgatcat 3840
taatattttg taaacaagtt ttctattgtt tggtggtaaa aatgttttct ttgttgcagg 3900
ttcgaccgaa aattgaagaa cacatatgat caccttcttt tcagcaggtt ctgatacttt 3960
acttcttaat tttacccaat ttcattttaa aaatggaacc tttatgctag ctttaaatgc 4020
atattttatc gaattaatag ttacaaacat cttctactca agtagtttcc cgatcaggcg 4080
tgatttaccg atcattccat agtacctagt actacatagc aattgttata gtttcccgat 4140
ctaaaagtat tgtagggtta ggcacagatc ctagttacaa acatgttccg tgtttagtgc 4200
ttctaatgct gcaaatggga tcgcatatta atttgccaaa agaaaatgaa aaagggaaag 4260
atcgtttctt attaatgctt gtaccgactt caaattaacg tcaatatgct tctttttgct 4320
gtgtttgatt cggtaaatta acttatttct tccccatgca gaagtcctct cttgagtgtc 4380
tacg 4384

<210> SEQ ID NO 60
<211> LENGTH: 23
<212> TYPE: DNA
<213> ORGANISM: Artificial sequence
<220> FEATURE:

-continued

```
<223> OTHER INFORMATION: Single strand DNA oligonucleotide

<400> SEQUENCE: 60

cctcgagaaa acttccttaa atg                                          23


<210> SEQ ID NO 61
<211> LENGTH: 421
<212> TYPE: DNA
<213> ORGANISM: Artificial sequence
<220> FEATURE:
<223> OTHER INFORMATION: THCA synthase genomic sequence

<400> SEQUENCE: 61

atgaattgct cagcattttc cttttggttt gtttgcaaaa taatattttt ctttctctca     60

ttccatatcc aaatttcaat agctaatcct cgagaaaact tccttaaatg cttctcaaaa    120

catattccca acaatgtagc aaatccaaaa ctcgtataca ctcaacacga ccaattgtat    180

atgtctatcc tgaattcgac aatacaaaat cttagattca tctctgatac aaccccaaaa    240

ccactcgtta ttgtcactcc ttcaaataac tcccatatcc aagcaactat tttatgctct    300

aagaaagttg gcttgcagat tcgaactcga agcggtggcc atgatgctga gggtatgtcc    360

tacatatctc aagtcccatt tggttgtagt agacttgaga aacatgcatt cgatcaaaat    420

a                                                                   421
```

NUCLEIC ACID CONSTRUCTS AND METHODS OF USING SAME

This application is a National Phase of PCT Patent Application No. PCT/IL2019/050657 having International filing date of Jun. 6, 2019, which claims the benefit of priority under 35 USC § 119(e) of U.S. Provisional Patent Application No. 62/681,698 filed on Jun. 7, 2018. The contents of the above applications are all incorporated by reference as if fully set forth herein in their entirety.

SEQUENCE LISTING STATEMENT

The ASCII file, entitled 77938 SequenceListing.txt, created on 6, Jun. 2019, comprising 126,733 bytes, submitted concurrently with the filing of this application is incorporated herein by reference.

FIELD AND BACKGROUND OF THE INVENTION

The present invention, in some embodiments thereof, relates to nucleic acid constructs and methods of using same such as for use in the production of *Cannabis* plants.

*Cannabis sativa* L. is an annual herb. It is among the earliest cultivated plants which originated in Central Asia. It is valued as a food, oil, fiber, medicinal and recreational drug source and, consequently, has been dispersed throughout the world. *Cannabis sativa* L. (marijuana) contains cannabinoids, a unique class of terpenophenolic compounds which accumulates mainly in glandular trichomes of the plant. Over 100 cannabinoids have been isolated from marijuana, the major biologically active compound being Δ9-tetrahydrocannabinol, commonly referred as THC.

The development of genetic transformation technology for plants has resulted in a great progress toward the genetic design of plants with enhanced production traits, such as herbicide, insect and disease resistance. Commercial cultivars of several transgenic plants have been released. The development of new *Cannabis* cultivars with improved traits could be further facilitated using biotechnological strategies.

Transgenesis enables to exploit an almost unlimited pool of genes for plant improvement, such as genes from bacteria or animal origin, however the implementation of transgenesis in plant breeding is hindered by a hurdle of regulatory rules, which itself feeds on public reluctance. A main concern of the public is the fear of the "un-natural" mix of genes from distant species. Another concern deals with the fact that current methods of transgenesis are "messy" with the transformed DNA integrating within the genome in a random manner, with hard-to-predict consequences.

According to a recent study on the perception of plant biotechnology in Europe, 55% of the surveyed population supported cis-genic products (which do not contain heterologous DNA) while only 22% supported transgenic products (Podevin et al. 2012 *EMBO reports* 13.12 (2012): 1057-1061). Public perception thus seems favorable to new methods whereby the genome, or gene expression are modified with no exogenous DNA being introduced in the plant. This targeted mutagenesis uses custom-made nucleases which catalyze a mutation in the genome but are not present in the final product (Fichtner et al. 2014). The silenced/mutated locus is transmitted to the next generation. This novel approach might facilitate the implementation of biotechnology to *Cannabis* breeding because the modification is precise, no foreign DNA is introduced, regulations are expected to be simpler than for a transgenic plant and a few countries, including Israel and the USA have already approved plants derived from targeted mutagenesis as non-GM products.

The novel technologies for targeted mutagenesis are based on the targeted induction of a double-strand break (DSB) followed by error-prone DNA repair. In plants, DNA DSB repair frequently occurs through a non-homologous end-joining (NHEJ) pathway which is error-prone because exonuclease activity often causes nibbling of the ends, which frequently results in deletions that can range from a few base pairs up to several kilobases *Nucleic Acids Research* 25.22 (1997): 46504657.

In recent years, several breakthroughs have enabled engineering custom-designed nucleases that cleave the DNA at specific targets. The recently developed RNA-based targeted nuclease system, called Clustered Regularly Interspaced Short Palindromic Repeats (CRISPR)/CRISPR-associated systems (Cas) are easy to design because their specificity depends on the complementarity of an RNA molecule to the target (the protospacer region). In addition, there is a requirement for the presence of a protospacer-adjacent motif (PAM) within the target, which is quite minimal (the motif is NGG in *Streptococcus pyogenes*), therefore the system is versatile. The CRISPR-Cas system is derived from bacteria and archaea, where they function to inactivate invading nucleic acids. The bacterial system involves a complex series of RNA processing steps that was adapted in a simplified version, using a single guide RNA molecule (sgRNA or gRNA), first in mammalian cells (Mali 2013, *Science* 339.6121 (2013): 823-826) and recently also in a wide range of plant species (Puchta and Fauser 2014 *The Plant Journal* 79.2 (2014): 348-359).

While the CRISPR-Cas system is very promising, it has been tested mostly in transient experiments, with only few examples of germinal transmission in model plant. Therefore, much work remains to be done to adapt the system to application in crop plants including *Cannabis*.

Additional Background Art Includes:

WO2016189384

SUMMARY OF THE INVENTION

According to an aspect of some embodiments of the present invention there is provided a polynucleotide comprising a nucleic acid sequence encoding an expression product of interest under a transcriptional control of a heterologous cis-acting regulatory element comprising a nucleic acid sequence at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to an aspect of some embodiments of the present invention there is provided a nucleic acid construct comprising the polynucleotide.

According to an aspect of some embodiments of the present invention there is provided a cloning nucleic acid construct comprising a cis-acting regulatory element comprising a nucleic acid sequence at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C) and at least one of a multiple cloning site and a selection marker coding sequence.

According to an aspect of some embodiments of the present invention there is provided a cell comprising the polynucleotide or the nucleic acid construct.

According to some embodiments of the invention, the cell is a bacterial cell.

According to some embodiments of the invention, the cell is a plant cell.

According to an aspect of some embodiments of the present invention there is provided a plant or portion thereof comprising the polynucleotide or the nucleic acid construct.

According to an aspect of some embodiments of the present invention there is provided a method of producing a plant, the method comprises, transforming cells of a plant of interest with the polynucleotide or the nucleic acid construct.

According to some embodiments of the invention, the method further comprises regenerating a plant from the plant cells.

According to some embodiments of the invention, the method further comprises selfing or crossing the plant.

According to some embodiments of the invention, the heterologous cis-acting regulatory element comprises a nucleic acid sequence selected from the group consisting of SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) and 44 (Receptor for activated protein kinase C).

According to some embodiments of the invention, the heterologous cis-acting regulatory element comprises a nucleic acid sequence selected from the group consisting of SEQ ID NO: 2 (CsUbiquitin10), 4 (CsPs2), 6 (CsActin), 8 (CsTubulin) and 10 (Cs EIF).

According to some embodiments of the invention, the expression product of interest comprises a DNA editing agent.

According to some embodiments of the invention, the plant is *Cannabis* saliva.

According to some embodiments of the invention, the expression product of interest comprises an enhanced somatic embryogenesis coding sequence.

According to some embodiments of the invention, the coding sequence is at least 80% identical to SEQ ID NO 45 (CsSERK1) or SEQ ID NO: 47 (CsBBM).

According to some embodiments of the invention, the coding sequence comprises SEQ ID NO 45 (CsSERK1) or SEQ ID NO: 47 (CsBBM).

According to some embodiments of the invention, the DNA editing agent comprises a double strand endonuclease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1B:
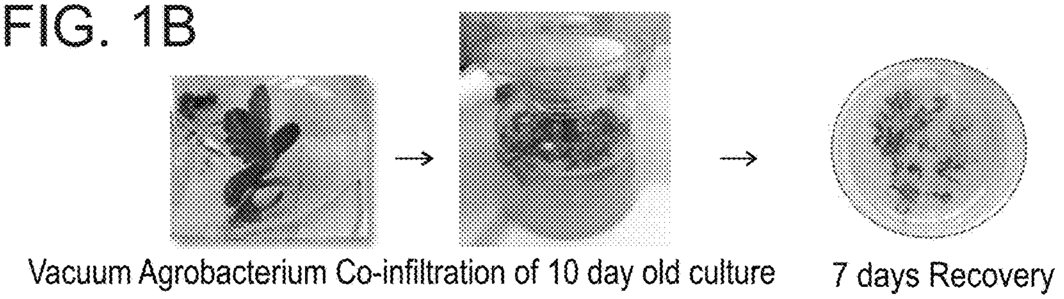
Figure 1C:
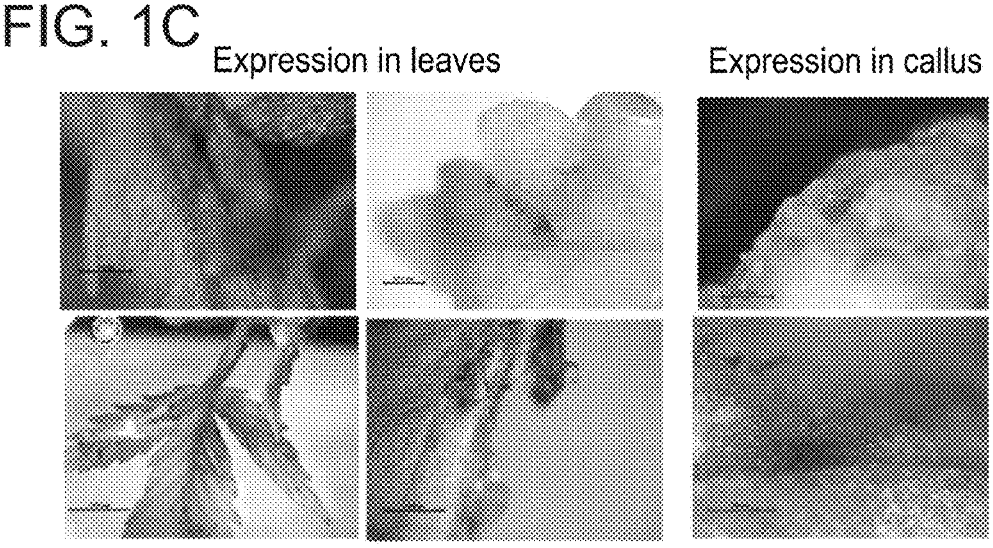
Figure 1D:
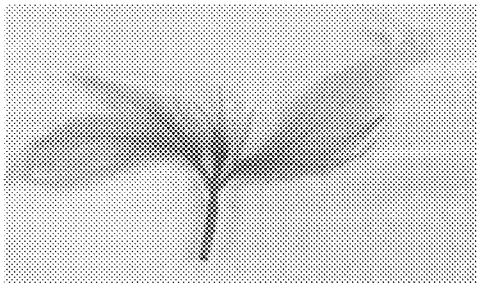

In the drawings:

FIGS. 1A-D show mutated Gus (mGUS) reporter repair in *cannabis* tissue culture using the CRISPR/Cas9 system. FIG. 1A shows schematic illustrations of the two T-DNA used. One contains 35s promoter-driven mGUS (pRCS2-35sP::mGUS) and the other contains 35s promoter-driven hCas9 and U6 promoter-driven gRNA targeting the STOP codon in the mGUS (pRCS2-(Kan)-35sP::hCas9-U6::sgRNA-GUSm). FIG. 1B shows two *A. tumefaciens* lines each mixed together with the binary vectors that infiltrated into 35 days old *cannabis* tissue culture by Agroinfiltration, following with 3 days co-cultivation and 7 days of recovery. FIG. 1C shows histochemical GUS staining of 35-day-old tissue culture, 10 days after *Agrobacterium* infiltration with the CAS9 and the mGUS constructs. FIG. 1D shows histochemical GUS staining of 35-day-old tissue culture, 10 days after *Agrobacterium* infiltration with pRCS2-mGUS (Control).

FIG. 2 show shotgun sequences in which promoter sequences of some embodiments of the invention are underlined and the start codon and stop codon of the open reading frame are both highlighted.

Figure 3A:
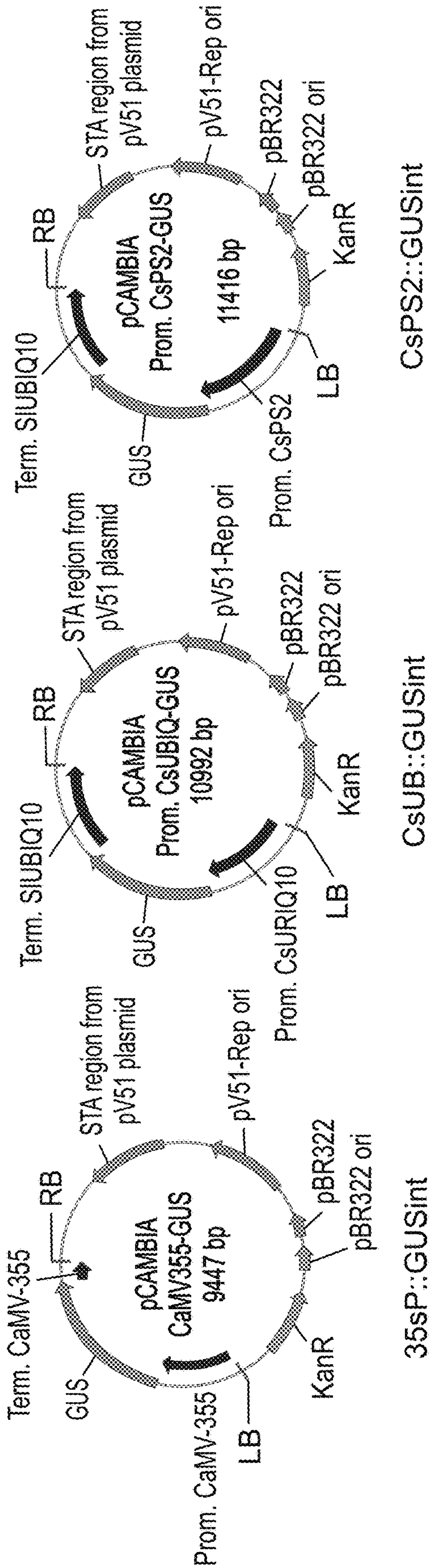
Figure 3B:
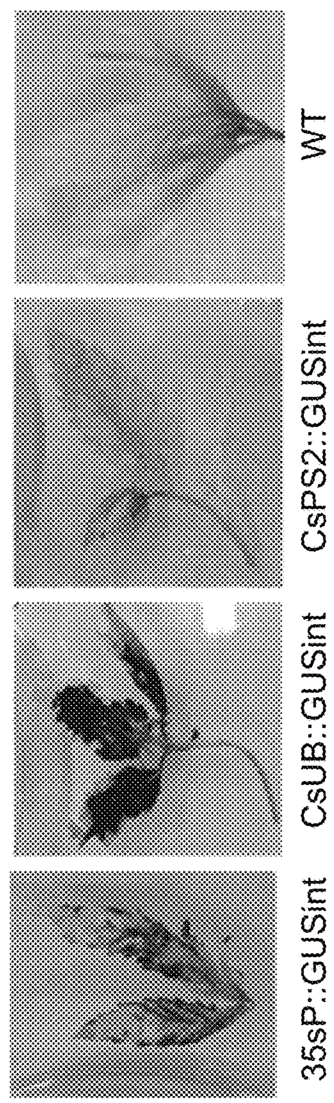
Figure 3C:
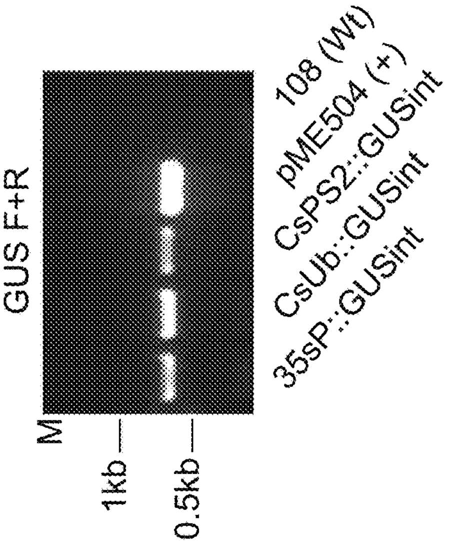

FIGS. 3A-C show plasmid construction and functional analysis of various promoters, as determined by GUS staining.

Figure 4A:
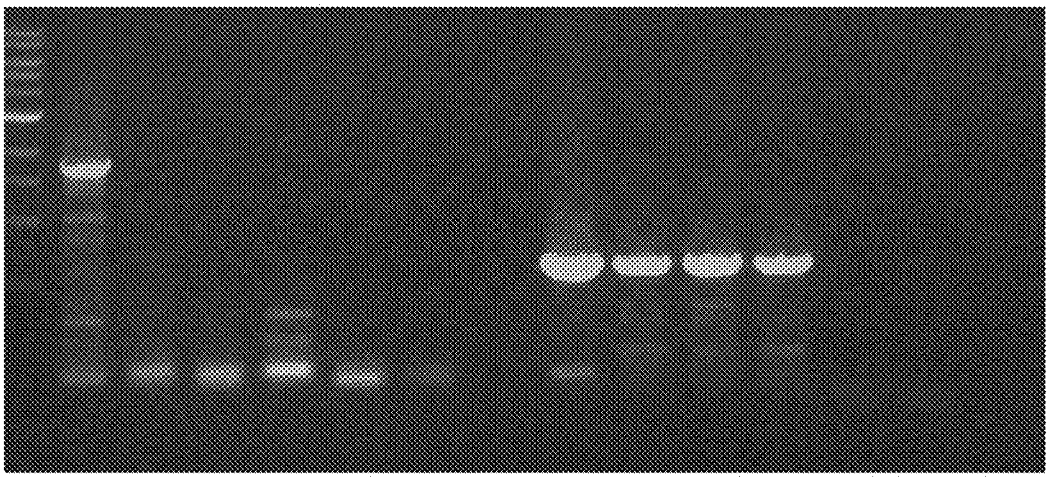
Figure 4B:
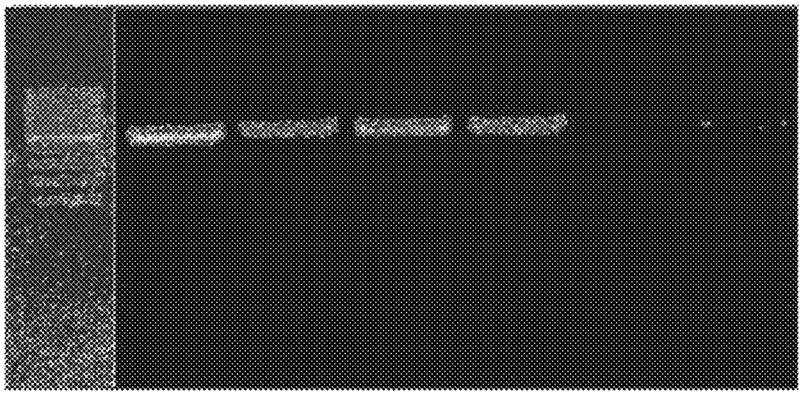

FIGS. 4A-B show PCR analysis that was performed on the three gDNA extracted from transiently transformed leaves, with the oligonucleotides for kanamycin (FIG. 4A) and for the GUS reporter gene (FIG. 4B). pME plasmid DNA was used as a positive control (+), *Cannabis* wild type gDNA (wt) and water (−) were used as negative controls.

Figure 5A:
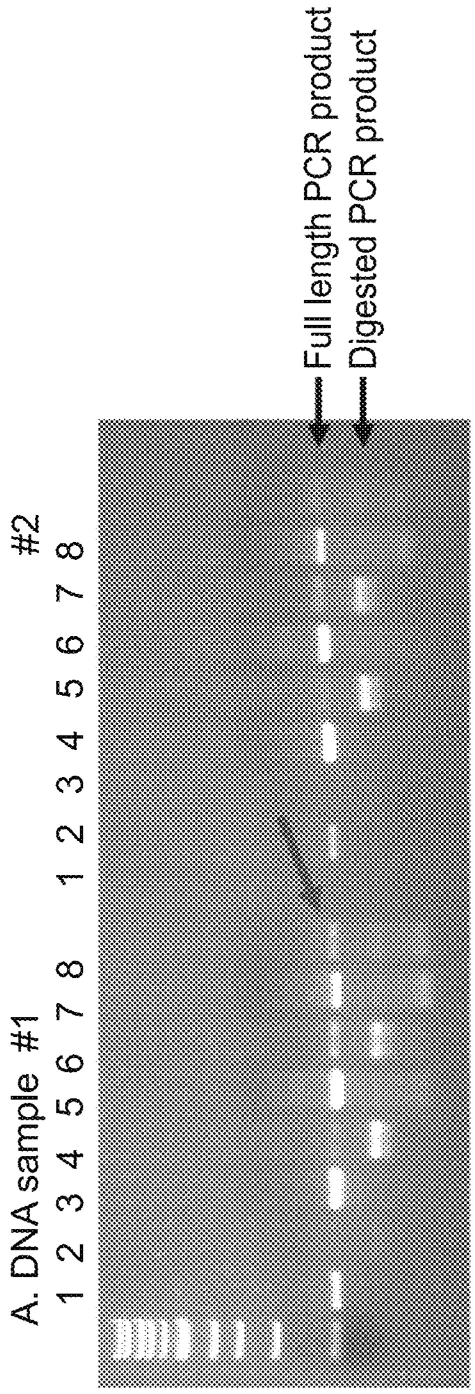
Figure 5B:
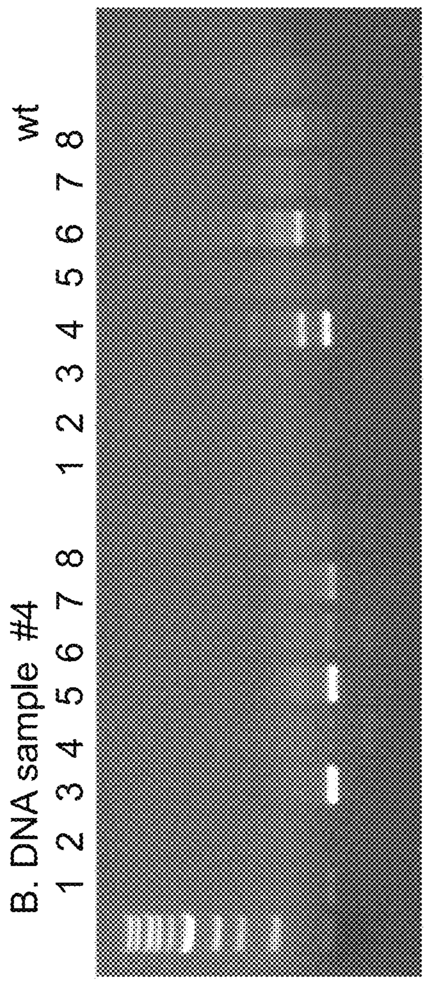

FIGS. 5A-B show rounds of enrichment performed to detect the mutation in the PDS gene. PCR amplification was performed on three distinct genomic DNAs extracted from transiently transformed *Cannabis* leaves and one extracted from wt untreated leaves, with the primers flanking the gRNA target (SEQ ID NOs: 49 and 50). PCR products were then SfaN1 digested. This round of PCR amplification/digestion was repeated four times until an amplicon enriched in SfaN1 resistant DNA fragments was obtained. Full length and digested amplicons are indicated by black arrows. The PCR fragments obtained were cloned.

FIG. 6 shows sequencing results of the mutations obtained in the genome editing assay (SEQ ID NOs: 11-15). DNA fragments potentially containing mutations were sequenced, and compared to the wild-type (WT) sequence. The PAM sequence of the gRNA is indicated by highlight, the SfaN1 restriction site is underlined, and the mutations are indicated in small cap.

Figure 8A:
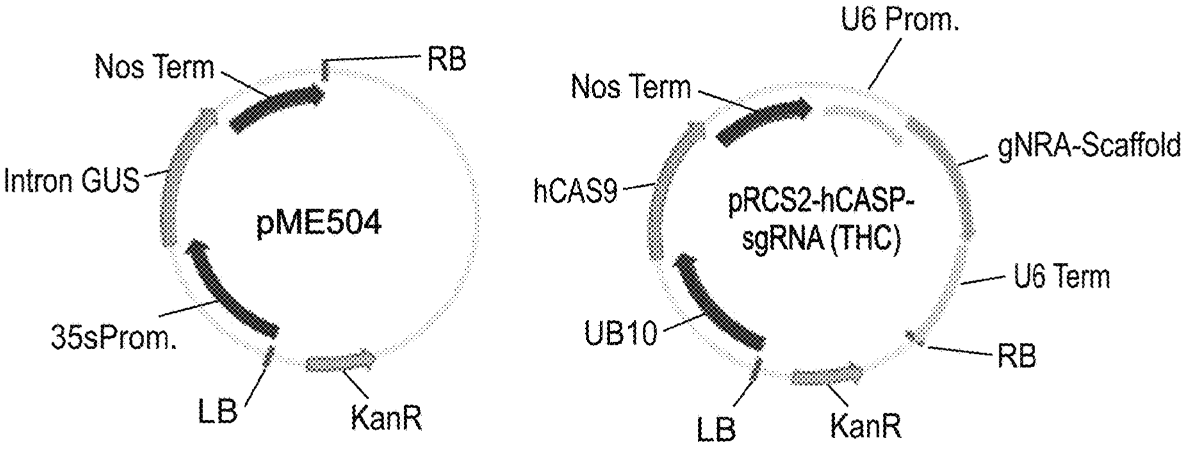
Figure 8B:
Figure 8C:
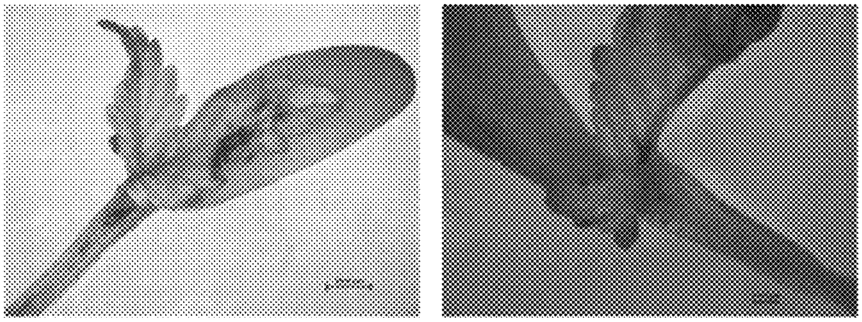

FIG. 7 shows the two gRNAs (underlined, SEQ ID NOs: 17 and 18) that were designed on the THC synthase gene shown in the figure (SEQ ID NO: 16). The start codon and stop codon of the open reading are highlighted FIGS. 8A-C show THC synthase elimination using CRISPR/Cas9. FIG. 8A. Schematic description of the two T-DNA. One contains 35s promoter-driven GUS (pME504) and the other contains UB10 promoter-driven hCas9 and U6 promoter-driven gRNA targeting 2 regions in THC gene (pRCS2-(Kan)-35sP::hCas9-U6::sgRNA-THC). FIG. 8B. Two *A. tumefaciens* lines carrying each binary vector were mixed together and infiltrated into 35 days old *cannabis* tissue culture by Agroinfiltration, following with 3 days cocultivation and 7 days of recovery. FIG. 8C. Histochemical GUS staining of 35-day-old tissue culture, 10 days after *Agrobacterium* infiltration.

FIG. 9 show molecular Analysis of THC synthase genome editing.

FIG. 10 shows sequences of highly and constitutively expressed *Cannabis* genes. Promoter sequences (SEQ ID NOs: 28-44) are marked by underline. Start codon and stop codon of the open reading frame are both highlighted.

FIG. 11 shows the sequences of the CsBBM (SEQ ID NO: 45) and CsSERK1 genes (SEQ ID NO: 47). Transcript sequences were obtained from the database available at medicinalplantgenomics(dot)msu(dot)edu/index(dot)shtml. Start codon and stop codons are highlighted.

Figure 12:
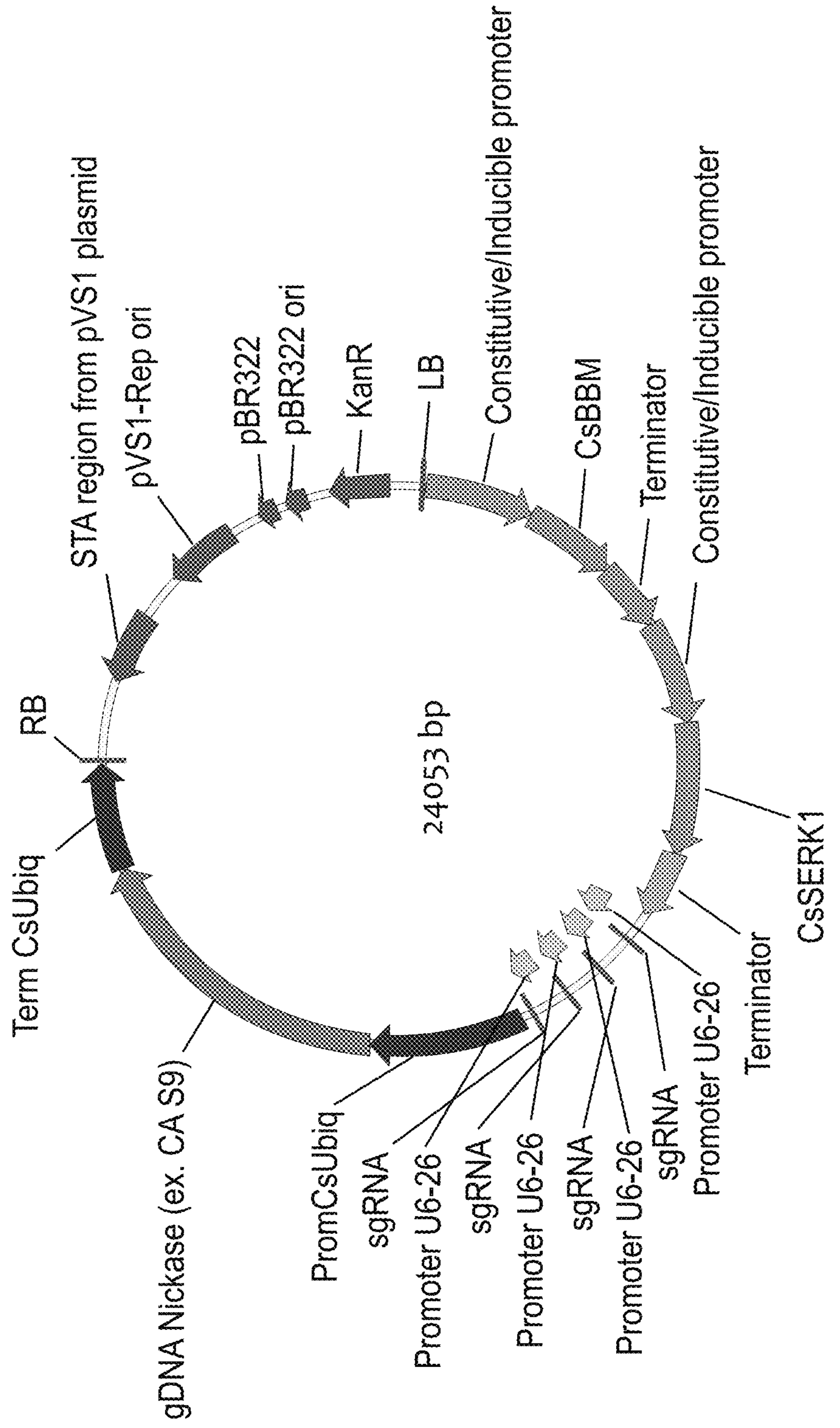

FIG. 12 is a schematic illustration of the plasmid used to induce somatic embryogenesis and genome editing in *Cannabis* plants. The CAS9, under the control of the CsUBIQUITIN10 promoter, the CsBBM, and CsSERK1 genes are under the control of constitutive or inducible promoter.

DESCRIPTION OF SPECIFIC EMBODIMENTS OF THE INVENTION

The present invention, in some embodiments thereof, relates to nucleic acid constructs and methods of using same such as for use in the production of *Cannabis* plants.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Expression of a DNA editing agent (e.g., CAS9) gene under a promoter such as the CaMV 35S promoter, results in low mutagenesis success, where few plants only (<10%) harbor the desired mutation, most often in a heterozygous manner. Consequently, in order to obtain the desired homozygous mutant, one has to first screen for the mutation and further cross the plant mutant for several times. Due to the long life cycle of most plants species (several months at least), this procedure may take several months or even years depending on the zygosity of the plant species of interest. Therefore, there is an unmet need for, and it would be highly advantageous to have means and methods for efficient expression of expression products of interest (e.g., CAS9) in *Cannabis*.

Whilst reducing embodiments of the invention to practice, the present inventors have identified DNA regions in the genome of *Cannabis sativa* that direct high expression of a heterologous reporter gene, e.g., GUS gene in *Cannabis sativa*. Regions located ~1.5-2 kb upstream selected *cannabis* genes were found most efficient at driving high levels of gene expression. Using these genomic regions the present inventors were able to successfully direct the expression of the CAS9 gene and use it for genome editing mutagenesis in *Cannabis* cultivars.

Thus, according to an aspect of the invention there is provided a polynucleotide comprising a nucleic acid sequence encoding an expression product of interest under a transcriptional control of a heterologous cis-acting regulatory element comprising a nucleic acid sequence at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for Activated Protein Kinase C).

According to a specific embodiment, the polynucleotide is isolated.

The term "isolated" as used herein refers to at least partially separated from the natural environment e.g., from a plant cell.

According to a specific embodiment, the polynucleotide is devoid of an intron and/or exon sequences which naturally reside under the cis-acting regulatory element.

According to a specific embodiment, the polynucleotide is devoid of a coding sequence which naturally occurs with the cis-acting regulatory element.

As mentioned, the nucleic acid sequence encoding an expression product of interest is under a transcriptional control of (i.e., operably linked to-) a heterologous cis-acting regulatory element.

As used herein, "operably linked" refers to positioning of a regulatory region (a promoter in this case) relative to a nucleic acid sequence (e.g., a polynucleotide encoding an expression product of interest) in such a way so as to permit or facilitate transcription of the nucleic acid sequence in a host cell (e.g., *Cannabis sativa*).

As used herein "a cis acting regulatory element" refers to a nucleic acid that regulates transcription of a heterologous nucleic acid sequence of interest in cis (as opposed to "in trans").

According to a specific embodiment, the cis acting regulatory element comprises a promoter activity.

As used herein "promoter" refers to a nucleic acid sequence that initiates transcription of a coding sequence (to RNA). The promoter acts in cis i.e., on the same strand and typically upstream of the coding sequence.

When referring to "heterologous" the present disclosure contemplates that the nucleic acid sequence encoding the expression product of interest is not naturally occurring in the cell under the transcriptional control of the heterologous cis-acting regulatory element, as described herein.

In such a case, the polynucleotide or part thereof (e.g., the nucleic acid sequence encoding the expression product of interest) is exogenous to the plant cell or positioned in the genome in a position or an orientation which is not naturally occurring.

The phrase "exogenous polynucleotide" refers to any nucleic acid sequence which is not naturally expressed within the plant and/or which overexpression in the plant is desired. The exogenous polynucleotide may be an isolated single or double stranded nucleic acid sequence in the form of an RNA sequence, a complementary polynucleotide sequence (cDNA), a genomic polynucleotide sequence and/or a composite polynucleotide sequences (e.g., a combination of the above).

The exogenous polynucleotide may comprise a nucleic acid sequence which is identical or partially homologous to an endogenous nucleic acid sequence of the plant.

The term "endogenous" as used herein refers to any polynucleotide or polypeptide which is present and/or naturally expressed within a plant or a cell thereof.

The term "isolated" as used herein refers to at least partially separated from the natural environment e.g., from a plant cell.

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to a specific embodiment, the cis-acting regulatory element comprises a nucleic acid sequence at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to a specific embodiment, the cis-acting regulatory element comprises a nucleic acid sequence at least 85%, 86%, 87%, 88%, 89%, 90%, 91%, 92%, 93%, 94%, 95%, 96%, 97%, 98%, 99%, 99.5% or even 100% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to a specific embodiment, the cis-acting regulatory element comprises a nucleic acid sequence at least 90%, 91%, 92%, 93%, 94%, 95%, 96%, 97%, 98%, 99%, 99.5% or even 100% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to a specific embodiment, the cis-acting regulatory element comprises a nucleic acid sequence at least 95%, 96%, 97%, 98%, 99%, 99.5% or even 100% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to a specific embodiment, the cis-acting regulatory element comprises a nucleic acid sequence at least 97%, 98%, 99%, 99.5% or even 100% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C).

According to a specific embodiment, the cis-acting regulatory element comprises a nucleic acid sequence at least 85% identical to SEQ ID NO: 2 (CsUbiquitin10), 4 (CsPs2), 6 (CsActin), 8 (CsTubulin) or 10 (Cs EIF).

According to a specific embodiment, the cis-acting regulatory element comprises a nucleic acid sequence at least 85%, 86%, 87%, 88%, 89%, 90%, 91%, 92%, 93%, 94%, 95%, 96%, 97%, 98%, 99%, 99.5% or even 100% identical to SEQ ID NO: 2 (CsUbiquitin10), 4 (CsPs2), 6 (CsActin), 8 (CsTubulin) or 10 (Cs EIF).

According to a specific embodiment, the cis-acting regulatory element comprises a nucleic acid sequence at least 90%, 91%, 92%, 93%, 94%, 95%, 96%, 97%, 98%, 99%, 99.5% or even 100% identical to SEQ ID NO: 2 (CsUbiquitin10), 4 (CsPs2), 6 (CsActin), 8 (CsTubulin) or 10 (Cs EIF).

According to a specific embodiment, the cis-acting regulatory element comprises a nucleic acid sequence at least 95%, 96%, 97%, 98%, 99%, 99.5% or even 100% identical to SEQ ID NO: 2 (CsUbiquitin10), 4 (CsPs2), 6 (CsActin), 8 (CsTubulin) or 10 (Cs EIF).

According to a specific embodiment, the cis-acting regulatory element comprises a nucleic acid sequence at least 97%, 98%, 99%, 99.5% or even 100% identical to SEQ ID NO: 2 (CsUbiquitin10), 4 (CsPs2), 6 (CsActin), 8 (CsTubulin) or 10 (Cs EIF).

As used herein, "sequence identity" or "identity" or grammatical equivalents as used herein in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89(22): 10915-9].

Identity can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences of the invention and not over portions thereof.

Promoter activity can be determined by methods well known in the art, typically at the level of RNA but also when possible further downstream, at the level of protein expression.

Methods of determining the level in the plant of the RNA transcribed from the exogenous polynucleotide are well known in the art and include, for example, Northern blot analysis, reverse transcription polymerase chain reaction (RT-PCR) analysis (including quantitative, semi-quantitative or real-time RT-PCR) and RNA-m situ hybridization. At the protein level, these include, but are not limited to Western blots using antibodies capable of specifically binding the polypeptide, Enzyme-Linked Immuno Sorbent Assay (ELISA), radio-immuno-assays (RIA), immunohistochemistry, immunocytochemistry, immunofluorescence and the like. The Examples section below describes GUS staining.

According to some embodiments, the promoter sequences may be truncated or deleted and still retain the capacity of directing the transcription of an operably linked DNA sequence in the host cell. The minimal length of a promoter region can be determined by systematically removing sequences from the 5' and 3'-ends of the isolated polynucleotide by techniques known in the art, including but not limited to removal of restriction enzyme fragments or digestion with nucleases.

According to some embodiments, the nucleic acid construct comprises a functional portion of any of the above described promoter sequences.

As used herein the phrase "functional portion" refers to a minimal nucleic acid sequence which is capable of upregulating (i.e., increasing) transcription of a heterologous sequence.

According to some embodiments the functional portion includes no more than 90% consecutive nucleotides of the above-described promoter sequence.

According to some embodiments the functional portion includes no more than 80% consecutive nucleotides of the above-described promoter sequence.

According to some embodiments the functional portion includes no more than 70% consecutive nucleotides of the above-described promoter sequence.

According to some embodiments the functional portion includes no more than 60% consecutive nucleotides of the above-described promoter sequence.

According to some embodiments the functional portion includes no more than 50% consecutive nucleotides of the above-described promoter sequence.

Assays for qualifying the ability of candidate functional portion sequences or truncated, deleted or mutated promoter sequences to regulate transcription of a heterologous sequence (i.e., to upregulate the transcription of the heterologous sequence) are known in the art. For example, the candidate sequence can be placed upstream of a reporter gene in a nucleic acid construct which is transformed into a plant, and the plant is grown under predetermined conditions. The expression level of the reporter gene is monitored and compared between transgenic and non-transgenic plants, and/or between transgenic planted transformed with a nucleic acid construct which comprises the candidate functional portion upstream of the reporter gene and transgenic plants transformed with a nucleic acid construct which comprises a known promoter upstream of a reporter gene. Examples of known reporter genes which can be used by such assays include, but are not limited to, GUS, luciferase, and GFP (green fluorescent protein).

In another approach, novel hybrid promoters can be designed or engineered by a number of methods. Many promoters contain upstream sequences which activate, enhance or define the strength and/or specificity of the promoter, such as described, for example, by Atchison [Ann. Rev. Cell Biol. 4:127 (1988)]. T-DNA genes, for example contain "TATA" boxes defining the site of transcription initiation and other upstream elements located upstream of the transcription initiation site modulate transcription levels [Gelvin In: Transgenic Plants (Kung, S.-D. and Us, R., eds, San Diego: Academic Press, pp. 49-87, (1988)]. Another chimeric promoter combined a trimer of the octopine synthase (ocs) activator to the mannopine synthase (mas) activator plus promoter and reported an increase in expression of a reporter gene [Min Ni et al., The Plant Journal 7:661 (1995)]. The promoter of some embodiments can be used for the construction of such chimeric or hybrid promoters. Methods for construction of variant promoters include, but are not limited to, combining control elements of different promoters or duplicating portions or regions of a promoter (see for example, U.S. Pat. Nos. 5,110,732 and 5,097,025). Those of skill in the art are familiar with the specific conditions and procedures for the construction, manipulation and isolation of macromolecules (e.g., DNA molecules, plasmids, etc.), generation of recombinant organisms and the screening and isolation of genes, [see for example Sambrook et al., Molecular Cloning: A Laboratory Manual, Cold Spring Harbor Press, (1989); Mailga et al., Methods in Plant Molecular Biology, Cold Spring Harbor Press, (1995); Birren et al., Genome Analysis: volume 1, Analyzing DNA, (1997); volume 2, Detecting Genes, (1998); volume 3, Cloning Systems, (1999); and volume 4, Mapping Genomes, (1999), Cold Spring Harbor, N.Y].

The cis-acting regulatory element can be ligated into a nucleic acid construct such as to comprise the polynucleotide as described herein.

Alternatively, there is provided a cloning nucleic acid construct comprising a cis-acting regulatory element comprising a nucleic acid sequence having a promoter activity being at least 85% identical to SEQ ID NO: 2 (CsUbiquitin10), 4 (CsPs2), 6 (CsActin), 8 (CsTubulin), 10 (Cs EIF), 28 (metallothionein 2A), 30 (Catalase), 32 (Asparagine synthetase), 34 (60S ribosomal protein L3), 38 (40S ribosomal protein S3a), 40 (Phi-1 protein) or 44 (Receptor for activated protein kinase C) such as described hereinabove and at least one of a multiple cloning site and a selection marker coding sequence.

Thus, any of the nucleic acid constructs (also referred to as "vectors") described herein can include further elements for use as a cloning, shuttle, infective, and/or expression construct.

The nucleic acid construct according to some embodiments of the invention further comprises a transcription terminator placed downstream of the coding sequence. Non-limiting examples of such terminators include the NOS terminator, a regulatory sequence from the nopalin-synthase-gene from *Agrobacterium tumfaciens*, and ocs3 terminator (octopine synthase terminator), mas3 terminator mannopine synthesis terminator.

The nucleic acid construct of some embodiments of the invention can further include an appropriate selectable marker and/or an origin of replication. According to some embodiments of the invention, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

Enhancer elements can be included to stimulate transcription up to 1,000 fold from linked homologous or heterologous promoters. Enhancers are active when placed downstream or upstream from the transcription initiation site. Many enhancer elements derived from viruses have a broad host range and are active in a variety of plant tissues.

In the construction of the expression vector, the promoter is typically positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

In order to improve regeneration e.g., following transformation, the expression product of interest can be an enhanced somatic embryogenesis coding sequence.

It is suggested the heterologous expression of an enhanced somatic embryogenesis coding sequence leads to the spontaneous formation of somatic embryos and cotyledon-like structures on seedlings. Ectopic expression of somatic embryogenesis coding sequence can induce any one of neoplastic growth, hormone-free regeneration of explants, and alterations in leaf and flower morphology. The expression pattern of BBM in developing seeds combined with the BBM overexpression phenotype suggests a role for this gene in promoting cell proliferation and morphogenesis during embryogenesis (Boutilier. Kim, et al. "Ectopic expression of BABY BOOM triggers a conversion from vegetative to embryonic growth." *The Plant Cell* 14.8 (2002): 1737-1749).

According to a specific embodiment the coding sequence is at least 80% identical to SEQ ID NO 45 (CsSERK1) or SEQ ID NO: 47 (CsBBM).

According to a specific embodiment the coding sequence is at least 80%, 81%, 82%, 83% 84%, 85%, 86%, 87%, 88%, 89%, 90%, 91%, 92%, 93%, 94%, 95%, 96%, 97%, 98%, 99%, 99.5% or even 100% identical to SEQ ID NO 45 (CsSERK1) or SEQ ID NO: 47 (CsBBM).

According to a specific embodiment, the coding sequence comprises SEQ ID NO: 45 (CsSERK1) or SEQ ID NO: 47 (CsBBM).

The nucleic acid construct of some embodiments of the invention can be utilized to transform a host cell. Non-limiting examples of host cells which can be used along with some embodiments of the invention include, but are not limited to, plant cells and bacterial cells (e.g., Agrobacteria).

According to a specific embodiment, the nucleic acid construct is a binary vector.

According to a specific embodiment, the nucleic acid construct is based on known/commercial vectors. Examples for binary vectors are pBIN19, pBI101, pBinAR, pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)). Examples of other vectors to be used in other methods of DNA delivery (e.g. transfection, electroporation, bombardment, viral inoculation) are: pGE-sgRNA (Zhang et al. Nat. Comms. 2016 7:12697), pJIT163-Ubi-Cas9 (Wang et al. Nat. Biotechnol 2004 32, 947-951), pICH47742::2x35S-5'UTR-hCas9(STOP)-NOST (Belhan et al. Plant Methods 2013 11; 9(1):39), pAHC25 (Christensen, A. H. & P. H. Quail, 1996. Ubiquitin promoter-based vectors for high-level expression of selectable and/or screenable marker genes in monocotyledonous plants. Transgenic Research 5: 213-218), pi IBT-sGFP(S65T)-NOS (Sheen et al. Protein phosphatase activity is required for light-inducible gene expression in maize, EMBO J. 12 (9), 3497-3505 (1993).

As mentioned, the polynucleotide encodes an expression product of interest.

As used herein "expression product" refers to an RNA or protein (also referred to herein as "polypeptide").

According to a specific embodiment, the expression product is a protein.

According to a specific embodiment, the expression product brings about overexpression of an endogenous gene or homolog thereof or of a foreign gene expression product altogether. In embodiments of such cases, the expression product is heterologous to the plant/tissue being transformed.

It will be appreciated that the heterologous expression product can bring about down regulation of an endogenous gene such as by way of genome editing or RNA silencing.

The term "heterologous" as used herein refers to exogenous, not-naturally occurring within a native cell of a *cannabis* plant of a specific developmental stage, or not expressed in a plant, not expressed in a particular plant species, or is expressed at a different expression level or localization in the plant, than the native protein.

However, using genome editing for instance can also effect overexpression of an endogenous gene (e.g., by way of a "gain of function").

Genome editing as contemplates herein also mediates loss of function.

As used herein, the term "polypeptide" is used interchangeably with the terms "peptides", "oligopeptides" and "proteins" and refers to a biomolecule composed of amino acids of any length, linked together by peptide bonds.

The polypeptide of interest can be, for example, a plant polypeptide, a bacterial polypeptide, a viral polypeptide a mammalian polypeptide or a synthetic polypeptide (e.g., chimeric nuclease, nuclease e.g. cas9). Thus, the heterologous polypeptide of interest may be a plant polypeptide or protein that is a variant or mutated form of a plant polypeptide or protein or a polypeptide or protein not naturally found in the plant species, line or variety.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment.

According to one embodiment, the heterologous polypeptide of interest may include, but is not limited to, a reporter polypeptide, an antiviral polypeptide, a viral moiety, an antiviral polypeptide, an antifungal polypeptide, an antibacterial polypeptide, an insect resistance polypeptide, a herbicide resistance polypeptide, a biotic or abiotic stress tolerance polypeptide, a pharmaceutical polypeptide, a growth inducing polypeptide, a growth inhibiting polypeptide, an enzyme, a transcription factor and a transposase.

Exemplary proteins which may be produced, include, but are not limited to: nucleases, kinases, proteases, enzymes, hormones, proteins that provide resistance to diseases, antimicrobial proteins, antiviral proteins, and proteinaceous DNA editing agents.

According to one embodiment, the heterologous polypeptide of interest comprises two or more (e.g., 2, 3, 4) heterologous polypeptides.

According to one embodiment, the heterologous polypeptide of interest enables modifying the plant genome, e.g., nuclease.

As used herein the term "nuclease" refers to any polypeptide, or complex comprising a polypeptide, that can generate a strand break in the genome, e.g. in genomic DNA. According to an embodiment, the cleavage is site specific usually conferred by an auxiliary subunit, alternatively the nuclease is inherently specific to a target sequence of interest.

As used herein, the term "cleavage" or "DNA cleavage" refers to the breakage of the covalent backbone of a DNA molecule. Both single-stranded cleavage and double-stranded cleavage are possible, and double-stranded cleavage can occur as a result of two distinct single-stranded cleavage events. DNA cleavage can result in the production of either blunt ends or staggered ends.

Exemplary nucleases which may be used in accordance with the present teachings include restriction enzymes (e.g. type II restriction endonuclease), topoisomerases [e.g. DNA gyrase, eukaryotic topoisomerase II (topo II), and bacterial topoisomerase IV (topo IV)], recombinases (e.g. Cre recombinase, Hin recombinase), integrases, DNAses, endo-exonucleases (e.g. micrococcal nuclease) and homing endonucleases.

According to one embodiment, the nuclease utilized may comprise a non-specific DNA cleavage domain, for example, a type II restriction endonuclease such as the cleavage domain of the FokI restriction enzyme (GenBank accession number J04623).

According to one embodiment, the nuclease is a meganuclease.

As used herein, the term "meganuclease" refers to a double-stranded endonuclease having a large polynucleotide recognition site, e.g. DNA sequences of at least 12 base pairs (bp) or from 12 bp to 40 bp. The meganuclease may also be referred to as rare-cutting or very rare-cutting endonuclease. The meganuclease of the invention may be monomeric or dimeric. The meganuclease may include any natural meganuclease such as a homing endonuclease, but may also include any artificial or man-made meganuclease endowed with high specificity, either derived from homing endonucleases of group I introns and inteins, or other proteins such as zinc finger proteins or group II intron proteins, or compounds such as nucleic acid fused with chemical compounds.

Artificial meganucleases of the invention include, but are not limited to, custom-made meganucleases which are meganucleases derived from any initial meganuclease, either natural or not, presenting a recognition and cleavage site different from the site of the initial meganuclease, i.e. the custom-made meganuclease cleaves a novel site with an efficacy at least 10 fold, at least 50 fold or at least 100 fold more than the natural meganuclease.

Custom-made meganucleases may be produced by any method known in the art, for example, by preparing a library of meganuclease variants and isolating, by selection and/or screening, the variants able to cleave the targeted DNA sequence. The diversity could be introduced in the meganuclease by any method known to one skilled in the art, for example, the diversity may be introduced by targeted mutagenesis (i.e. cassette mutagenesis, oligonucleotide directed codon mutagenesis, targeted random mutagenesis), by random mutagenesis (i.e. mutator strains, *Neurospora crassa* system (U.S. Pat. No. 6,232,112; WO 01/70946, error-prone PCR), by DNA shuffling, by directed mutation or a combination of these technologies (See Current Protocols in Molecular Biology, Chapter 8 "Mutagenesis in cloned DNA", Eds Ausubel et al., John Wiley and Sons). The diversity may be introduced at positions of the residues contacting the DNA target or interacting (directly or indirectly) with the DNA target, or may be introduced specifically at the positions of the interacting amino acids. In libraries generated by targeted mutagenesis, the 20 amino acids can be introduced at the chosen variable positions. According to an embodiment, the amino acids present at the variable positions are the amino acids well-known to be generally involved in protein-DNA interaction. More particularly, these amino acids are generally the hydrophilic amino acids, e.g. comprise D, E, H, K, N, Q, R, S, T, Y. Synthetic or modified amino acids may also be used.

The custom-made meganuclease may be derived from any initial meganuclease.

According to one embodiment, the initial meganuclease is selected so as its natural recognition and cleavage site is the closest to the targeted DNA site. According to an embodiment, the initial meganuclease is a homing endonuclease. Homing endonucleases fall into 4 separated families on the basis of well conserved amino acids motifs, namely the LAGLIDADG family, the GIY-YIG family, the His-Cys box family, and the HNH family (Chevalier et al., 2001, N.A.R, 29, 3757-3774). According to one embodiment, the homing endonuclease is a I-Dmo I, PI-Sce I, I-SceI, PI-Pfu I, I-Cre I, I-Ppo I, or a hybrid homing endonuclease I-Dmo I/I-Cre I called E-Dre I (as taught in Chevalier et al., 2001, Nat Struct Biol, 8, 312-316).

Further details relating to meganucleases are found in U.S. Pat. No. 8,697,395 which is incorporated herein by reference.

According to another embodiment, of the present invention, the nuclease comprises an oligonucleotide-dependant nuclease such as Cas or a RISC.

RISC enzymes are taught in Martinez J, Tuschl T. RISC is a 5' phosphomonoester-producing RNA endonuclease. Genes Dev. 2004; 18:975-980. Also contemplated are sequence modifications to improve plant expression i.e., homologs that are at least 60%, 65%, 70%, 75%, 80%, 85%, 90%, 95%. Homology and identity are also contemplated herein (e.g., using Blast(N)/(P) with default parameters).

According to one embodiment, the Cas9 or RISC is attached to a single guide RNA (sgRNA) to cleave genomic DNA in a sequence specific manner, hence the polynucleotide may encode the RNA targeting moiety such as a gRNA.

As used herein "a single guide RNA" or "sgRNA" refers to a chimeric RNA molecule which is composed of a clustered regularly interspersed short palindromic repeats (CRISPR) RNA (crRNA) and trans-encoded CRISPR RNA (tracrRNA). The crRNA defines a site-specific targeting of the Cas9 protein. The sequence is 19-22 nucleotides long e.g., 20 consecutive nucleotides complementary to the target and is typically located at the 5' end of the sgRNA molecule. The crRNA may have 100% complementation with the target sequence although at least 80%, 85%, 90%, and 95% global homology to the target sequence are also contemplated according to the present teachings.

The tracrRNA is 100-300 nucleotides long and provides a binding site for the nuclease e.g., Cas9 protein forming the CRISPR/Cas9 complex.

According to a specific embodiment a plurality of sgRNAs are provided to the plant cell that are complementary to different target nucleic acid sequences and the nuclease e.g., Cas9 enzyme cleaves the different target nucleic acid sequences in a site specific manner.

It will be appreciated that the sgRNA may be encoded from the same expression vector as the nuclease, e.g. Cas9. Additionally or alternatively, the sgRNA may be encoded from another nucleic acid construct and thus the CRISPR-Cas9 complex is encoded from a nucleic acid construct system.

According to another embodiment, sgRNA is encoded from the plant expression vector of the invention. In such a case the nuclease, e.g. Cas9, may be encoded from another nucleic acid construct and thus the CRISPR-Cas9 complex is encoded from a nucleic acid construct system.

Likewise, the plurality of sgRNAs may be encoded from a single vector or from a plurality of vectors as described herein. The use of a plurality of sgRNAs allows multiplexing.

Thus, the RNA-guided endonuclease of the invention comprises at least one nuclease (e.g. Cas9 or RISC) and at least one RNA binding domain (e.g. CRISPR). CRISPR/Cas proteins of the invention may comprise a nuclease domain, DNA binding domain, helicase domain, RNAse domain, protein-protein interaction domain and/or a dimerization domain.

According to one embodiment, the CRISPR/Cas protein can be a wild type CRISPR/Cas protein, a modified CRISPR/Cas protein, or a fragment of a wild type or modified CRISPR/Cas protein. Furthermore, the CRISPR/Cas protein can be modified to increase nucleic acid binding affinity and/or specificity, or to alter an enzymatic activity of the protein. For example, nuclease (i.e., Cas9) domains of the CRISPR/Cas protein can be modified.

Non-limiting examples of suitable Cas proteins which may be used in accordance with the present teachings include Cas3, Cas4, Cas5, Cas5e (or CasD), Cas6, Cas6e, Cas6f, Cas7, Cas8a1, Cas8a2, Cas8b, Cas8c, Cas9, Cas10, Casl Od, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmrl, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966.

According to a specific embodiment, the cas nuclease is Cas9. Cas9 is a monomeric DNA nuclease guided to a DNA target sequence adjacent to the protospacer adjacent motif (PAM). The Cas9 protein comprises two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA.

In some embodiments, the CRISPR/Cas system comprises a wild type Cas9 protein or fragment thereof.

In other embodiments, the CRISPR/Cas system comprises a modified Cas9 protein. For example, the amino acid sequence of the Cas9 protein may be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

According to one embodiment, the Cas9 protein can be modified to lack at least one functional nuclease domain. According to one embodiment, the Cas9 protein can be modified to lack all nuclease activity. According to another embodiment, the CRISPR/Cas system is fused with various effector domains, such as DNA cleavage domains. The DNA cleavage domain can be obtained from any endonuclease or exonuclease. Non-limiting examples of endonucleases from which a DNA cleavage domain can be derived include, but are not limited to, restriction endonucleases and homing endonucleases (see, for example, New England Biolabs Catalog or Belfort et al. (1997) Nucleic Acids Res.). In exemplary embodiments, the cleavage domain of the CRISPR/Cas system is a Fokl endonuclease domain or a modified Fokl endonuclease domain.

Various methods for designing CRISPR/Cas are known in the art and may be implemented in accordance with the present teachings. Further details relating to CRISPR/Cas can be found in PCT publication no. WO 2014089290 which is incorporated herein by reference in its entirety. According to another embodiment of the present invention, the nuclease comprises a chimeric nuclease.

As used herein the phrase "chimeric nuclease" refers to a synthetic chimeric polypeptide which forms a single open reading frame (ORF) and mediates DNA cleavage in a sequence specific manner.

According to a specific embodiment, the chimeric nucleases of this aspect of the present invention comprise separate domains for nucleic acid binding (e.g. DNA binding) and for nucleic acid cleavage (e.g. DNA cleavage), such that cleavage is sequence specific.

As used herein the phrase "sequence specific" refers to a distinct chromosomal location at which nucleic acid cleavage (e.g. DNA cleavage) is introduced.

As used herein the phrase "nucleic acid binding domain" refers to a native or synthetic amino acid sequence such as of a protein motif that binds to double- or single-stranded DNA or RNA in a sequence-specific manner (i.e. target site).

In order to induce efficient gene targeting, the nucleic acid (e.g. DNA) binding domain of the present invention needs to be coupled to a DNA cleavage domain (e.g. nuclease) as to permit DNA cleavage within a workable proximity of the target sequence. A workable proximity is any distance that still facilitates the sequence targeting. Optionally, the DNA binding domain overlaps the target sequence or may bind within the target sequence.

According to one embodiment, the chimeric nuclease induces a single stranded or a double stranded cleavage in the target site.

In generating chimeric nucleases any DNA or RNA binding domain that recognizes the desired target sequence (e.g. DNA binding sequence) with sufficient specificity may be employed. A variety of such DNA and RNA binding domains are known in the art.

Examples of DNA binding domains include, but are not limited to, a meganuclease binding domain, a helix-turn-helix (pfam 01381) binding domain, a leucine zipper (ZIP) binding domain, a winged helix (WH) binding domain, a winged helix turn helix domain (wHTH) binding domain, a helix-loop-helix binding domain, a transcription activator-like (TAL) binding domain, a recombinase, and a zinc finger binding domain.

In an exemplary embodiment of the present invention, the DNA binding domain is a zinc finger binding domain.

Thus, according to an embodiment of this aspect, the chimeric nuclease is a chimeric protein comprising a specific zinc finger binding domain (e.g., pfam00096) and the DNA cleavage domain, such as that of the Fokl restriction enzyme (also referred to herein as the Fokl cleavage domain), termed herein zinc finger nuclease (ZFN).

The zinc finger domain is 30 amino acids long and consists of a recognition helix and a 2-strand beta-sheet. The domain also contains four regularly spaced ligands for Zinc (either histidines or cysteines). The Zn ion stabilizes the 3D structure of the domain. Each finger contains one Zn ion and recognizes a specific triplet of DNA basepairs.

Zinc finger domains can be engineered to bind to a predetermined nucleotide sequence. Each individual zinc finger (e.g. Cys2/His2) contacts primarily three consecutive base pairs of DNA in a modular fashion [Pavletich et al., Science (1991) 252:809-817; Berg et al., Science (1996) 271:1081-1085]. By manipulating the number of zinc fingers and the nature of critical amino acid residues that contact DNA directly, DNA binding domains with novel specificities can be evolved and selected [see, e.g., Desjarlais et al., Proc. Natl. Acad. Sci. USA (1992) 89:7345-7349; Rebar et al., Science (1994) 263:671-673; Greisman et al., Science (1997) 275:657-661; Segal et al., Proc. Natl. Acad. Sci. USA (1999) 96:2758-2763]. Hence, a very wide range of DNA sequences can serve as specific recognition targets for zinc finger proteins. Chimeric nucleases with several different specificities based on zinc finger recognition have been previously disclosed [see for example, Huang et al., J. Protein Chem. (1996) 15:481-489; Kim et al., Biol. Chem. (1998) 379:489-495].

Various methods for designing chimeric nucleases with zinc finger binding domains are known in the art.

In one embodiment the DNA binding domain comprises at least one, at least two, at least 3, at least 4, at least 5 at least 6 zinc finger domains, binding a 3, 6, 9, 12, 15, or 18 nucleotide sequence, respectively. It will be appreciated by the skilled artisan that the longer the recognition sequence is, the higher the specificity that will be obtained.

Specific DNA binding zinc fingers can be selected by using polypeptide display libraries. The target site is used with the polypeptide display library in an affinity selection step to select variant zinc fingers that bind to the target site. Typically, constant zinc fingers and zinc fingers to be randomized are made from any suitable C2H2 zinc fingers protein, such as SP-1, SP-1C, TFIIIA, GLI, Tramtrack, YY1, or ZIF268 [see, e.g., Jacobs, EMBO J. 11:4507 (1992); Desjarlais & Berg, Proc. Natl. Acad. Sci. U.S.A. 90:2256-2260 (1993)]. The polypeptide display library encoding variants of a zinc finger protein comprising the randomized zinc finger, one or more variants of which will be selected, and, depending on the selection step, one or two constant zinc fingers, is constructed according to the methods known to those in the art. Optionally, the library contains restriction sites designed for ease of removing constant zinc fingers, and for adding in randomized zinc fingers. Zinc fingers are randomized, e.g., by using degenerate oligonucleotides, mutagenic cassettes, or error prone PCR. See, for example, U.S. Pat. Nos. 6,326,166, 6,410,248, and 6,479,626.

Zinc fingers can also be selected by design. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

According to another embodiment, the chimeric nuclease is a TALENs or a compact-TALENs (cTALENs).

As used herein, the term "TALENs" or "Transcription Activator-Like Effector Nucleases" refers to the artificial restriction enzymes generated by fusing the TAL effector DNA binding domain to a DNA cleavage domain. TALENs of the invention enable efficient, programmable, and specific DNA cleavage.

It will be appreciated that Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN. Further details relating to TALENS can be found in U.S. Pat. Nos. 8,450,471; 8,440,431; 8,440,432; and U.S. Pat. Applic. No. 20140256798 all of which are incorporated herein by reference in their entirety.

TALEs are proteins secreted by *Xanthomonas* bacteria. The DNA binding domain of TALEs contains a highly conserved 33-34 amino acid sequence with the exception of the 12th and 13th amino acids. These two locations are highly variable [Repeat Variable Diresidue (RVD)] and show a strong correlation with specific nucleotide recognition. This simple relationship between amino acid sequence and DNA recognition has allowed for the engineering of specific DNA binding domains by selecting a combination of repeat segments containing the appropriate RVDs.

TALENs of the invention are typically constructed using a non-specific DNA cleavage domain, such as the non-specific DNA cleavage domain of Fokl endonuclease. Thus, wild-type Fokl cleavage domain may be used as well as Fokl cleavage domain variants with mutations designed to improve cleavage specificity and cleavage activity. The Fokl domain functions as a dimer, requiring two constructs with unique DNA binding domains for sites in the target genome with proper orientation and spacing. Both the number of amino acid residues between the TALEN DNA binding domain and the DNA cleavage domain (e.g. Fokl cleavage domain) and the number of bases between the two individual TALEN binding sites are parameters for achieving high levels of activity. The number of amino acid residues between the TALEN DNA binding domain and the DNA cleavage domain (e.g. Fokl cleavage domain) may be modified by introduction of a spacer between the plurality of TAL effector repeat sequences and the nuclease (e.g. Fokl endonuclease domain). The spacer sequence may be 12 to 30 nucleotides.

Furthermore, compact TALENs (cTALENs) may be used according to the present teachings. These cTALENs are typically designed with the partially specific I-TevI catalytic domain and are monomeric DNA-cleaving enzymes, i.e. TALENs which are half-size, single-polypeptide compact transcription activator-like effector nucleases (see Beurdeley M. et al., Nature Communications (2013) 4: 1762, which is incorporated herein by reference in its entirety).

The relationship between amino acid sequence and DNA recognition of the TALEN binding domain allows for designable proteins. In this case software programs (e.g. DNA-Works) may be used which calculate oligonucleotides suitable for assembly in a two step PCR; oligonucleotide assembly followed by whole gene amplification. Modular assembly schemes for generating engineered TALE constructs may also be used. Both methods offer a systematic approach to engineering DNA binding domains that are conceptually similar to the modular assembly method for generating zinc finger DNA recognition domains (described hereinabove).

Qualifying the nucleases (e.g. ZFN, TALENs and CRISPR/Cas) and meganucleases thus generated for specific target recognition can be effected using methods which are well known in the art.

A method for designing the nucleases (e.g. chimeric nucleases, ZFN, TALENs, Cas9, RISC, meganucleases) for use in gene targeting may include a process for testing the toxicity of the nuclease on a cell. Such a process may comprise expressing in the cell, or otherwise introducing into a cell, the nuclease and assessing cell growth or death rates by comparison against a control. The tendency of a nuclease to cleave at more than one position in the genome may be evaluated by in-vitro cleavage assays, followed by electrophoresis (e.g. pulsed field electrophoresis may be used to resolve very large fragments) and, optionally, probing or Southern blotting. In view of the present disclosure, one of ordinary skill in the art may devise other tests for cleavage specificity.

The heterologous polypeptide of interest (e.g. nuclease) disclosed herein may further comprise at least one nuclear localization signal (NLS) which facilitates the transport of the nuclease to the DNA-containing organelle. In general, an NLS comprises a stretch of basic amino acids which is recognized by specific receptors at the nuclear pores. The NLS can be located at the N-terminus, the C-terminal, or in an internal location of the nuclease.

Essentially any NLS may be employed, whether synthetic or a naturally occurring NLS, as long as the NLS is one that is compatible with the target cell (i.e. plant cell).

Although nuclear localization signals are discussed herewith, the present teachings are not meant to be restricted to these localization signals, as any signal directed to a DNA-containing organelle is envisaged by the present teachings. Such signals are well known in the art and can be easily retrieved by the skilled artisan.

Nuclear localization signals which may be used according to the present teachings include, but are not limited to, SV40 large T antigen NLS, acidic M9 domain of hnRNP A1, the sequence KIPIK in yeast transcription repressor Matα2 and the complex signals of U snRNPs, tobacco NLS and rice NLS.

In other exemplary embodiments, the localization signal for a DNA containing organelle can be a mitochondrial localization signal (MLS) or a chloroplast localization signal (CLS).

Mitochondrion localization signals (MLS) which may be used according to the present teachings include, but are not limited to the transition signals of, Beta ATPase subunit [cDNAs encoding the mitochondrial pre-sequences from *Nicotiana plumbaginifolia* f3-ATPase (nucleotides 387-666)], Mitochondrial chaperonin CPN-60 [cDNAs encoding the mitochondrial pre-sequences from *Arabidopsis thaliana* CPN-60 (nucleotides 74-186] and COX4 [the first 25 codons of *Saccharomyces cerevisiae* COX4 which encodes the mitochondrial targeting sequence].

Chloroplast localization signals which may be used according to the present teachings include, but are not limited to the transition signals of the ribulose-1,5-bisphosphate carboxylase (Rubisco) small subunit (ats1A) associated transit peptide, the transition signal of LHC II, as well as the N-terminal regions of *A. thaliana* SIG2 and SIG3 ORFs. See also www(dot)springerlink(dot)com/content/p65013h263617795/.

Alternatively, the chloroplast localization sequence (CLS) may be derived from a viroid [Evans and Pradhan (2004) US 2004/0142476 A1]. The viroid may be an Avsunviroidae viroid, for example, an Avocado Sunblotch Viroid (ASBVd), a Peach Latent Mosaic Virus (PLMVd), a *Chrysanthemum* Chlorotic Mottle Viroid (CChMVd) or an Eggplant Latent Viroid (ELVd).

According to a specific embodiment of the present invention, the localization signal may comprise a chloroplast localization signal.

In some embodiments, the heterologous polypeptide of interest (e.g. nuclease) further comprises at least one cell-penetrating domain. In one embodiment, the cell-penetrating domain can be a cell-penetrating peptide (CPP) sequence derived from Tat, Tat2, arginine-rich intracellular delivery peptides (AID), pVEC, transportan and penetratin.

According to a specific embodiment of the present invention, the CPP sequence comprises a dimmer of the Tat molecule (Tat2) which has an increased ability to translocate across plant cell membranes because of the presence of high number of arginine residues.

According to an aspect of some embodiments of the invention, there is provided a method of producing a transgenic plant, comprising expressing within the plant the nucleic acid construct of some embodiments of the invention.

The phrase "expressing within the plant" as used herein refers to upregulating the expression level within the plant of the exogenous polynucleotide comprised in the nucleic acid construct, by introducing the nucleic acid construct into a plant cell or a plant and expressing by recombinant means, as further described herein below.

According to an aspect there is provided a method of producing a plant, the method comprises, transforming cells of a plant of interest with the polynucleotide or the nucleic acid construct.

According to a specific embodiment, the transformation comprises a transient transformation.

According to a specific embodiment, the transformation comprises a stable transformation.

Various methods are known for plant transformation. For example, transient transformation can be done in the absence of a selection marker for 3-14 days. Stable transformation will typically require 4-10 weeks in the presence of a selection marker (e.g., antibiotics). Further transformation protocols are described hereinbelow.

The delivery of nucleic acids into a plant cell (contacted) in embodiments of the invention can be done by any method known to those of skill in the art, including, for example and without limitation: by desiccation/inhibition-mediated DNA uptake (See, e.g., Potrykus et al. (1985) Mol. Gen. Genet. 199:183-8); by electroporation (See, e.g., U.S. Pat. No. 5,384,253); by agitation with silicon carbide fibers (See, e.g., U.S. Pat. Nos. 5,302,523 and 5,464,765); by *Agrobacterium*-mediated transformation (See, e.g., U.S. Pat. Nos. 5,563,055, 5,591,616, 5,693,512, 5,824,877, 5,981,840, and 6,384,301); by acceleration of DNA-coated particles (See, e.g., U.S. Pat. Nos. 5,015,580, 5,550,318, 5,538,880, 6,160,208, 6,399,861, and 6,403,865) and by Nanoparticles, nanocarriers and cell penetrating peptides (WO201126644A2; WO2009046384A1; WO2008148223A1) in the methods to deliver DNA, RNA, Peptides and/or proteins or combinations of nucleic acids and peptides into plant cells.

Other methods of transfection include the use of transfection reagents (e.g. Lipofectin, ThermoFisher), dendrimers (Kukowska-Latallo, J. F. et al., 1996, Proc. Natl. Acad. Sci. USA93, 4897-902), cell penetrating peptides (Mae et al., 2005, Internalisation of cell-penetrating peptides into tobacco protoplasts, Biochimica et Biophysica Acta 1669 (2):101-7) or polyamines (Zhang and Vinogradov, 2010, Short biodegradable polyamines for gene delivery and transfection of brain capillary endothelial cells, J Control Release, 143(3):359-366).

According to a specific embodiment, the introduction of DNA into plant cells is effected by electroporation.

According to a specific embodiment, the introduction of DNA into plant cells is effected by bombardment/biolistics.

According to a specific embodiment, the introduction of DNA into plant cells is effected by *Agrobacterium* mediated transformation.

Viruses that have been shown to be useful for the transformation of plant hosts include CaMV, TMV, TRV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of some embodiments of the invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that the sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

Genome transformation can be evaluated phenotypically, i.e., by the presence/absence of a certain trait e.g., antibiotic resistance, resistance to disease or herbicide, morphologically (e.g., plant height), reporter gene expression (e.g., GUS) etc.

Genome transformation can also be evaluated molecularly. This is of specific significance in the case of genome editing.

Thus, regenerated tissues/plants are validated for the presence of a transformation event. The following provides such validation methods for genome editing events, also referred to herein as "mutation" or "edit", dependent on the type of editing sought e.g., insertion, deletion, insertion-deletion (Indel), inversion, substitution and combinations thereof.

Methods for detecting sequence alteration are well known in the art and include, but not limited to, DNA sequencing (e.g., next generation sequencing), electrophoresis, an enzyme-based mismatch detection assay and a hybridization assay such as PCR, RT-PCR, RNase protection, in-situ hybridization, primer extension, Southern blot, Northern Blot and dot blot analysis. Various methods used for detection of single nucleotide polymorphisms (SNPs) can also be used, such as PCR based T7 endonuclease, Hetroduplex and Sanger sequencing.

Another method of validating the presence of a DNA editing event e.g., Indels comprises a mismatch cleavage assay that makes use of a structure selective enzyme (e,g, m endonuclease) that recognizes and cleaves mismatched DNA.

The mismatch cleavage assay is a simple and cost-effective method for the detection of indels and is therefore the typical procedure to detect mutations induced by genome editing. The assay uses enzymes that cleave heteroduplex DNA at mismatches and extrahelical loops formed by multiple nucleotides, yielding two or more smaller fragments. A PCR product of ~300-1000 bp is generated with the predicted nuclease cleavage site off-center so that the resulting fragments are dissimilar in size and can easily be resolved by conventional gel electrophoresis or high-performance liquid chromatography (HPLC). End-labeled digestion products can also be analyzed by automated gel or capillary electrophoresis. The frequency of indels at the locus can be estimated by measuring the integrated intensities of the PCR amplicon and cleaved DNA bands. The digestion step takes 15-60 min, and when the DNA preparation and PCR steps are added the entire assays can be completed in <3 h.

Two alternative enzymes are typically used in this assay. T7 endonuclease 1 (T7E1) is a resolvase that recognizes and cleaves imperfectly matched DNA at the first, second or third phosphodiester bond upstream of the mismatch. The sensitivity of a T7E1-based assay is 0.5-5%. In contrast, Surveyor™ nuclease (Transgenomic Inc., Omaha, NE, USA) is a member of the CEL family of mismatch-specific nucleases derived from celery. It recognizes and cleaves mismatches due to the presence of single nucleotide polymorphisms (SNPs) or small indels, cleaving both DNA strands downstream of the mismatch. It can detect indels of up to 12 nt and is sensitive to mutations present at frequencies as low as ~3%, i.e. 1 in 32 copies.

Yet another method of validating the presence of an editing even comprises the high-resolution melting analysis.

High-resolution melting analysis (HRMA) involves the amplification of a DNA sequence spanning the genomic target (90-200 bp) by real-time PCR with the incorporation of a fluorescent dye, followed by melt curve analysis of the amplicons. HRMA is based on the loss of fluorescence when intercalating dyes are released from double-stranded DNA during thermal denaturation. It records the temperature-dependent denaturation profile of amplicons and detects whether the melting process involves one or more molecular species.

Yet another method is the heteroduplex mobility assay. Mutations can also be detected by analyzing re-hybridized PCR fragments directly by native polyacrylamide gel electrophoresis (PAGE). This method takes advantage of the differential migration of heteroduplex and homoduplex DNA in polyacrylamide gels. The angle between matched and mismatched DNA strands caused by an indel means that heteroduplex DNA migrates at a significantly slower rate than homoduplex DNA under native conditions, and they can easily be distinguished based on their mobility. Fragments of 140-170 bp can be separated in a 15% polyacrylamide gel. The sensitivity of such assays can approach 0.5% under optimal conditions, which is similar to T7E1 (. After reannealing the PCR products, the electrophoresis component of the assay takes ~2 h.

Other methods of validating the presence of editing events are described in length in Zischewski 2017 Biotechnol. Advances 1(1):95-104.

It will be appreciated that positive clones can be homozygous or heterozygous for the transformation event. The skilled artisan will select the clone for further culturing/regeneration according to the intended use.

It will be appreciated that crossing of the plant can be effected to improve agricultural traits, losing a transgene, also known as "crossing out" (e.g., nuclease after genome editing was successfully implemented), or generation of inbreds or hybrids.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores.

Plants that may be useful in the methods of the invention include all plants which belong to the superfamily Viridiplantee, in particular monocotyledonous and dicotyledonous plants.

The terms "*cannabis*" refers to the genus which includes all different species including *Cannabis sativa, Cannabis* indica and *Cannabis ruderalis* as well as wild *Cannabis.*

*Cannabis* is diploid, having a chromosome complement of 2n=20, although polyploid individuals have been artificially produced and are also contemplated herein. The first genome sequence of *Cannabis*, which is estimated to be 820 Mb in size, was published in 2011 by a team of Canadian scientists (van Bakel et al, supra).

All known strains of *Cannabis* are wind-pollinated and the fruit is an achene. Most strains of *Cannabis* are short day plants, with the possible exception of *C. sativa* subsp. *sativa* var. spontanea (=*C. ruderalis*), which is commonly described as "auto-flowering" and may be day-neutral.

According to a specific embodiment, the plant is of *C. sativa.*

*Cannabis* has long been used for drug and industrial purposes: fiber (hemp), for seed and seed oils, extracts for medicinal purposes, and as a recreational drug. The selected genetic background (e.g., cultivar) depends on the future use. Industrial hemp products are made from *Cannabis* plants selected to produce an abundance of fiber. Some *Cannabis* strains have been bred to produce minimal levels of THC, the principal psychoactive constituent responsible for the psychoactivity associated with marijuana. Marijuana has historically consisted of the dried flowers of *Cannabis* plants selectively bred to produce high levels of THC and other psychoactive cannabinoids. Various extracts including hashish and hash oil are also produced from the plant.

Thus, for example, a CBD rich strain can be selected from a group consisting of Golan, Avidekel, Fedora 17, ACDC, and any combination thereof; or wherein the *cannabis* plant is a THC rich strain; the THC rich strain is selected from a group consisting of Everest, Black Destroyer, Critical Neville Haze, Mataro Blue, LSD OG Kush, Pineapple Chunk, Blue Monster Holk, Y Griega, Satori, Tutankhamon, and any combination thereof.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the characteristics and iii) considered as a unit with regard to its suitability for being propagated unchanged.

The term "variety" is interchangeable with "cultivar".

Thus, contemplated herein, novel promoters, nucleic acid constructs or plant cells comprising same and methods of producing plants comprising an expression product of interest and/or a genome editing event of interest.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, a given SEQ ID NO: is expressed in a DNA sequence format (e.g., reciting T for thymine), but it can refer to either a DNA sequence that corresponds to the nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Site-Directed Mutagenesis by Transit Activation of mGUS in *Cannabis*

The use of CRISPR-Cas system is contemplated herein for the induction of targeted mutagenesis in defined loci in the *Cannabis* genome. Using a mutated gene encoding GUS (mGAS) as a convenient target, it is shown that mGUS specific gRNA expression can lead to changes in the target reporter gene.

Materials and Methods

Plant Material

A *cannabis* cultivar with high THC and other cannabinoids for medical and recreational usage were grown from seeds and tissue culture. *Cannabis* leaf tissue cultures, cotyledons and calli were used for transformation.

Plasmids

Two plasmids were used in this study: pRCS2-[Kan][35S::mGUS]— binary vector carrying the mutated GUS-encoding gene and the TGA stop codon 13 bp downstream of ATG, under the control of the 35S promoter; pRCS2-[Kan][35s::hCas9-U6::sgRNA-mGUS]—binary vector carrying 35s promoter-driven hCas9 and U6 promoter-driven gRNA targeting the STOP codon in the mGUS. A schematic description of the two T-DNA is presented in FIG. 1A. For specific elements in the expression construct see, Peer, Reut, et al, "Targeted mutagenesis using zinc-finger nucleases in perennial fruit trees." *Planta* 241.4 (2015): 941-951.

*Cannabis* Transient Transformation

General protocol according to Peer, Reut, et al. "Targeted mutagenesis using zinc-finger nucleases in perennial fruit trees." *Planta* 241.4 (2015): 941-951.

The *Agrobacterium tumefaciens* strain EHA105 was grown overnight at 28° C. in an LB medium supplemented with suitable antibiotics. Bacteria were spun down by centrifugation (8000 g for 10 min), resuspended in an infiltration buffer (0.5 MS, 3% sucrose and 100 μM acetosyringone) to a final OD600 of 0.7, and incubated in an orbital shaker at 28° C., 200 rpm for 4 h, until plant infection. The explants, 10 days old *cannabis* tissue culture, were transferred into *Agrobacterium* suspension and infiltration was performed by vacuum (Knf Neuberger D-79112) for 20 min followed by 1 h incubation at 27±1° C., following with 3 days co-cultivation and 7 days of recovery.

Histochemical GUS Assay

Histochemical analysis was performed by vacuum-infiltration following the procedure of Jefferson et al. (1987) *The EMBO journal* 6.13 (1987): 3901-3907.

Result

Validation of the CRISPR/Cas9 Methodology in *Cannabis*

To examine the function of 35s::hCas9-U6::sgRNA-mGUS in *Cannabis*, a visual transgenic repair assay was used. This assay is based on activation of a mutated uidA reporter gene carrying a TGA stop codon within the 6-bp spacer of the 35s::hCas9-U6::sgRNA-mGUS target site, leading to premature termination of GUS translation in plant cells. Expression of 35s::hCas9-U6::sgRNA-mGUS will lead to digestion within the ZFN target site, and consequent misrepair of the double-strand break by the plant's NHEJ machinery may lead to modification (deletion or alteration) of the target sequence and to GUS expression. To validate the function of 35s::hCas9-U6::sgRNA-mGUS in *Cannabis*, simultaneous transient expression of two binary vectors was used, pRCS2 [Kan][35S::mGUS], carrying the mutated GUS-encoding gene and the TGA stop codon 13 bp downstream of ATG, under the control of the 35S promoter and pRCS2 [Kan][35s::hCas9-U6::sgRNA-mGUS] binary vector, carrying 35s promoter-driven hCas9 and U6 promoter-driven gRNA targeting the STOP codon in the mGUS, on a *Cannabis* leaf tissue culture. Transient transformation via *Agrobacterium* infiltration led to reconstruction of GUS activity (FIG. 1C). GUS activity was clearly observed 10 days after *Agrobacterium* inoculation, as reflected by the GUS staining of leaves in the areas of *Agrobacterium* infiltration. No GUS activity was observed in control tissues infected with pRCS2 [Kan][35s::hCas9-U6::sgRNA-mGUS] binary vector construct alone (FIG. 1D).

Conclusions

The present results show successful genome editing in a transient expression system. Together with improvements in mutation efficiency and gene targeting using CRISPR/Cas9, such systems would contribute to further molecular breeding to generate desired *Cannabis* traits.

Example 2

Identifications of Novel *Cannabis* Promoters for Heterologous Gene Expression Materials and Methods Identification of *Cannabis* Housekeeping Genes and Promoters

| Promoter | Primers/SEQ ID NOs: | SEQ ID NO: |
|---|---|---|
| CsPS2 | 5'GGTGACTGATTCCCTCAATTTCCC3' (SEQ ID NO: 41) and 5'TAAAGAAGCTCCCATACCCATCTTTTGC3' (SEQ ID NO: 42) | 4 |

-continued

| Promoter | Primers/SEQ ID NOs: | SEQ ID NO: |
|---|---|---|
| CsUBIQ | 5'CCGTGAAAACTTAACACAGTACAC3' (SEQ ID NO: 35) and 5'CTAAAAATACAGAATTAAAACAAAATCTATC3' (SEQ ID NO: 36) | 2 |
| CsActin | | 6 |
| CsEIF | | 10 |
| CsTubulin | | 8 |

Cloning the GUS Gene Under Different Promoters

The GUS gene was amplified from the pME504 vector with the primers ATGTTACGTCCTGTAGAAACCC (SEQ ID NO: 56) and TCATTGTTTGCCTCCCTGCTGCG (SEQ ID NO: 57). Using BsaI restriction enzyme, this gene was then cloned into the pCAMBIA vector fused to the tomato UBIQUITIN10 (SlUBIQ), *Cannabis* UBIQUITIN10 (CsUBIQ) (SEQ ID NO: 1), *Cannabis* Photosystem II reaction center W protein (CsPS2) (SEQ ID NO: 3), or CaMV-35S (35S) (Kay, Robert, et al, "Duplication of CaMV 35S promoter sequences creates a strong enhancer for plant genes." *Science* 236.4806 (1987): 1299-1302) promoters.

Plant Transformation and GUS Staining

The resulting plasmids were used to transform *Agrobacterium* (strain EHA105). Resulting colonies were grown in LB broth and resuspended in MSO prior to plant infection. Agrobacteria were vacuum infiltrated into two different *Cannabis sativa* leaves cultivars (108, 213 i.e., Finola hemp variety High THC cultivar—SLH). Next, GUS activity was detected in situ using X-GLUC. After overnight staining, the *Cannabis* leaf samples were destained and subsequently photographed.

Results

Improvement of Gene Expression by the Use of *Cannabis* Housekeeping Genes Promoters The two *Cannabis* promoters UBIQUITIN10, the Photosystem II reaction center W protein (CsPS2) were cloned into the pCAMBIA vector upstream the GUS reporter gene and were further used for GUS activity assay in compassion to 35S. The resulting plasmids were then used for *Agrobacterium* transformation (strain EHA105). Then, *Cannabis* leaves were infiltrated with Agrobacteria containing the various plasmids, and subjected to GUS staining. GUS activity was detected in *planta* using X-GLUC. It was found that the two *Cannabis* promoters direct gene expression in a stronger manner than the CaMV-35S (FIGS. 3B-C), and the tomato SlUBIQ10 promoter. Moreover, these promoters also directed GUS gene expression in a more stable manner. In additional experiments, these promoters were used to direct CAS9 expression to improve genome editing efficiency.

TABLE 1

List of promoters used to achieve maximum gene expression in Cannabis

| | Average Expression (FPKM*) | | | | | | |
|---|---|---|---|---|---|---|---|
| Gene name | Roots | Buds | Mature Flower | Young Leaf | Mature Leaf | Entire Primary Stem | Entire Petioles |
| Metallothionein | 547.57 | 697.26 | 776.41 | 284.20 | 631.81 | 482.60 | 283.51 |
| Catalase | 567.11 | 310.60 | 453.99 | 882.36 | 740.26 | 233.57 | 321.26 |
| 60S ribosomal protein L3 | 456.06 | 556.56 | 809.60 | 427.13 | 288.73 | 659.33 | 707.76 |
| Asparagine synthetase | 92.16 | 751.34 | 862.29 | 1076.10 | 338.14 | 40.97 | 15.68 |
| 40S ribosomal protein S3a | 439.43 | 476.68 | 621.17 | 526.64 | 439.60 | 526.62 | 489.58 |
| Phi-1 protein | 2257.98 | 21.14 | 23.89 | 420.33 | 584.36 | 1184.49 | 930.91 |
| Receptor for activated protein kinase C | 444.55 | 517.84 | 778.56 | 474.86 | 318.22 | 336.59 | 491.39 |

Conclusion

Interestingly the expression of CsUbiqutin10 promoter was by far higher than that of the known 35s virus promoter.

Example 3

Genome Editing of *Cannabis* PHYTOENE DESATURASE (PDS) Gene Using the *Cannabis* UBIQUITIN10 Constitutive Promoter Material and Methods Cs PDS Gene Isolation The sequence of the *Cannabis* PDS protein and the expression level of the CsPDS gene were retrieved from the database available at medicinalplantgenomics(dot)msu(dot) edu/(dpt) Sequence alignment was performed using Clustal Omega, available at medicinalplantgenomics(dot)msu(dot) edu/(dot) The phylogenetic relationship was determined with an online tool available at Phylogeny.fr.

gRNA Design, Plasmid Preparation, and *Agrobacterium* Transformation.

gRNAs were designed and synthesized in the form oligonucleotides as follows (the gRNA is underlined):

```
CS_PDS_gRNA KO1:
                                          (SEQ ID NO: 49)
5'tgtggtctcaATTGTTAACTTTTTGGAAGCTGgttttagagctagaaa
tagcaa g3'
```

-continued

CS_PDS_gRNA_KO2_F:

(SEQ ID NO: 50)

5'tgtggtctcaATTGCGAAATACTTGGCAGATGCgttttagagctagaaatagcaag3'

Target sequences were each fused to the *Arabidopsis* U6 promoter and to the gRNA sequence and cloned into the pICH47751 plasmid. The resulting cassettes were combined and cloned into the pAGM4723 binary vector together with the CAS9 gene (under the UBIQUITIN10 promoter, SEQ ID NO: 2) and NPTII. The resulting plasmid was used for *agrobacterium* transformation. *Agrobacterium* colonies were selected on kanamycin containing medium.

*Cannabis* Transient Transformation and GUS Activity Detection.

Agrobacteria containing the plasmid grown overnight in LB broth were resuspended in MSO to $OD_{600}$=1 prior to infiltration. *Cannabis* seedlings were grown for 5 days. One cotyledon was removed from each seedling prior to *Agrobacterium* infiltration under vacuum. Co-infiltration was performed using the abovementioned *Agrobacterium* and Pme504 containing *Agrobacterium*. After 3 days, GUS activity was determined in the developing foliage using the X-GLUC.

*Cannabis* DNA Extraction.

Total genomic DNA (gDNA) was extracted from *Cannabis* leaves colored in blue on three independent biological replicates (numbered #1, #2, and #4) and one wild type as control.

Enrichment to Detect Mutagenesis in the CsPDS Gene. PCR was performed on the gDNA [using the primers CACTCTCATAGTTTAACTATTTCG (SEQ ID NO: 19) and TAAGAAAGTTCAATTAGCTTATGT(SEQ ID NO: 20)] in the following conditions:

| | |
|---|---|
| 94° C., 2 min. | |
| 94° C., 30 sec. | |
| 50° C., 30 sec. | 23 cycles. |
| 72° C., 30 sec. | |
| 72° C., 5 min. | |

PCR product was then SfaN1-digested.

This procedure was performed 3 additional times (total 4 cycles of PCR/SfaN1 digestion). The PCR products were ligated into the PCR vector (Life Technologies), and 4 random colonies were selected for DNA sequencing.

Results

In order to identify the *Cannabis* PDS gene (SEQ ID NO: 58, 59), the amino acid sequence of the tomato, *Arabidopsis*, and maize PDS proteins were used as a query in BLAST analysis against the database available at medicinalplantgenomics(dot)msu(dot)edu/(dot) This analysis returned the *Cannabis* protein sequences with very high homology (E value=0). The identification of this sequence was further corroborated using bioinformatic tools.

In order to mutagenize the CsPDS, two gRNAs (SEQ ID NOs: 49 and 50) were designed and cloned the pICH47751 plasmid. The resulting cassettes were combined and cloned into the pAGM4723 binary vector together with the CAS9 gene (under the CsUBIQUITIN10 promoter) and NPTII. The resulting plasmid was used to transform *Agrobacterium*, and transformants were infiltrated into *Cannabis* leaves together with *Agrobacterium* containing the pME504 vector. Using this strategy, it was expected that the resulting blue color obtained in *Cannabis* leaves after GUS staining would indicate transformed tissues where mutagenesis occurred. Therefore, genomic DNA was extracted from these regions only and determined the plant transformation by PCR with primers specific for GUS reporter gene and for the NPTII gene (FIGS. 4A-B).

Four rounds of enrichment were performed. These enrichments included PCR amplification with the primers flanking the gRNA #1 (to identify the PDS) followed by SfaN1 digestion. Since mutagenized fragments would be resistant to SfaN1 digestion, these rounds would enrich the mutagenized fragments in the amplicons. After four rounds, a clear fragment was obtained from the genomic DNA #1 (FIGS. 5A-B). This fragment was gel extracted and cloned into pTZ. Four colonies were grown prior to plasmid extraction. Sequencing the resulting plasmids revealed mutations in the gRNA target (FIG. 6).

Conclusion

In this study, the UBIQUITIN 10 *Cannabis* promoter was used to efficiently deliver Cas9, along with a synthetic sgRNA targeting the CsPDS gene, into *Cannabis*. DNA sequencing confirmed that the CsPDS gene was mutated at the target site in treated *Cannabis* leaves. The mutation rate using the Cas9/sgRNA system was approximately 3.2 to 3.9%, while off-target mutagenesis was not detected for CsPDS-related DNA sequences in this study. This is the first report of targeted genome modification in *Cannabis* using the Cas9/sgRNA system, thus providing a very promising tool for the study of *Cannabis* gene function and for targeted genetic modification.

Example 4

Site-Directed Mutagenesis of a *Cannabis* Endogenous Gene, the THC Synthase Using the *Cannabis* UBIQUITIN10 Constitutive Promoter Material and Methods THC Synthase gRNA Design and Plasmid Preparation.

The THC synthase (Accession Number AB057805.1) gRNAs were designed (FIG. 7 marked by an underline) and synthesized in the form oligo-nucleotides (FIG. 8A). The gRNAwere each fused to the *Arabidopsis* U6 promoter and cloned into the pICH47751 plasmid. The resulting cassettes were combined and cloned into the pAGM4723 binary vector together with the CAS9 gene (under the *cannabis* UBIQUITIN10) and NPTII. The resulting plasmid was used for *Agrobacterium* transformation.

*Cannabis* Transient Transformation

*Agrobacterium tumefaciens* strain EHA105 was grown overnight at 28° C. in LB medium supplemented with suitable antibiotics. Bacteria were spun down by centrifugation (8000 g for 10 min), resuspended in an infiltration buffer (0.5 MS, 3% sucrose and 100 μM acetosyringone) to a final OD600 of 0.7, and incubated in an orbital shaker at 28° C., 200 rpm for 4 h, until plant infection. The explants, 35 days old *cannabis* tissue culture, were transferred into *Agrobacterium* suspension and infiltration was performed by vacuum (Knf Neuberger D-79112) for 20 min followed by 1 h incubation at 27±1° C., following with 3 days cocultivation and 7 days of recovery.

Histochemical GUS Assay

Histochemical analysis was performed by vacuum-infiltration following the procedure of Jefferson et al. (1987), supra.

Molecular Detection of Mutagenesis in the CsTHC Syntes Gene.

For molecular analysis of targeting events, total DNA was extracted using the REDExtract-N-Amp Plant Kit (Sigma-Aldrich). PCR analysis was performed using primers flanking the target sequence and Extract-N-Amp Plant PCR Kit (Sigma-Aldrich).

The primers were:

```
                                    (SEQ ID NO: 60)
CCTCGAGAAAACTTCCTTAAATG;
and

                                    (SEQ ID NO: 51)
CCAATTGTATATGT CTATCCTGA
```

The PCR conditions were:

| | |
|---|---|
| 94° C., 2 min. | |
| 94° C., 30 sec. | |
| 50° C., 30 sec. | 23 cycles. |
| 72° C., 30 sec. | |
| 72° C., 5 min. | |

The PCR product was then digested with the XhoI and MfeI restriction enzyme, followed by sequencing of the uncut PCR products.

Results

Mutagenesis of the *Cannabis* THC Synthase Gene.

In order to mutagenize the *Cannabis* THC synthase gene (CsTHC, FIG. 7), two gRNAs (highlighted sequences in FIG. 7) were designed and cloned to the pICH47751 plasmid. The resulting cassettes were combined and cloned into the pAGM4723 binary vector together with the CAS9 gene (under the CsUBIQUITIN10 promoter) and NPTII. The resulting plasmid was used to transform *Agrobacterium*, and transformants were infiltrated into *Cannabis* leaves together with *Agrobacterium* containing the pME vector. Using this strategy, it was expected that the blue color obtained in *Cannabis* leaves after GUS staining would indicate transformed tissues where mutagenesis may occur. Therefore genomic DNA was extracted from these regions only and the plant transformation was determined by PCR with primers specific for GUS reporter gene and for the NPTII gene (FIG. 9, SEQ ID NOs: 56 and 67).

Four rounds of enrichment were performed. These enrichments consisted of PCR amplification with the primers (SEQ ID NOs: 60-51) flanking the gRNA #1 followed by SfaN1 digestion. Since mutagenized fragments would be resistant to SfaN1 digestion, these rounds would enrich the mutagenized fragments in the amplicons. After four rounds, a clear distinct fragment was obtained from the genomic DNA #1 (FIG. 9). This fragment was gel extracted and cloned into pTZ. Four colonies were grown prior to plasmid extraction. Sequencing the resulting plasmids revealed mutations in the gRNA target (FIG. 9).

Gene-modification events were detected by molecular analysis. Total DNA was extracted from GUS staining tissue, PCR analysis was performed using primers flanking the target sequence and was then digested with the XhoI and MfeI restriction enzymes, followed by sequencing of the uncut PCR products (FIG. 9).

Example 5

Isolation of Additional *Cannabis* Constitutive Promoters, to Achieve Maximum Gene Expression in *Cannabis*

Materials and Methods

Isolation of the *Cannabis* Promoters

Highly expressed *Cannabis* genes were further identified from the publicly available transcription database (medicinalplantgenomics(dot)msu(dot)edu/index(dot)shtml). Next, the sequences upstream these highly expressed genes were retrieved from the publicly available *Cannabis* genome database (genome(dot)ccbr(dot)utoronto(dot)ca/index.html?org=C.+*sativa*&db=canSat3&hgsid=97270).

Results

Table 2 and the following sequences upstream the genes, retrieved from the publicly available *Cannabis* genome database, summarized additional potential *Cannabis* promoters to be use for efficient genome editing in *Cannabis* and potentially in other plants.

TABLE 2

List of promoters used to achieve maximum gene expression in Cannabis

| | Average Expression (FPKM*) | | | | | | |
|---|---|---|---|---|---|---|---|
| Gene name | Roots | Buds | Mature Flower | Young Leaf | Mature Leaf | Entire Primary Stem | Entire Petioles |
| Metallothionein (SEQ ID NO: 28) | 547.57 | 697.26 | 776.41 | 284.20 | 631.81 | 482.60 | 283.51 |
| Catalase (SEQ ID NO: 29) | 567.11 | 310.60 | 453.99 | 882.36 | 740.26 | 233.57 | 321.26 |
| 60S ribosomal protein L3 (SEQ ID NO: 34) | 456.06 | 556.56 | 809.60 | 427.13 | 288.73 | 659.33 | 707.76 |
| Asparagine synthetase (SEQ ID NO: 32) | 92.16 | 751.34 | 862.29 | 1076.10 | 338.14 | 40.97 | 15.68 |
| 40S ribosomal protein S3a (SEQ ID NO: 38) | 439.43 | 476.68 | 621.17 | 526.64 | 439.60 | 526.62 | 489.58 |
| Phi-1 protein (SEQ ID NO: 40) | 2257.98 | 21.14 | 23.89 | 420.33 | 584.36 | 1184.49 | 930.91 |
| Receptor for activated protein kinase C (SEQ ID NO: 44) | 444.55 | 517.84 | 778.56 | 474.86 | 318.22 | 336.59 | 491.39 |

*Fragments Per Kilobase of transcript per Million mapped reads

The promoters regions are shown in FIG. 10 along with their SEQ ID NO.

Example 6

Site-Directed Mutagenesis in *Cannabis* Using Enhanced Somatic Embryogenesis *Cannabis* Genes Materials and Methods The *Cannabis* BABYBOOM (CsBBM) and SOMATIC EMBRYOGENESIS RECEPTOR KINASE1 (CsSERK1) genes were identified by Blast analysis in the database available at medicinalplantgenomics(dot)msu(dot)edu/index (dot)shtml. Then, candidate genes were isolated from cDNA generated out of RNA from regenerating *Cannabis* callus using the primers 5'ATGAGTATTATTACTAATGA-TAGTAATCTCAG3' (SEQ ID NO: 52) and TTATTC-CATGCCGAATATTGGTGTT3' (SEQ ID NO: 53) for CsBBM, and 5' ATGGAAGGTGATGCCTTGCATAGTC3' (SEQ ID NO: 54) and 5'TTACCTCGGACCAGA-TAACTCGACC3' (SEQ II) NO: 55) for CsSERK1. These two genes were cloned under the control of the *Cannabis* UBIQUITIN10 (CsUSBIQUITIN10 (promoter using standard cloning procedures, and subsequently fused to a cassette containing the CASA) genes and the relevant gRNAs.

Results

Identification and Isolation of the CsBBM and CsSERK1 Genes

In order to identify the homologous genes of the BBM and SERK1 genes in *Cannabis*, blast analysis was performed using the *Arabidopsis* BBM and SERK1 genes as a bait. The sequences of the genes that show the highest homology to these genes are shown in FIG. 11. To isolate the CsBBM and CsSERK1 genes, total RNA was extracted from *Cannabis* calli, followed by cDNA synthesis.

Genome Editing Cassette in *Cannabis*

These cDNA (SEQ ID NOs: 45 and 47) were amplified using specific primers for the CsBBM and CsSERK1 genes (SEQ ID NOs: 52-55) and cloned into pCAMBIA binary vectors under the control of the constitutive or inducible promoter, and fused to an expression cassette of the CAS9 gene, under the control of the CsUBIQUITIN10 promoter (FIG. 12).

Efficient *Cannabis* genome editing cassette is achieved by using both constitutive expression of CAS9 DNA editing agent, by the *Cannabis* UR/Mir/NM (or other *Cannabis* constitutive promoter) that is fused to the relevant gRNAs and two embryogenesis genes CsBBM and CsSERK1 under the control of a constitutive or inducible promoter (FIG. 12).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A polynucleotide comprising a nucleic acid sequence encoding an expression product of interest under a transcriptional control of a heterologous cis-acting regulatory element comprising a nucleic acid sequence at least 95% identical to SEQ ID NO: 2.

2. A nucleic acid construct comprising the polynucleotide of claim 1.

3. A cloning nucleic acid construct comprising a cis-acting regulatory element comprising a nucleic acid sequence at least 95% identical to SEQ ID NO: 2 and at least one of a multiple cloning site and a selection marker coding sequence, said cis-acting regulatory element being heterologous to said at least one of said multiple cloning site and said selection marker coding sequence.

4. A cell comprising the nucleic acid construct of claim 2.

5. The cell of claim 4 being a bacterial cell.

6. The cell of claim 4 being a plant cell.

7. A plant or portion thereof comprising the nucleic acid construct of claim 2.

8. A method of producing a plant, the method comprises, transforming cells of a plant of interest with the nucleic acid construct of claim 2, to obtain a plant transformed with the nucleic acid construct, thereby producing the plant.

9. The method of claim 8 further comprising regenerating a plant from cells of the plant transformed with the nucleic acid construct.

10. The method of claim 9 further comprises selfing or crossing the plant transformed with the nucleic acid construct.

11. The nucleic acid construct of claim 2, wherein the heterologous cis-acting regulatory element comprises a nucleic acid sequence set forth in SEQ ID NO: 2.

12. The nucleic acid of claim 2, wherein the expression product of interest comprises a DNA editing agent.

13. The cell of claim 6, wherein the plant is *Cannabis* saliva.

14. The nucleic acid construct of claim 11, wherein the coding sequence comprises SEQ ID NO 45 or SEQ ID NO: 47.

15. The nucleic acid construct of claim 12, wherein the DNA editing agent comprises a double strand endonuclease.

* * * * *